US010037841B2

(12) United States Patent
Suzara

(10) Patent No.: US 10,037,841 B2
(45) Date of Patent: Jul. 31, 2018

(54) MAGNETIC FIELD STRUCTURES, FIELD GENERATORS, NAVIGATION AND IMAGING FOR UNTETHERED ROBOTIC DEVICE ENABLED MEDICAL PROCEDURE

(71) Applicant: Vincent Suzara, La Jolla, CA (US)

(72) Inventor: Vincent Suzara, La Jolla, CA (US)

(73) Assignee: Vincent Suzara, San Diego, CA (US)

( * ) Notice: Subject to any disclaimer, the term of this patent is extended or adjusted under 35 U.S.C. 154(b) by 0 days.

(21) Appl. No.: 14/884,748

(22) Filed: Oct. 15, 2015

(65) Prior Publication Data

US 2016/0111192 A1    Apr. 21, 2016

Related U.S. Application Data

(60) Provisional application No. 62/064,372, filed on Oct. 15, 2014.

(51) Int. Cl.
| | |
|---|---|
| *H01F 6/06* | (2006.01) |
| *H01F 7/20* | (2006.01) |
| *G01R 33/381* | (2006.01) |
| *A61B 34/30* | (2016.01) |
| *A61B 5/055* | (2006.01) |
| *G01R 33/3815* | (2006.01) |

(Continued)

(52) U.S. Cl.
CPC .............. *H01F 6/06* (2013.01); *A61B 34/30* (2016.02); *G01R 33/381* (2013.01); *H01F 7/202* (2013.01); *A61B 5/055* (2013.01); *A61B 2090/3954* (2016.02); *G01R 33/3815* (2013.01); *G01R 33/4215* (2013.01)

(58) Field of Classification Search
CPC ......... H01F 6/06; H01F 7/202; G01R 33/381; G01R 33/3815; G01R 33/4215; A61B 34/30; A61B 2090/3954; A61B 5/055
See application file for complete search history.

(56) References Cited

U.S. PATENT DOCUMENTS

| 4,590,428 A | * | 5/1986 | Muller | G01R 33/381 324/315 |
| 4,748,414 A | * | 5/1988 | Knuttel | G01R 33/381 324/318 |

(Continued)

FOREIGN PATENT DOCUMENTS

| JP | 2002-233575 A | 8/2002 |
| JP | 2005-161052 A | 6/2005 |

OTHER PUBLICATIONS

Written Opinion of the International Searching Authority for PCT/US2015/055835, dated Feb. 1, 2016.

(Continued)

*Primary Examiner* — Mohamad Musleh
(74) *Attorney, Agent, or Firm* — Kathleen Mekjian

(57) ABSTRACT

A magnetic field generating apparatus comprises two or more co-facing, coaxial magnetic field generators configured to generate equivalent magnetic fields directed toward a symmetrically central convergence plane; a magnetically shielding encasement configured to contain all of the associated magnetic fields generated by the coaxial magnetic field generators; and articulation frames and supports for positioning of the apparatus about a fixed point, wherein the generated magnetic fields are counter-rotated relative to one another.

20 Claims, 21 Drawing Sheets

(51) Int. Cl.
    *G01R 33/421*    (2006.01)
    *A61B 90/00*     (2016.01)

(56) References Cited

U.S. PATENT DOCUMENTS

| | | | | |
|---|---|---|---|---|
| 5,162,768 A * | 11/1992 | McDougall | ........ | G01R 33/3815 |
| | | | | 324/318 |
| 6,011,394 A | 1/2000 | Petropoulos | | |
| 6,150,820 A * | 11/2000 | Damadian | .............. | A61B 5/055 |
| | | | | 324/319 |
| 2004/0249262 A1 | 12/2004 | Werp | | |
| 2008/0157771 A1* | 7/2008 | Westphal | ........... | G01R 33/3804 |
| | | | | 324/319 |
| 2008/0208036 A1* | 8/2008 | Amies | .................. | A61N 5/1049 |
| | | | | 600/411 |
| 2009/0231073 A1 | 9/2009 | Horisaka | | |

OTHER PUBLICATIONS

International Preliminary Report on Patentability for PCT/US2015/055835, dated Apr. 18, 2017.
International Search Report for PCT/US2015/055835, dated Feb. 1, 2016.
Witten Opinion of the International Searching Authority for PCT/US2015/055835, dated Apr. 18, 2017.

* cited by examiner

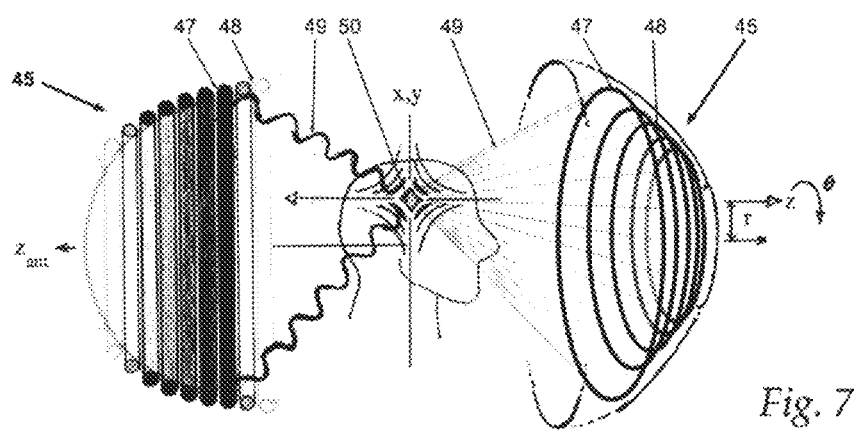
*Fig. 7*
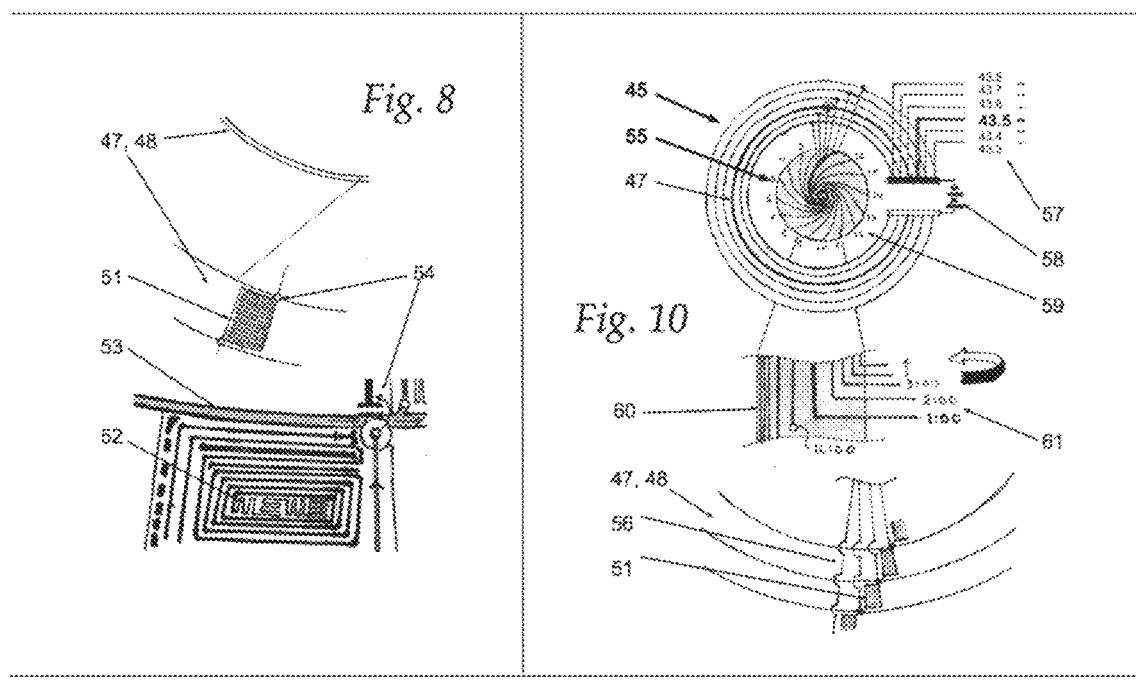
*Fig. 8*
*Fig. 10*
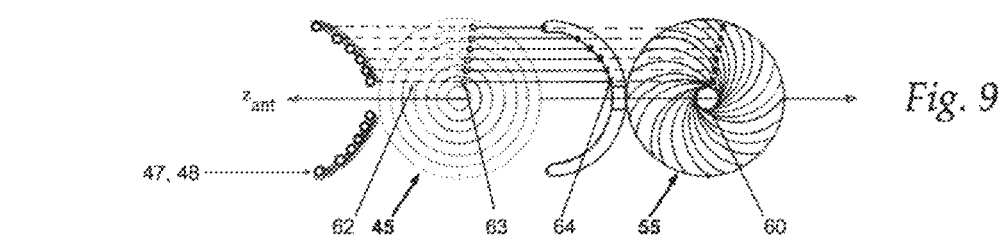
*Fig. 9*

Fig. 14
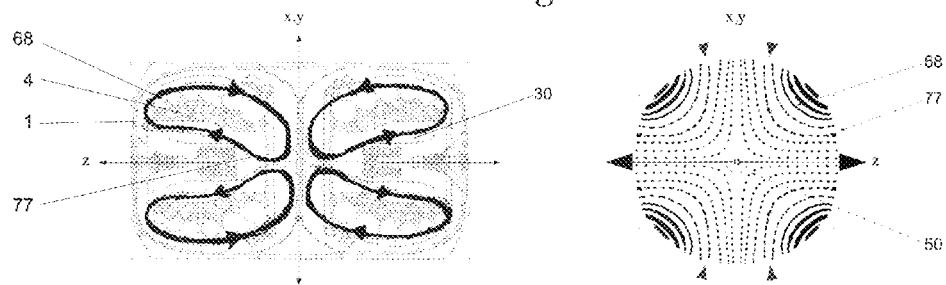
Fig. 15
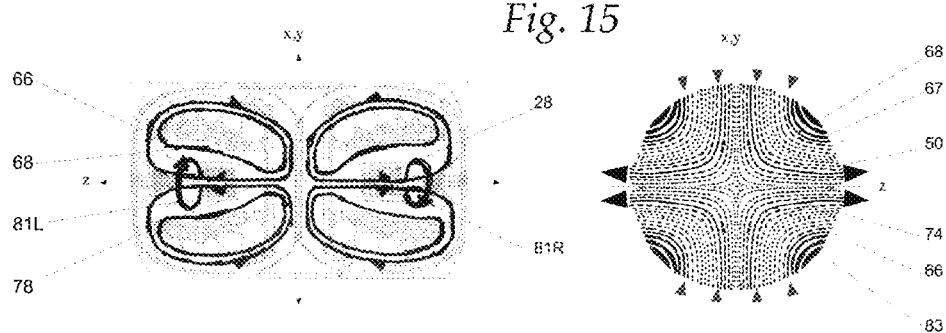
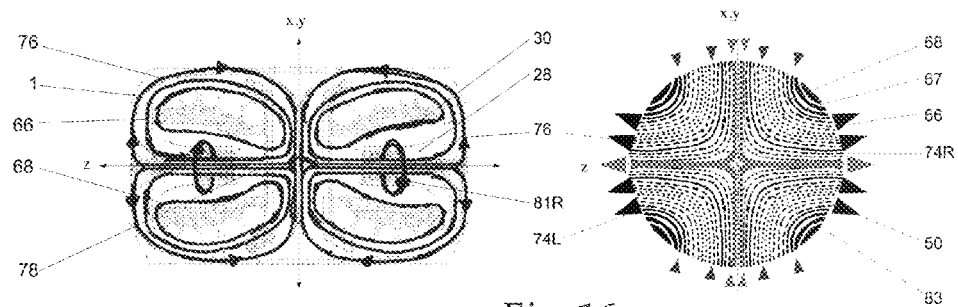
Fig. 16

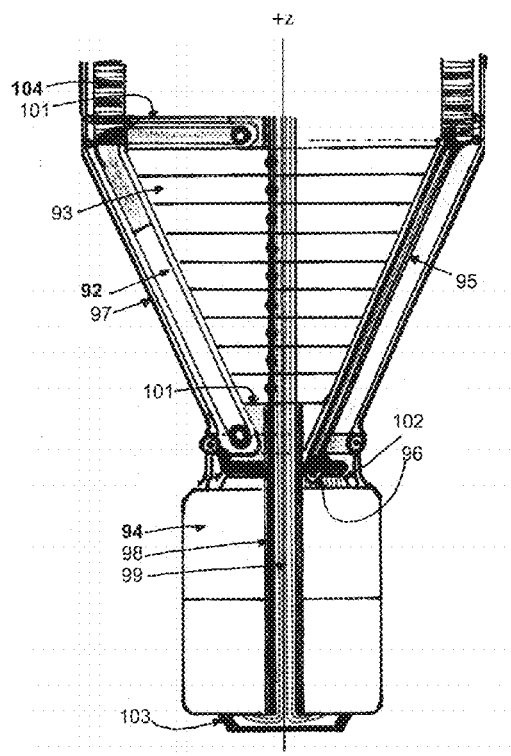
Fig. 24
Fig. 25
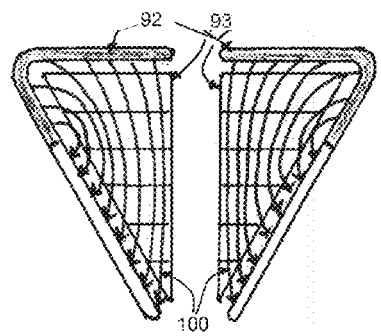
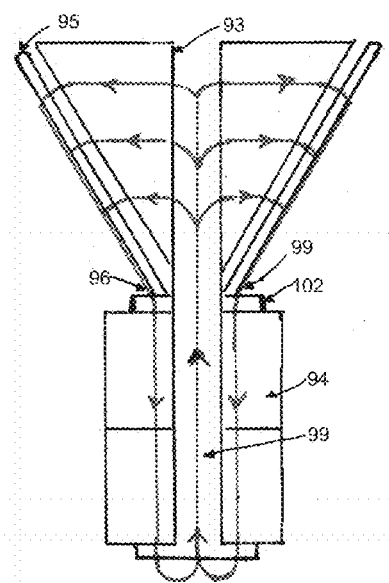
Fig. 26

A

B

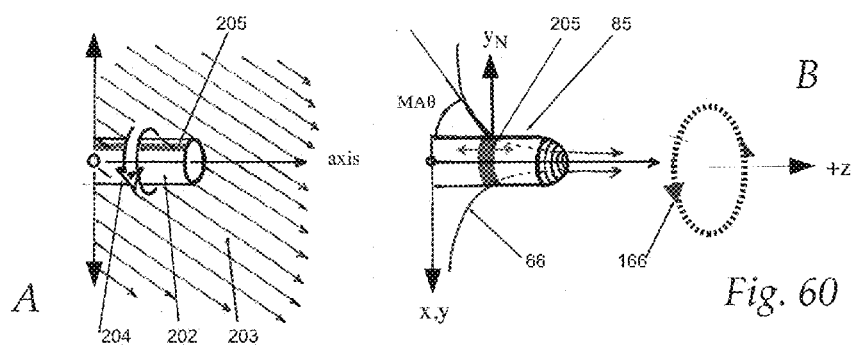
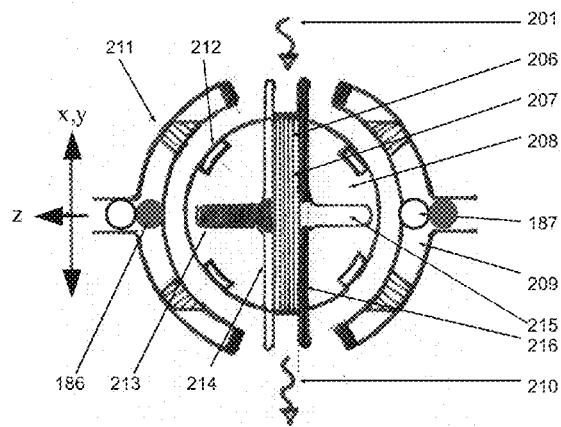
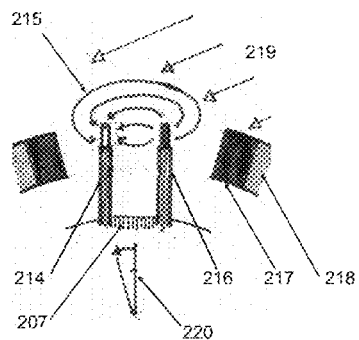
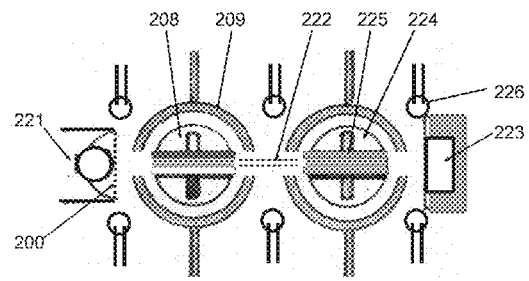
Fig. 60
Fig. 61
Fig. 62
Fig. 63

MAGNETIC FIELD STRUCTURES, FIELD GENERATORS, NAVIGATION AND IMAGING FOR UNTETHERED ROBOTIC DEVICE ENABLED MEDICAL PROCEDURE

RELATED APPLICATIONS INFORMATION

This application claims priority under 35 U.S.C. § 119(e) to U.S. Provisional Patent Application No. 62/064,372, filed Oct. 15, 2014, and titled Magnetic Field Structures, Filed Generators, Navigation and Imaging for Untethered Robotic Device Enabled Medical Procedures which is incorporated herein by reference in its entirety as if set forth in full.

BACKGROUND

1. Technical Field

The embodiments described herein are related to the use of magnetic fields and imaging with respect to medical procedures, and more particularly to robotic magnetic medicine.

2. Related Art

A wide variety of medical procedures are currently performed with undesirable and unavoidable effects on the patient that include damage to healthy tissue during surgery and distribution of therapeutic substances (drugs, antibodies, vaccines and regenerative cells) to sites other than the intended target. Non-disease related surgery increases the risk of sepsis, scarring, blood loss and decreased motor function. Non-specific therapeutic side effects include impacts on metabolic organs and nervous tissue, undesired accumulation in the liver, fatty tissue and digestive tract, and widespread dilution in the circulatory system.

Many of these effects are unavoidable. In most surgical procedures, a cavity must be created through the skin and sub-derma much larger than the actual lesion. In addition, tools, implants and related devices commonly require large tethers, such as the surgeon's hands, catheters, clamps, etc., for manipulation. For most bio-therapeutics, encapsulation, localization and site-specific delivery are limited because related technology is in its infancy. The vast majority of drugs, antibodies and vaccines depend on molecular specificity to accomplish intended functions and minimize side effects. The latter remains non-optimal due to non-specific substance distribution.

Desired effector functions, e.g., removal of a tumor, clearance of a blocked artery, activation of B or T immune cells, antibody tagging of a specific cell type, etc., are relatively well defined. Unfortunately, procedures that accomplish those effector functions also negative impact healthy tissue. In addition, some avoidable or ameliorable diseases remain because procedures to address them result in collateral damage disproportionate to the amount of benefit. The shared causative factor is that medical technology is currently disadvantaged by an inability to limit operator, electro-mechanical, and biochemical procedures to necessary effector functions.

Current options for therapeutics delivery that attempt to maximize targeting and avoid widespread pharmaco-distribution (PD) include magnetic particles, ligand-coated liposomes and antibody coated micro- or nanoscale capsuled drugs. Work on the latter two have been on-going for decades and focus on two main areas: (1) Encapsulation, including containment of payload during transport to target, assurable release of payload to target, reproducible manufacturing and storage life for regulatory purposes, and (2) Surface functionalization, including engineering of antibodies and ligands for maximal specificity, affinity and avidity to targets, maximal shelf life, pH stability and minimal immunogenicity (immune stealth).

Efforts to incorporate magnetic fields with magnetically susceptible bio-therapeutic laden spheres and colloids have focused on accumulation at the site using permanent magnets or electromagnets positioned at the skin proximal to the target site. Interestingly, magnetic particle thermal effects have been researched, including efforts to elicit tissue damage via antibody or ligand coated particles moving rapidly in pulsating magnetic fields.

The majority of these efforts depend on molecular specificity of effector molecules for target proteins. In rare cases, cancer or viral DNA is targeted but these are early stage efforts. In most cases, critical parameters for determining the efficacy of therapeutics are completely out of operator control after application of the therapeutic, including when, where and how much payload was delivered. The pharmacokinetic (PK) question of why an effect or lack thereto occurred often depends on radioactive and other complex and expensive tracing to determine PK/PD.

Even in magnetic, ultrasonic and radio-frequency controlled capsules, conclusions regarding target specification depend on limited biochemical data and broad physical effects, not on the real-time ability to control targeting, application and dosing. In all cases, monitoring of encapsulated payload is not possible except when using magnetic resonance or ultrasonic imaging (MRI, USI) of capsules modified for compatibility with such systems, modifications thereto potentially detrimental to the biotherapeutic payload. Protocols do not yet exist to combine tMRI and USI with both real-time control and accurate targeting of capsules or robotic devices.

More elegant efforts to combine MRI and USI with robotics for drug delivery and surgery include the diverse options of: (1) completely passive or magnetic field-slaved robots having screw or star geometries, and (2) completely autonomous endoscopic devices with on-board computers, propellers, navigation fins, optical cameras and radio-frequency (RF) transmitters. While the latter depend on batteries or, as being researched, RF-based remote energization of on-board power supplies, the former are entirely dependent on external magnetic fields for propulsion. Propulsion-related fields include pulsed attractive or repulsive linear fields, alternating attraction and repulsion gradients produced by orthogonally aligned electromagnetic coils, and rotating fields that impart flagella-like movement. Current endoscopic robots are relatively large and not applicable to vessels and vascular tissue smaller than about 1 cm in diameter. Thus, protocols for cardiovascular, lymphatic and metabolic organs with more narrow vascularization are not possible with current endoscopic robot technology.

In contrast to many medical procedures, dependent technology for medical robots is relatively advanced. Motors, RF transmitters, antennae, microprocessors and even optical detectors can be made on the millimeter [mm] and even micrometer [um] scale. Significant electro-mechanical parameters scale with great linearity from the centimeter [cm] scale, where ubiquitous end products that include servomotors, fans, cameras and mobile phones depend on [mm-um] scale electro-mechanical components. Interest in [mm] scale drone aircraft and gyroscopes, systems also sharing many qualities with ideal medical robots, is high; however, rapid translation of these technologies is hampered by their incompatibility with current MRI and USI systems that only perform diagnosis. Moreover, current MRI technology is incompatible with most robots as well as many implants because of their electrical sensitivity and magnetic susceptibility. Thus, in most cases, diagnosis is maintained separately from therapy.

SUMMARY

Systems and methods for generate magnetic fields (fields) for the positioning and energization of medical devices are described herein.

According to one aspect, a magnetic field generating apparatus comprises two or more co-facing, coaxial magnetic field generators configured to generate equivalent magnetic fields directed toward a symmetrically central convergence plane; a magnetically shielding encasement configured to contain all of the associated magnetic fields generated by the coaxial magnetic field generators; and articulation frames and supports for positioning of the apparatus about a fixed point, wherein the generated magnetic fields are counter-rotated relative to one another.

These and other features, aspects, and embodiments are described below in the section entitled "Detailed Description."

BRIEF DESCRIPTION OF THE DRAWINGS

Features, aspects, and embodiments are described in conjunction with the attached drawings, in which:

FIG. 7 is a diagram illustrating the radial signal acquisition of, and triangulation-based antenna component assignment by, a neurological RF source (MIddle) by the hemispherical antenna array (Right) in accordance with one embodiment.

FIG. 8 describes devices within and component potions of an antenna array ring segment. In increasing magnification (Top to Bottom) are described a portion of the ring segment, an assembly of antenna cells, and a single antenna cell composed of a fractal antenna, base mount, and current leads.

FIG. 9 describes the random attachment of antenna assembly leads on the back of the hemispherical array onto plug mates on the face of a helically wound hemispherical take-up coil base.

FIG. 10 describes correspondence of antenna ring frequency preference with cell assembly lead-wiring onto helical leads on the take-up coil base.

FIG. 14 describes the direction of propagation of static magnetic fields in a simplified version of an apparatus such as in FIG. 1.

FIG. 15 describes the direction of propagation of more highly energized static fields combined with rotating magnetic fields in a simplified apparatus.

FIG. 16 describes the apparatus and fields in FIG. 15 combined with a boundary field from energized tertiary electromagnetic coils.

FIG. 24 describes a homopolar motor drive coil for robotic devices viewed cutaway from the side. Integral thereto are gyroscopic masses and a rechargeable battery.

FIG. 25 describes the homopolar drive coil viewed cutaway from the top along two planes. Rotating gyro-mass and rotor bars are illustrated on the top half.

FIG. 26 describes the direction of magnetic fields generated by homopolar motor rotor bars within the stack of inductive plates (Top), and electric currents along conductive pathways in one direction (Bottom).

FIG. 60 describes a method of MAS/MAT imaging in the presence of a linear magnetic field with axially (z) rotating device (Left), and axially rotating toroidal magnetic field with device (Right).

FIG. 61 describes a LOG device, at middle magnification illustrating the levitation/rotation coils with levitated detector sphere in cross-section.

FIG. 62 describes at highest magnification the LOG equatorial dipole moment leads and proximal levitation/rotation coil components at one equatorial location.

FIG. 63 describes the detector and control gyroscope units with laser source, photodetector and calibration electrodes.

DETAILED DESCRIPTION

Figure 1:
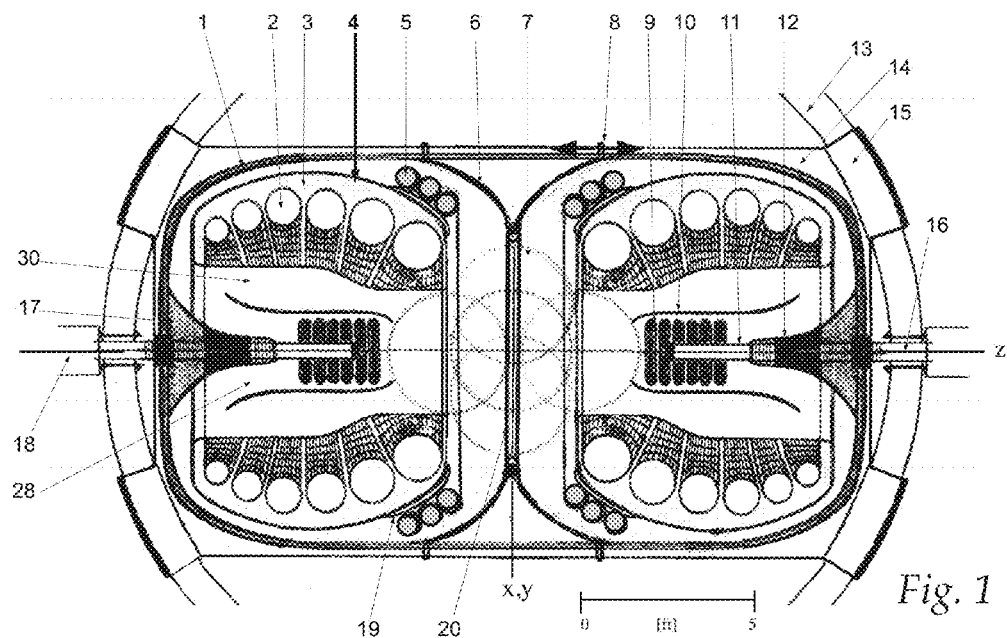
FIG. 1 is a diagram of a diagnostic-therapeutic apparatus comprising two coaxial, co-facing equivalent magnetic field generators disposed about a central therapeutic space large enough to accommodate a person in accordance with one embodiment.

In the embodiments described herein, millimeter-scale multi-functional medical robots can be configured to carry out specific effector functions while at the same time avoiding collateral damage to healthy cells tissue. Untethered, magnetically-levitated devices incorporate surgical tools, payload spaces and real-time functional control and navigation for enhanced medical protocol efficacy with minimal necessary size and ideal robotic geometries. With optimal development, such robots can be navigated to specific tissues and disintegrate tumors by kinetic effect, cavitation or thermal cauterization. Robots can, for example, deliver pharmaco-active drugs, antibodies, vaccines, stem cells, tissue scaffolds and other bio-therapeutics. Further, such robots can clear passages, collect tissue, perform biopsies and deliver the samples to an insertion site for analysis. Such robots can also perform diagnostic, pallative and modulatory functions on electro-active tissue, advancing pain management, neurological analysis and cognitive studies.

MRI, USI, computer aided x-ray tomography (CAT) and other non-invasive techniques are seen as ideal platforms to support more efficacious, effector-focused medical protocols. All of these function by energy input to the body, potentially enabling robot functions. MRI, in particular, is seen as the most promising option with current technology advanced in many ways to accurately diagnose a wide range of diseases with minimal collateral damage. The vast majority of current MRI systems use linear fields generated either (1) in the bores of scanners composed of arrays of cylindrical electromagnetic coils, or (2) between North and South poles of powerful permanent magnets. These systems are well-developed, reliable, accurate, relatively safe and provide benefit to manufacturers, investors, care providers and patients.

Thus, as described herein, MRI technology, or other technologies noted above can be used in conjunction with such robots to perform open-bore imaging and to provide curved and rotating magnetic fields to navigate and energize robots. As explained in detail below, modified electromagnetic coils, magnetic shielding and field gradients can be used to produce magnetic field structures for optimal robot stability, localization, navigation, energization and detection. The use of such MRI technology and robots can enable real-time diagnosis and therapy, providing a truly "theranostic" platform.

It is desirable to: (1) perform surgery in a manner that maximizes destruction of target tissue while minimizing collateral damage to healthy tissue, (2) contain and site specifically release the minimal required amount of pharmacologic drug or antibody to target cells and organs, (3) contain, transport and subsequently release vaccines to germinal centers and other immune tissue to optimize immune system re-programming, and (4) use smaller devices that accomplish these and other effector functions. Ideally, these procedures dispense with a tether, include remote control, remote energization, accurate navigation and real-time imaging. The embodiments described herein can provide such benefits.

Because of the shortcomings of conventional slaved devices, much smaller and also autonomous robots, such as those described herein would be much more desirable. As described below, in various embodiments these, e.g., millimeter size robots also (1) carry on-board analytical, optical and RF devices, (2) be able to navigate complex paths (further provided because of their small size), (3) move through tissue with minimal collateral damage if necessary without need for external, potentially damaging propellers and fins, and (4) be able to carry out surgery and therapeutics delivery. More ideally, the robot can be monitored and navigated in real-time using MRI or USI. Further, the persistence time and spectrum of effector protocols of the robot can be expanded through remote energization.

It is further desirable to perform procedures where medical devices modulate physiological functions in disordered and diseased states. Metabolic disorders that result in ulcers, kidney stones and coronary artery blockages are commonly addressed pharmacologically and surgically. Gastrointestinal tracts are now being mapped by untethered endoscopic robots with cameras, however, kidney stones are still being shattered with ultrasonic transmitters and blocked coronary arteries are still being enlarged, but not cleared, with catheter delivered balloons or rotating blades. The latter procedures require pushing a long tether through urinary or venous tracts to deliver a comparatively large effector tool to the therapeutic site. But with the systems and methods described herein, a small-as-possible tool can be delivered untethered and monitored in real-time, to carry out the necessary procedure. Relatedly, it is possible to biopsy a potential cancerous tissue in a similarly non-invasive manner.

The MRI-compatible robotics described herein provide levels of robustness, reproducibility and versatility that pass regulatory qualification as medical devices and implants, with impact to the patient that is proportionally limited to effector functions.

In certain embodiments, diagnosis and therapy are combined into a unitary procedure, with the robot contributing to both. Thankfully, a wide variety of magnetic field structures can be generated, including those more suitable to robotic device power systems. Ideally, these magnetic field structures also enable MRI imaging. In this vein, it may not be necessary to rely on linear fields. Clinically approved MRI of any kind depends on (1) target proton, nucleus or magnetic resonance imaging contrast agent (MRICA) resonance in a strong linear magnetic field (B0), (2) energization of targets with a secondary electromagnetic field (B1), and (3) measurement of RF energy output during relaxation of targets back to the resonant equilibrium state.

In certain embodiments, these operations, and subsequent spatial encoding and image reconstruction, are carried out using other types of MRI scanners that produce magnetic field structures that are compatible with robotic devices.

It is desired that MRI-compatible robotics be developed, at levels of robustness, reproducibility and versatility that pass regulatory qualification as medical devices and implants, ideally with impact to the patient that is proportionally limited to effector functions.

A wide range of neurological disorders are attributable to either insufficient or excessive electrical activity, including Parkinson's, Dementia, Epilepsy, Chronic Pain and the disease spectra of Post Traumatic Stress Disorder (PTSD). The efficacy of procedures that address these disorders, including deep brain stimulation (DBS), trans-cranial magnetic stimulation (TMS), surgery, pharmacologics and regenerative cells is being determined. In certain embodiments, discreet portions of the central and peripheral nervous systems can be analyzed to identify problematic ganglia, which are then electrically modulated to improve cognitive and motor functions. If necessary, delicate surgery can be performed to remove and replace sub-optimal target tissue, again using untethered and real-time controlled devices as described herein.

Certain embodiments described herein comprise apparatuses that generate magnetic fields (fields) for the positioning and energization of medical devices. Such embodiments can further comprise or make use of magnetic field structures, heretofore defined as one or more magnetic field geometries, gradients, potentials, and elements or layers commonly illustrated by magnetic field lines. Such field structures can include rotating, compressive, constrictive and torsion fields compatible with the robotic devices described herein. Radio-frequency (RF) transmission and reception devices compatible with field generators and field structures are provided. Methods and apparatuses are provided for field structure modulation using focusing shields, coil geometries, generator articulation and other types of modulations. Methods are also provided for robotic device-based diagnostic, therapeutic, prophylactic and cybernetic function. Additionally provided are novel magnetic resonance imaging (MRI) methods in reference frames and analysis volumes (voxels) compatible with components, robots and field structures produced in the invention.

Certain embodiments include an apparatus having components comprised of electromagnetic coils having uniform or varying radius. These main coils generate strong (~1-9 Tesla [T]) and generally invariant field gradients in apparatus bores herein referred to as static or main fields. Static fields can be applied to facilitate robotic control, spatial encoding and signal acquisition in voxels outside bores. A plurality of main coils generate toroidal field structures characteristic of Helmholtz, Maxwell, Tesla, Rodin, Solenoid and other electromagnetic coil types.

Certain embodiments can also comprise a second set of physically revolving electromagnetic components that generate and focus rotating field elements peripheral to and concentric with static fields. Revolving permanent magnets, conductive components and electromagnetic coils add general rotational quality and distinct rotating field elements to ensemble magnetic fields, facilitate larger gradients in main coil bores and assist in synonymous motile field propagation within shielded enclosures. Revolving field structures enable robotic device navigation, translocation, and imaging strategies.

In certain embodiments, a tertiary set of non-rotating coils are provided to generate boundary fields for partitioning of rotating field elements produced by secondary coil sets. Tertiary coils are disposed peripheral to all other field coils, partitioned by shielding, and produce the outermost field elements within an apparatus. Boundary fields can vary through energization and coil positioning, either dynamically to enable pulsed MRI imaging of therapeutic space or discreetly to enable stable positioning and energization of robotic devices. Tertiary coils also generate rotating magnetic fields through application of alternating current (AC) through helically-wound conduction pathways.

Also disclosed are magnetic shielding encasements and partitions. Shields of low magnetic field susceptibility and transparency of significant mechanical integrity confine fields within the apparatus, present geometries that focus field energies onto desired targets, and disposed to partition autonomous field elements and physically support field coils. Also provided is fine [mm scale] field focusing in the patient through alignment and articulation of field generators, and selective energization of secondary, tertiary and peripheral field coils.

When integrated into encasements, a coaxial assembly of all components associated with main coils, revolving secondary coils, fixed tertiary coils and field focusing encasements define a field generator (generator). Support equipment including cryogenics, RF transmitters, antennae, and other components and devices are understood to be integral in field generators.

A plurality of field generators can be disposed and energized to generate converging (co-facing) toroidal magnetic fields. Disposition is either coaxial along a common bore axis [z, per convention] in the case of two field generators, or at equivalent angles to shared axes (orthogonal disposition) when three or more field generators are applied. Magnetic fields can be generated and focused into higher flux densities toward a convergence plane disposed midway between field generators.

Patient tables are also disclosed that can be used with the systems and methods described herein to provide a diagnostic/therapeutic platform. Size, geometry and disposition of main coils create an outside bore therapeutic space where the patient can stand, lay down or be seated. Bed and chair components should be MRI compatible, i.e., passively or actively magnetically transparent. Patient contacting magnetic field focusing helmets or body units can be integrated.

Because of their magnetic qualities, robotic devices and certain payloads can provide tangental function as magnetic resonance imaging contrast agents (MRICA). In some embodiments the devices alter either the main magnetic (B0) or transverse RF (B1) field to improve signal acquisition in the vicinity of the device, particularly in aspects where field intensities below current clinical MRI art and proximal to the robot exist. In related embodiments, devices generate magnetic fields to achieve similar goals. In additional embodiments, devices generate RF signals, for example matching the Larmor frequency of nearby resonant targets or soluble MRICA.

In certain embodiments, signal acquisition and spatial encoding for real-time analysis of the device-proximal therapeutic space is provided. Briefly, in contrast to conventional MRI applications, which useeither (1) generally linear intrabore fields in in apparatuses using cryogenic electromagnets, or (2) generally linear fields between North and South poles in apparatuses using strong permanent magnets, the systems and methods described herein provide rotating, radial, curvilinear and null field geometries, often of dynamic quality, and disposed outside main coil bores. Signals acquisition of resonant target relaxation after B1 stimulation can be provided in non-linear and transient geometries.

A coaxial disposition of main, revolving and non-revolving electromagnetic coils all energized in the same direction produce an ensemble toroidal magnetic field. For description, terminology of elements and layers is used herein to describe geographically distinct field structures propagating within a generator, and in a manner preserving element autonomy as illustrated by closed field lines. Terminology and illustrations are not meant to contradict convention, which establishes that physical separation of field elements by shields and other components creates geographically distinct structures originating proportionally, but not distinctly, from field elements generated in those partitioned volumes.

Secondary and tertiary electromagnetic coils as briefly described above can present varied field strengths, rotational speeds, electrical modulation (amplitudes, frequencies and wave patterns), spatial position and other variable parameters. Secondary and tertiary coils can also be moved along a common axis (z) or at an azimuth (θ) to main coils.

Integrated can be revolving or immobile magnetic shields and lenses providing both bulk focusing of field energies within enclosures and subtle focusing of fields on an outside bore target. In all, non-cryogenic electromagnetic components provide for and modulate (1) overall ensemble field strength, (2) the magnitude and dynamic qualities of rotating magnetic field elements, specifically their geometries, relative potentials and rotational rates, (3) the stability of structures generated by converging rotating fields, and the (4) positions, structures and persistence of torsional fields which are used to position and energize robotic devices.

Field elements generated by main coils are understood to remain confined within each field generator and not interact with static fields produced by other field generators as such interaction may interfere with imaging capabilities. Also, static fields do not productively interact with robotic devices. Strong static gradients are provided to compress and focus rotating and boundary fields around a small (~1 cm3) toroidal pocket. In most cases, two mirror image counter rotating fields and boundary envelope field(s) converge to produce closely disposed counter-rotating elements. Due to main coil compression, rotating fields are focused close (+/−5 mm) to the magnetic pocket. Because the toroidal pocket is in most cases the location of a robotic device, terminology of magnetic pocket, magnetic trap and null volume are used interchangeably. Null terminology does not imply any absence of fluxes or potentials except at the central point (0,0,0), by convention.

An array of RF transmitters generating a wide spectrum of frequencies can image a relatively large volume around a magnetic pocket. Such RF transmitters contribute transverse fields (B1). RF signals generated by relaxation of energized protons or nuclei can be acquired through radial antenna arrays, and mounted on the main coils similar to conventional MRI practice. The antenna array can be wide spectrum sensitive, composed of a large plurality of concentric rings with identical micron scale fractal antenna units (cells). The array can be programmed by applying different voltages to each array ring resulting in cells with distinctive frequency and modulation sensitives.

Determination of an RF source geographical position can be performed through acquisition by all similarly energized cells, however at different times (except with axially disposed sources), enabling conical geometry triangulation. Acquisition by cells in adjacent rings is less efficient and output signals are distinct from cells in the perfectly modulated ring. The antenna array can be mounted on a take-up coil base that harvests magnetic energy from main coils to avoid requirement of an external power source. Base leads from each cell can be wound in a toroidal manner to increase current travel distance for greater signal discrimination.

Complexity in attaching a large number of cell leads (~1,000,000) to their correct plugs on the base is avoided by random attachment. An assembled antenna array is then programmed for spatial discrimination by moving a pinging multi-frequency RF source while different voltages are applied to each ring and signals are processed to correlate RF source location and frequency with spatial processing. This method allows each antenna cell to be assigned a unique frequency, modulation and spatial coordinate set. When used for imaging, k-space data sets can match each cell signal and its optimal modulation with input data acquired in radial coordinates to determine the frequency and location of signal source. As practiced in the art, final signal processing can be carried out by Fourier Transform to reconstruct the image.

In certain embodiments, two exactly similar field generators disposed coaxially with co-facing positive bores are used, where all coils immobilized and energized to generate equally balanced fields, mirror image non-rotating blended (MINRB) fields are produced. The outermost field elements from each generator combine into a unitary structure at a central plane at circular coordinates defining a convergence ring, producing a two dimensional (2D) field of radially symmetric potential and geometry directed inward towards the central point with flux density the sum of outermost field elements. Un-blending back into distinct fields occurs around the central point in a toroidal manner with divergence location at circular coordinates defining a divergence ring. Field elements then propagate back into generators and into either main, secondary or tertiary coil sets depending on shielding and encasement geometries. In this comparative aspect, field potentials are constant at all locations in the apparatus and have no angularity when viewed from an axial reference.

Similarly, in certain embodiments two exactly similar field generators disposed coaxially with co-facing positive bores are used, where all coils equally energized and motile coils revolving at the same rate to generate equally balanced fields, mirror image counter rotating blending (MICRB) fields are produced. As in MINRB fields, outermost elements blend into a 2D field at convergence, diverge back into distinct elements, and the convergence plane does not rotate. Importantly, the non-rotating blended field cannot be maintained indefinitely because motile electromagnetic components generating those elements continue to revolve. Rotation-induced gradient between rotating and non-rotating field elements and magnetic torque induced on field coils increase with increasing angular displacement. Produced in the vicinity of the convergence plane are (1) 3D radial structures that transition between completely blended and non-blended qualities, and (2) torque imposed on both field generators and proximal magnetically susceptible compounds or devices, including robots.

Highly structured and regulated magnetic torque can be used proximal to the null space to position and energize robotic devices. Terminology of torque is herein also used to describe rotating field potentials that induced rotational force on revolving magnetically susceptible assemblies. Energization and motility of field generator components is performed in a cooperative manner that maintains the synonymous quality of the ensemble field, i.e., by creation of magnetic field structures that minimize acute angularity in field vectors and avoid rapid changes in localized field potentials—in particular, the cutting of magnetic field lines that can generate RF signals that interfere with MRI and robotic functions. Robotic effector protocols are also understood to be performed in a synonymous manner.

Alternatively, revolving coils can provide more dynamic MICRB structures characterized by rapid transitions between a non-rotating 2D blended disk and rotating 3D structures along and close to the convergence plane. Produced are radial magnetic pockets composed of formerly blended elements that rapidly un-blend to recover synonymy with revolving components and resume low field densities before extinguishing back into blended field structures. Structures are torqued in the direction of coil revolution, mirror image counter rotate about the central plane and can be described as two sets of diametrically opposed passerelles. The various field structures described herein are collectively referred to as a dynamic gradient pocket (DGP).

At low gradients, blending/un-blending events can occur outside the divergence ring and preserve the toroidal pocket;

however, transitions between a 2D converged plane and 3D radially directed and rotationally torqued null spaces can result in structural fluctuations that occur at the rate of blending/un-blending transitions, heretofore referred to as the DGP pulse frequency. Critical factors determining the DGP pulse frequency include overall ensemble field strength and motile coils revolution rate. Generation of DGP structures with high DGP pulse frequencies are provided by rapid coil revolution rates, large current loads and rapidly oscillating high voltage currents.

Related but tangental to this aspect, counter rotating equally energized coils that revolve at different speeds are expected to produce at the central plane sharply angled field vectors and rapidly changing potentials. Such asymmetric MICRB fields will blend and un-blend in an asynchronous manner resulting in non-synchronic DGP pulses, and non-uniformly distributed torqued radial null zones producing non-flat convergence planes.

In the absence of or when main coil energies are minimal, diverged formerly blended MICRB fields will form a large null space of similar scale as the bore radius. Compressive magnetic energy may be absent, and constrictive magnetic energy and the DGP pulse frequency may be low. Thus, little usable magnetic torque or diametrically opposed force is provided for robotic devices. To overcome this deficiency, high DGP pulse frequencies can be provided by, for example, rapid coil revolution rates and high frequency currents in motile coils; however, ensemble gradients will remain low unless revolving components generate field densities approaching those of cryogenic coils. This will compress the null space but is unsustainable.

An additional benefit of performing simultaneous MRI-based diagnosis and control of robotic devices provided by strong main coils is lost. Preferably, compression by static fields tightly focuses the divergence ring into a ~8-10 mm diameter circle and compresses a ~64-125 mm3 toroidal pocket. Axial locations of torsion fields, where counter rotating elements can provide rotational magnetic torque, are thus only ~10-16 mm apart along the z-axis or roughly the same scale as robots.

In the continuing aspect of MICRB fields, robotic device or assembly of magnetically-susceptible objects, as described herein, placed centrally in the null zone will experience diametrically opposed expansive and contractive forces at the DGP pulse frequency in addition to dynamic counter-rotating constrictive forces. A plurality of non-diamagnetic, magnetically-susceptible particles (1) substantially smaller than the 64-125 mm3 toroidal pocket, (2) loosely contained in an enclosing matrix or other field transparent container, and (3) disposed centrally will be moved in two equal populations in a linear manner along the z-axis away from and then back towards the pocket at the DGP pulse frequency, in addition to being moved in counter rotating directions.

A portion of the magnetic particles will remain relatively immobilized in the low flux zone during each DGP pulse event, exchanging locations with the larger population. If using a homogenous population of spherical super-paramagnetic particles of aforementioned scale and density whereby particle mean free path provides 1-on-1 interaction at a given AC frequency in secondary coils, the invention also provides dipole-dipole coupling of particles facilitated by field-induced transient magnetic moments in particles, resulting in generally uniform intra-particle spacing.

In certain other embodiments, two exactly similar field generators disposed coaxially with co-facing positive bores and all coils, including boundary coils, energized and equally rotated to produce equal fields are user, where mirror image counter rotating separated (MICRS) fields are generated. This can be an ideal field structure for robotic device management. Again, rotating elements from each ensemble field propagate synonymously with revolving electromagnetic components, herein in a manner that re-synchronizes field vectors with motile components to maximize induced magnetic torque on robots while minimizing torque on field generator coils. Synonymy also compensates for (1) potential losses and field harvest by robotic devices, (2) gradients relative to less than transparent surfaces, (3) interaction with non-parallel or unequal fields, and (4) other phenomena that negatively impact the linearity of field vectors and torsional geometry.

In contrast to MICRB, MICRS fields provide several operational advantages. First, because rotating field elements are maintained as distinct structures, convergence of counter rotating elements does not occur. Induced torque on revolving coils is reduced by approximately 50% preserving ensemble field synonymy and reducing field vector angularity, field line cutting and RF noise. If the boundary field was also rotated synchronously with the secondary field, the secondary coils would experience no induced torque during boundary field rotation. Secondly, because the null space becomes compressed with each boundary coil pulse contributing flux, magnetic torque on robots increases. Of note, as revolving secondary coils can also act as boundary coils and generate pulsed fields, distinction between non-cryogenic coils generating pulsed rotating outermost field elements in a field generator is de-emphasized. Thirdly, the probability of contaminating main coil field elements by their counterpart(s) approaches zero as main/compressive elements must overcome two sets of secondary/rotating and tertiary/boundary elements. Additionally, DGP structures are reduced in both gradient and pulse frequency as counter-rotating fields (1) no longer interact, if a constant boundary field, or two counter-rotating boundary fields undulating in phase, is used as the partition or (2) interact less often, if a pulsed boundary field is used.

In certain embodiments, rotational magnetic torque for the navigation and energization of robotic devices can be provided. Rotating field gradients exist in field generators between (1) rotating and non-rotating fields, (2) rotating fields and low magnetic susceptibility surfaces, (3) field layers rotating at different speeds, and (4) rotating fields and magnetically-susceptible particles, assemblies and revolving components on robotic devices. Outside the null space from the divergence ring to the points of conical peaks, field intensity and rotational speed increase with increasing distance (n) from the central point (0,0,0). Conical radii decrease and magnetic fields beyond these points assume greater linearity and rotational speed matching that of revolving components. The difference in field intensities and rotational speeds between the central target (zero flux and no provided torque) and the two coaxial con-facing conical termini (maximal flux and maximal torque) result in two magnetic torsion fields. Terminology of torsion is used herein to emphasize a combination of (1) diametrically opposed attractive (pulling) forces, (2) diametrically opposed compressive forces, mainly due to main coil gradients, (3) diametrically opposed constrictive (twisting) forces produced by revolving electromagnetic coils and/or boundary coils powered by AC current that provide (4) rotational torque for magnetically susceptible objects.

It is understood that no magnetic flux exists at the central target per convention but that weak, non-zero potentials exist at every point (x,y,z or z, θ, r>0), even inside the null space; however these can be neglected. Priority can be given to the geometrical and functional relationship between the null zone and an assembly of particles or a mechanical robot having magnetic susceptibility specifically optimized for function in torsion fields as previously defined. Therefore, free field zone (FFZ) is heretofore used to describe the volume (1) encompassing the central target point, (2) bound by the divergence ring (x,y plane), and (3) two coordinates along the common axis where field intensities and rotational torque are sufficient to overcome the activation threshold of magnetic drive coils on a robotic device (z+/−AT). These two points are generally, but not exclusively, locations of torsion fields. Terminology is dependent only on the target point, which in many aspects describes the preferred coordinates of a robotic device, and the geometry and activation thresholds of robot drive coils, which varies for different devices and applications.

In certain embodiments a relatively large FFZ is provided that can immobilize a smaller robot or a robot having a higher activation threshold within a space that provides insufficient navigational and functional energy. The same FFZ will activate a larger robot having drive coils that extend further outward into higher magnetic flux space, or a smaller robot having a lower activation threshold. FFZ per se is dependent mainly on device qualities and not limited to field characteristics. It does not depend on the flux density, if any, in a null or other space which the FFZ encompasses or the actual location of torsion fields.

Because a null volume is disposed between two confacing, coaxial counter rotating torsion fields in the continuing aspect, a symmetric and diametrically opposed magnetic potential is produced in the FFZ along the common axis from non-zero field intensity ($z=-n$), to no field at the target point ($x,y,z=0$), to an equivalent non-zero potential ($z=+n$). Also evident is that a non-zero magnetic potential exists from the target point (0,0,0) outward along the convergence plane (x,y) to radial points of divergence (y, r=D). These potential gradients and field structures provide a novel experimental condition having useful qualities. Briefly, it is understood in the art that regions of very high magnetic potential are applicable to electronics, the physical and materials sciences particularly micro and nano-electromechanical systems (MEMS/NEMS).

Regions of very high magnetic potential, in some applications counter rotating fields, in certain applications diametrically opposed constricting fields, in specific applications symmetrical torsion fields in the millimeter scale or below can be used in the life sciences to influence susceptible metabolic, biochemical or electro-active processes. In many of these applications, biomolecule dipole moments (native, induced, and generally ensemble in large molecules), biopolymer and charged membrane magnetic susceptibilities, electric potentials and electron flow determine viable function.

Further, high potentials and geometries provided in the embodiments described herein influence chemical processes, particularly those at interfaces of magnetic particles, polymers and solvents where molecules, substances and surfaces possess charge, conductance or magnetic susceptibility. Overall, FFZ structures provided in the invention can be used to manipulate biological, chemical and physical processes. In short, focused high intensity and dynamic counter rotating torsion fields provide both a novel environment and useful analytical tool for a wide range of investigations.

It is understood that magnetic pockets or null spaces can localize diamagnetic materials, minimizing their energy states. Similarly understood in the art, paramagnetic, ferromagnetic and ferrimagnetic materials will tend to accumulate near torsion fields and other constricting magnetic field zones and driven beyond into higher flux zones, in the continuing aspect along the common axis ($z>|n|$). Materials having magnetic dipole moments will tend to align their vectors with proximal field lines. Because torsion fields herein rotate, materials will also tend to revolve or otherwise change position with the fields. Further, materials with gyroscopic qualities will tend to rotate at the same speed as the fields to achieve equilibrium, and with dipole moments aligned to minimize their potential energy. Further still in the continuing aspect, two equivalent magnetic gyroscopic assemblies of the same scale as torsion fields will tend to remain stably positioned thereto if they are rigidly or flexibly tethered to each other along a common axis.

In certain embodiments, stable positioning and energization of a robotic device having coaxial counter-rotating magnetic drive coils with revolving gyroscopic components is provided. Magnetically susceptible components will be attracted in diametrically opposite directions along the common axis (z) and revolve synonymously with rotating field gradients if allowed to interact with potentials significantly above activation thresholds. If geometrically symmetric and constrictive, field gradients produce stable torsion fields that provide rotational torque to device drive coils. It can be preferred that torsion fields sufficiently activate but not overwhelm drive coils, specifically neither too strong or rapid that electro-mechanical magnetic components on robots are challenged beyond their operational limits.

In the continuing aspect of embodiments that use MICRS fields, an axially and radially symmetric FFZ is created and sized such that rotating field elements at each constriction zone are disposed closely to revolving magnetically-susceptible components on device drive coils. Activation thresholds, load limits, power efficiencies and other terminology understood in the art apply to all motors with revolving components. In aspects where robots are kept inactive, FFZ geometry and characteristics can be such that torsion fields are maintained outside device drive coils and/or field rotation rates are kept low. In aspects where robots are kept hyper-active or when on-board batteries require regeneration, FFZ can be structured such that torsion fields are within drive coil spaces and also rotate rapidly.

In embodiments where robots must be navigated with precision and simultaneously carry out an effector function requiring high energies such as in ablative surgery, the sizing and energization of FFZ for maximal constrictive potential on drive coils, while also moving the FFZ to provide device navigation, is provided.

Absence of field rotation, rotation in only one direction and/or insufficient rotational rate, even in the presence of equal and diverging fields as in the aspect of MINRB fields, are understood to be inadequate for stable device positioning due to insufficient induction of gyroscopic effect. Such meta-stable conditions create the tendency for a device to escape from a FFZ and, in the MINRB aspect, be propelled in either axial direction. This instability is significant in conventional applications that use linear or non-torsional rotating magnetic fields to position and propel magnetically susceptible objects. In some conventional solutions, position escape is avoided by rapid pulsing of generally linear but non-rotating or inadequately rotating fields. Alternatively, a larger plurality (>2) of field generators or field coils can be symmetrically disposed in relative orthogonality to a target and produce less intense fields.

Thus, the embodiments described here that use two co-facing field generators and disclosed method of producing balanced counter rotating fields that radially converge, orthogonally diverge and create symmetrical, con-facing torsion fields in an axially balanced robotic device that is disposed in a magnetic null zone can present a significant improvement over conventional solutions. AS do the disclosed magnetic assemblies having two balanced counter-rotating magnetic inertial gyroscopes which also function are robotic positioning and energization coils.

Navigation of robotic devices is provided herein by selective energization of field coils and electromagnetic components thereto. In some cases, unequal energization and rotational rate of coaxial coil sets in different field generators enable dominance of one coil set in positioning of a robotic device along a common axis resulting in device translocation along the axis towards the dominant coil set. In the same or other cases, it is understood that cryogenic main coils may be de-energized to enable fields produced by secondary and peripheral field coils to overcome those produced in the other field generator to achieve the aforementioned asymmetry. Thereto, when real-time high resolution imaging of the proximal space around the robot is less important than device navigation, the invention provides positioning and translocation of a robotic device at orthogonal axes using only weak, i.e., generally non-compressive, constrictive and torsional fields.

It is understood that the patient will have undergone a standard, high resolution MRI prior to implant of robotic device and that significant un-changing geographic details of the therapeutic space will have been determined. Tissues thereto provide non real-time, however useful 3D landmarks for robot navigation which, in the continuing cases, can include bone, other high density tissue or implanted MRICA pellets location-secured with bio-adhesive.

Robot navigation can also be provided by repositioning of one or more field generators, for example along the z-axis to maintain preferred co-axial disposition. Briefly, one field generator can be kept immobile and the other moved closer or further from the other field generator resulting in trans-location of the FFZ. Repositioning of generators at an azimuth to a shared axis can also be performed. In combination with selective energization of main coils other coils, FFZ structure can be maintained while also being moved along any axis depending on apparatus structural and functional limitations and the presence of patient bed or chair mounts that can limit apparatus articulation.

In general, robot navigation is provided by keeping the patient immobile and repositioning field generators that maintain relative position, moving the FFZ along desired paths through the use of concentric articulation frames. Disposition of field generators in this preferred aspect allows the patient to remain comfortable in the therapeutic space while the field generators are articulated along yaw, pitch and roll axes. Similarly, the patient bed can be moved along the z-axis, elevated (y) and shifted (x) to accomplish similar functions.

Real-time imaging of the robotic device space can be performed by transient energization of non-cryogenic coils to field densities in the FFZ vicinity that approach that of commonly performed imaging. For example, 1.0 T fields generated by combined energies from revolving and boundary coils along all axes enables acquisition of 43.5 MHz signal from water protons at conical coordinates about the null space. Robotic devices can be navigated and effector functions performed herein; however the FFZ torsion fields must be sufficiently strong to overcome device activation thresholds implying large field gradients to achieve both robot function and target imaging at 1.0 T close to the device. Brief resonant bursts as in pulsed MRI, ultra-short time echo imaging (USTEI) and other technology can be used. For example, high resolution imaging in a pulsed or strobe-like manner of the immediate robotic space can be carried out secondary and tertiary coil sets to intensities approaching 1 T.

Robotic drive coil magnetically susceptible components have geometries that provide electromagnetic motor function. Returning to the aspect of a balanced and symmetrical FFZ as in MICRS fields, coaxial and counter-rotating fields enable remote energization of on-board batteries contributing to robot autonomy. Drive coil AT can be diverse as is well understood. Therefore, FFZ and torsion fields can be provided as greatly variable and dynamic in size, magnetic potential, geometry symmetry and rotational speed. Provided in devices are a spectra of drive coil activation thresholds that vary with robot status, effector function and surrounding media. It is understood that activation thresholds will be higher in media such as bone versus soft tissue due to greater resistance to drilling, coring and other functions requiring greater induced torque from torsion fields.

For aspects such as neurological or neonatal monitoring, it is understood that robots will have contained, unexposed drive coils minimizing collateral tissue damage. For the purposes of stable positioning, trapping and robot recharging, the invention provides methods to tune and modulate FFZ so that torsion fields produce magnetic torque that either (1) remains below, (2) achieves or (3) surpasses robot drive coil activation thresholds.

Robotic drive coils can be simple and robust assemblies of homopolar motors and single or dual phase rotor-stator motors that are straight-forward to fabricate at device scales (~1×3 mm), mass produce, create industrial standards and validate as integral components of medical devices, probes and implants for regulatory and quality control purposes. Homopolar motors can provide efficient generation of current for charging on-board batteries or capacitors in aspects where FFZ are modulated to provide excess energies for applications requiring rapid current release such as pain modulation and tumor cavitation. Low phase motors can provide optimal efficiency of converting battery voltage to rotation of exposed components that contribute to device propulsion, such as fins for applications such as endoscopic diagnosis and screws for applications such as calcified tissue ablation.

Drive coils include a plurality of magnetically susceptible rotor components having radially balanced dipole moments directed away from device center. The latter is generally both the robot's central axis and the field generator bore axis (z). These magnetic rotor bars are assembled such that dipole moments are in dis-equilibrium to, and a group magnetic moment persists even in the absence of, an external magnetic field. The group dipole moment of each drive coil is generally curvilinear and directed in axial directions away from the FFZ. In most cases, devices have bow and stern drive coils with the same activation threshold to maximize stable positioning in an axially symmetric FFZ where the robot center is disposed at the central point and the drive coils at torsion fields. In the aspect of rotor bars as permanent dipole magnetic wires or rods, positive poles are directed to the bow and stern of each robot and angled at an azimuth to the negative poles. In the aspect of super-paramagnetic wire or particles encased in a bent tubular shell, a similar geometry can be utilized. In both aspects, when a torsional or rotating linear magnetic field is applied, device positioning along a common axis is provided by the tendency—never achieved—of each rotor bar or rotor tube to align its dipole moment vector in parallel with the applied field. Minimal group dipole moment in each drive coil is only achieved when (1) the entire drive coil aligns in parallel to the applied field, rotating in the case of torsion fields, and (2) bow and stern drive coils are disposed in opposite directions, counter rotating in the case of FFZ torsion fields.

In summary, because drive coils have (i) dipole moments minimized only when aligned in group parallel to a magnetic field, (ii) gyroscopic inertial masses which revolve with rotating fields, and (iii) function as both electromagnetic generators and tools or analytical devices, (1) robot position stability, (2) navigation and (3) remote energization are provided.

In embodiments where homopolar motors are utilized, acutely angled (<90 deg) magnetic rotor bars form a nearly triangular geometry that produces an axially directed, generally linear internal magnetic field upon rotation of bars. Linear fields are ideal for generation of an electric field in the homopolar motor's inductive metal disc pile for current production in applications such as capacitor charging. If desired, rapid rotation of rotor bar set is provided by current discharge from a capacitor or current release from a battery to the inductor pile, resulting in generation of a rotating magnetic field. Homopolar motors operating in this reverse mode are acknowledged to generate gyroscopic effect less efficiently than rotor-stator motors.

In embodiments where rotor-stator motors are used, obtusely angled (>90 deg) magnetic rotor bars form a cylindrical-conical geometry that, upon rotation, produces a radial internal magnetic field directed to (1) a inner core magnet, hollow and centrally insulated to house electrical leads, and (2) a high ferrite content mantle, facilitating radial orthogonality of the internal field. Longitudinally wound conducting wire provides generation of an electric field to recharge on-board batteries in one current direction. Rotation of rotor bars is provided in the other current direction with a charged battery, even in the absence of a rotating external field, facilitating device propulsion in autonomous mode. Autonomous navigation is provided when robot components include biochemical or electro-optical sensors. Screws, propellers, flagellum, adaptive geometries such as tails and other propulsive components integral to exposed rotors contribute to navigation.

Torsion fields provide on board battery recharging through induced rotation of rotor bars. Inactive devices will tend to remain immobilized during such recharging sessions so long as the FFZ is symmetrical, immobile, stable, persistent and torsion fields provide magnetic torques beyond that of drive coil activation thresholds; however, recharging can occur during device translocation and therapeutic protocols in a motile FFZ if induced torque and subsequent rotor bar set rotational speed overcomes battery drainage as the robot performs its functions. In cases such as ablative surgery, tissue evisceration and other highly kinetic effector procedures, it is understood that torsion fields will have to be applied regularly and intensively to the robot to insure both accurate device navigation and maintain energy levels of on-board components.

Both homopolar and rotor-stator motors can be attached to batteries, capacitors, computer control, RF, optical and other components to accomplish a wide variety of functions. Homopolar motors are sealed inside device shells or capsules due to exposed conductive elements and electrically conducting and lubricating fluid. Stators are similarly contained, however rotors can be exposed without sacrificing recharge or navigation function at adequate activation thresholds and exposed rotors further provide navigation and effector tool functions.

Within a given robot, both activation threshold and gyroscopic effect can be balanced for drive coils at the bow and stern. Alternative thereto being a bias in an asymmetric drive coil robot for navigation towards one axial direction of a symmetric FFZ. Similarly, the same robot can maintain position in an asymmetric FFZ, as is produced when one field generator is energized and/or rotationally distinct from the other.

Homopolar and rotor-stator motors can be attached to integrally rotating inertial masses providing additional gyroscopic benefit. In many embodiments, rotating components free float relative to immobile components but are contained within shells or conical geometries and positive poles of rotor bars are disposed at greater distances from attachment points near rotational axes; however, because of the small overall length (~12 mm) and radius (~3 mm) of each robot, rotating coil bars are relatively light in mass (~1 mg each), thus inadequate to provide stabilizing gyroscopic effect unless rotated at very high speeds (~3000 rpm).

Inertial gyro-mass free operation requires very high field intensities and revolving coil rotational speeds, shortening operational life of both field generators and robot drive coils. Optimal gyroscopic effect and stable robotic positioning are provided by rotating at low-to-medium speeds (~60-240 rpm) a relatively heavy inertial mass (~50-100 mg) in each drive coil. Gyro-masses can be non-functional rings, disks, hemispheres or function as batteries, sensors and conductive elements. In embodiments where rotating gyro-masses are exposed, they can be surgical, tissue sampling or ablative tools. In embodiments where a gyro-mass is a delivered or acquired payload, drive coils may adapt to altered activation thresholds and devices may adapt to changing center of mass or center of magnetic balance.

In embodiments where autonomous robot function is undesired or in applications where only slaved devices have clinical approval, device drive coils can dispense with energy generation or charge carrying capacity and be simple assemblies of magnetizable wire or bars plus rotating gyro-masses, linearly or azimuthally angled with the torsion field. This passive configuration retains the benefit of positioning stability and navigation through the torsion fields of a FFZ.

A variety of robotic device configurations can be provided. A cylindrical hull (for optimal passage through tissue with minimal drag coefficient, CD) with two AT-balanced gyro-magnetic drive coils disposed close to device termini and with payload volume in the middle form the basic template. Diverse operational parameters include robot size, mass, center of balance, drive coil AT, energy load and the number, thickness, angle and length of rotor bars. Devices can carry one or two homopolar, rotor-stator or passive motors, or any combination thereto and dispose a spectrum of components, devices, payloads, payload volumes, effector and navigation tools.

In some embodiments, devices carry charge measurement and RF devices to serve as implants for monitoring and reporting neurological activity. Sensors, stents, electrodes and other current in art devices which accomplish these functions will require modification for compatibility with drive coil power systems and to fit into robots. In other aspects, larger robots may carry optical devices to analyze the therapeutic space and supplement MRI-based positioning of the robot, as applicable in robot semi-autonomous mode where some operator control exists and when signal acquisition in or proximal to the FFZ is either infeasible or undesired.

In other embodiments, robots fitted with two rotor-stator drive coils have a drill, auger or boring tool attached at one end for biopsy or evisceration of tumors, fibrous and infected tissue. Disposed on the rotor at the other end could be fins, propellers or screws for navigation.

In still other embodiments, passive coils carry a central payload of chemotherapeutic drug, antibody, vaccine or regenerative cells directly to a tumor site, germinal center or lesion. The payload is released when the drive coils compress or pull apart, shattering the payload capsule. Also provided is a device geometry comprising a two-part shelled capsule and elastic wires that contain the robot termini after payload release and facilitate re-assembly back into a closed unit.

In yet other embodiments, a robotic device mounts passive hollow-core drive coils with substantially straight rotor bars. Alignment tendency with an applied field is preserved however longer rotor bars with greater individual dipole moments are required to achieve positioning stability approaching angled bars. Benefit provided is that these drive coils permit passage of biological substances through drive coil centers and robotic space. In one specific embodiments, the bow drive coil mounts a drill and chipping blades, and is connected by an elastic tube to a hollow stern drive coil. Attached to the latter is a flexible tube which terminates in a sieve for collection of dis-aggregated tissue while allowing passage of fluid and very small particles. This aspect and device configuration provides ability to perform clearance of vasculature as in coronary artery disease.

Further provided for the vascular clearance aspects are dynamic FFZ that enable robot translocation through non-linear and constrictive paths within veins and arteries. Benefit is provided when the mean linear path of a vascular bottleneck is shorter than the overall length of the robot (including tubular tether and collection bag), locale where arterial blockages and calcified tissue frequently occur. The asymmetric expansion/compression quality of the tether provides a peristaltic action which hydraulically pumps dis-aggregated tissue towards the stern. Force is provided when FFZ torsion fields are expanded and contracted as when boundary fields are pulsed to generate inflation and compression waves which move (+/−z) the location foci of FFZ torsion fields. Robot length thus changes depending on path limits while navigation is provided as before by movement and articulation of field generators. Collection bag is kept slack to maneuver around obstacles. When full, the robot is navigated back to the insertion or another point.

An abbreviated version of this embodiment provides capability to perform biopsies. If tissue dis-aggregation is undesired, bow drive coils can mount a hollow boring tool to enable collection of a cylindrical plug of tissue in the robot's center volume. The rear drive coil may still need to mount a sieve or filter to equalize hydraulic pressure. Fluid and small particles may be eliminated thusly or through more centrally disposed pores. Related to this aspect, viable tissue may be chemically preserved in the robot immediately after harvest with fixative released into the payload space after elimination of excess fluid and closure of ejection ports.

In a related embodiment, retractable abrasion or chipping blades can be used to clear vascular blockages from robots having adaptive geometry. Robots can navigate to the pre-thrombotic site in coronary arteries then, preferably upon reception of an operator RF signal, increased FFZ energies can pull bow and stern hull sections apart, extending tools from storage volumes in hull midsections. Coring or chipping in counter-rotating directions maintains robot positioning stability, particularly in how volumetric flow rate conditions, and helps accumulate dis-engaged plaque deposits into a centrally disposed waste bag if necessary.

To minimize collateral tissue damage, robot navigation to target location from insertion site avoids nervous and highly vascularized tissue. Briefly, FFZ are generated as small as possible and the trapped robot translocated with precision in paths previously determined in a high resolution MRI scan from the location of insertion to the therapeutic target. During translocation, pulsed MRI data acquired in torsional reference frames provide real-time navigation. Kinetic tools are preferably mounted on the robot stern with the bow being a low CD hydrophobic and oleo-phobic surface. In a case of ablative surgery with potential thermal and cavitation effects, upon arrival at the tumor, necrotic or other target tissue, the robot can execute a 180 degree turn to direct the stern end surgical tool towards the target.

A therapeutic protocol can be carried out by movement of the FFZ into and out of the target with the robot drilling-out tissue in its path, entry/exit locations changed until all of the target tissue is disaggregated. The robot can be retrieved by following the entry path bow forward without the need for another 180 degree maneuver.

Specifically provided are adaptive geometry devices where portions of robots alter their magnetic susceptibility. In one embodiment, a solenoid pump, electromagnetic piston or shape memory polymer is activated by RF signal from an operator or on-board algorithm to extend device drive coils out from a magnetically non-susceptible housing. This is provided by (1) a bow or stern extension of a previously hidden drive coil out into the therapeutic space, and (2) movement of a drive coil from a magnetically shielded to a transparent section of the hull. In this aspect, a device can assume magnetic stealth mode and remain immobile even in the presence of a high external field such as in 1.0-3.0 T brain scans with linear B0 fields.

Also specifically provided are adaptive geometry robotic devices that release or unravel non-insulated wires that are attached to high voltage capacitors for use as surgical tools in applications such as thermo-ablation of tumors or micro-surgery cauterization. After translocation of the implanted robot to a lesion site, operator RF signal, on-board algorithm or expanded torsion fields separate bow and stern hull sections, unraveling an conductive tether wire. Through FFZ movement and device translocation, the extended robot can move the stiffened wire in a carving or slicing manner through the entire tumor. Energy for thermal effect can be provided by on-board batteries and capacitors until exhaustion, or replenished for the life of the coils through torsion fields. After completion of effector function, the wire can be reeled back into the robot.

Additionally provided are coordinated function of sequential robots. In one embodiment, an adaptive geometry robot can navigate to a healthy nerve bundle or to damaged nerves and mount a signal-modulating sensor on a ganglion via bio-adhesive. Attached to the sensor is an insulated wire having on the other end a conductive terminus and small bio-adhesive capsule. The robot can attach the cybernetic device and unravel the wire along a predetermined path. Upon completion of this segment, an RF signal or current can shatter the capsule releasing the bio-adhesive at the distal end forming a semi-permanent mount. Follow-up robots can attach successive series of connectors, adhesive mounted plugs and entire devices to create a cybernetic network. The network can terminate in either a skin port for direct connection to ex vivo equipment or an implanted device having RF functions. Robotic implants positioned at intersections provide ability to report on ganglionic functions at different locations within the network. Provision is made for stimulating specific network locations through activation/deactivation of devices.

The cybernetic skin port can also serve as a robot dock for implantation, retrieval and maintenance of robotic devices. The dock comprises housing for the robot, electrodes for re-generation of device batteries, provision for retrieval of tissue samples, and application of successive robots to the patient with reduced puncturing or injections. The dock can be semi-permanent as in the case of brain tumors and traumatic stress injury requiring long term care, a plurality of different procedures, cognitive monitoring and brain reconstruction. Components include a blunted large gauge MRI-compatible needle partially filled with flexible polymer to help seal the robot in its dock. The inner needle end partially encloses the robot bow. The outer end is sealed to the patient skull with strong bio-adhesive and capped with a screw-top for device insertion and retrieval. An aseptic port facilitates device retrieval and replacement. The port can be inserted in other body locations, single use or semi-permanent. The robot sheath can also be field transparent if FFZ-based re-energization of the robot while in its dock is desired.

MRI-based imaging at a distance from field generator bores can also be provided. Certain embodiments provide distal magnetic resonance through apparatus components that include variable radii main coils wound in a non-linear manner concentrically about the (z-axis). Specifically, conductive wire, bars or other current carrying paths for cryogenically cooled electromagnetic coils are disposed with greater density and decreasing inner coil radii in the positive direction facing towards other generators similarly disposed in an apparatus. This variable radii constrictive geometry coil sets and shielding encasements focus and compress generated fields. Coil segment wire can be wound on frames and cores as common in the art but with segments fitting together to produce the overall geometry. Energization of all coil segments to direct a field in the target direction results in large field intensities at a distance, specifically outside the bore, when combined with shielding encasements.

A standard in art MRI scanner can modified with revolving coils, other electromechanical and algorithmic components, and shielding to serve as a field generator in an un-preferred aspect. The scanner can be coaxially mated with an variable coil radii field generator to create a combination diagnostic/therapeutic apparatus that utilizes very similar in the art MRI-based software and imaging technology. In short, the patient could undergo a standard MRI scan, then be moved out of that bore and into the plane of convergence with an invention field generator. Injection of a robotic device, creation of a FFZ around the device and invention imaging and robot effector function could then commence. Conceptually, two or more standard MRI scanners can be used to generate a distal resonant field; however, because standard scanners are optimized to produce maximal field intensities in their bores, significant re-engineering would be necessary to produce both imaging and robot control out of bore. Intra-bore device trapping, navigation and energization is not possible due to the linear, unidirectional nature of the static field (B0) and the absence of counter-rotating torsion fields. Counter rotating secondary fields (B1) cannot adequately provide power for robot navigation and energization. The latter would also be extremely limited even if a FFZ and torsion fields could be created—as would be the case with two MRI scanners disposed co-facing in close proximity—due to limited ability to reposition and articulate the scanners, and vary and pulse their generated fields.

A variety of methods are provided to spatially encode water protons, resonant nuclei or MRICA in the immediate robotic space (within 1 cm) and acquire relaxation RF signal for image reconstruction. These methods can be optimized for the apparatus components, functional capabilities and limits described herein as well as the described diagnostic/therapeutic methods carried and magnetic field structures. These methods can also be compatible with other MRI-based technologies.

In certain embodiment, rapidly rotating and intense field pulses are generated in co-facing in MICRB and MICRS fields. In an exemplary 100 ms secondary coil pulse, elements peripheral to main fields increase by 1000-fold producing a transient 1 T layer within 1 cm of a robot. Rapid rotation of motile coils and/or sudden large AC amplitudes axially rotates the field pulse and shifts the net magnetic potential of susceptible nuclei from the toroidal direction (ZTOR) to the new direction of net magnetization (ZROT). Fields intersecting robot drive coils increase 1000-fold to their device activation limit, specifically, 1 cm from the robot/target center, the former 1 Gauss [G] field line generated by main coils increases to 1000 G/0.1 T. This intensity of field enables transient energization, resonance, spatial encoding, relaxation and image reconstruction using novel MRI-based resonance and signaling technology.

In certain embodiments, to analyze points having similar net magnetization azimuths to the laboratory plane (z) and disposed on the toroidal surface of the transient 1 T field line (one on each side of the pulse-energized FFZ), MRI is carried out distinctly from standard art MRI. Briefly, a transverse B1 pulse ($+\pi/2$) oscillating at 43.5 MHz is directed to the FFZ as common in the art; however, a transverse spin lock pulse (SLP) is then applied to lock the net magnetization of spatially distinct protons into the transverse plane (MTV). The SLP is applied at the Larmor frequency ($\omega 1000$ G), oscillated in phase, on resonance and is linearly polarized.

Because net magnetizations are directed toroidally and not linearly, only protons having transverse vectors parallel to the applied SLP become spin locked. This is unlike standard MRI where all protons similarly resonated by a uniformly linear B0 and cohered by an orthogonal B1 are simultaneously spin locked because their transverse magnetizations are all parallel to one another.

After application, the SLP is then rotated to bring the transverse magnetization of rotated and spin locked protons (MROT) parallel with the original net magnetization vector of weak protons (MTOR). Both the pulse gradient and polarized spin lock pulse (PSLP) are then terminated simultaneously. Magnetization vectors are allowed to collapse from a strong (1000 G) magnetization in the direction of rotation (ZROT) with comitant strong PSLP-normalized transverse signal, to a weak magnetization in the equilibrium toroidal direction at 1 G (ZTOR). The relaxation of (1) formerly spin locked planar 1000 G magnetizations and (2) formerly angled longitudinal 1000 G magnetizations, into a 1 G longitudinal vector has aspects of both spin-lattice (T1) and spin-spin (T2) relaxation. Herein named pseudo T1 T2 provides imaging of weak fields characteristic of the FFZ around a robotic device, compatible with rotating pulsed fields.

In the transverse plane, the abrupt termination of a strong rotating field results in the net magnetization quickly losing transverse quality and a rapid T2 signal is produced as net magnetization directions equilibrate into toroidal alignment. Also, in the brief interim between termination of B1 and maximal SLP amplitude, some loss of magnetization transverse to ZROT occurs and a brief pre-T2 relaxation signal can be acquired. Alternatively, the transverse RF signal can be modulated with the SLP to blend both signals (RFIN) as the oscillation changes from transverse ($\omega$TV) to spin-lock ($\omega$SL). In pseudoT1 T2, longitudinal effects also contribute to transverse relaxation phenomena and resultant signals (RFOUT).

In the longitudinal plane, the abrupt termination of the SLP that is plane-locked to the low energy magnetization vector produces unique relaxation profiles distinct from classic T1. Spin unlocking allows generally planar vectors to re-align longitudinally back to ZTOR. However, pulse termination also results in tilted vectors withdrawing back into 1 G net magnetization. This reverse T1 (rT1) thus occurs both longitudinally and transversely with the latter contributing to the T2 component of the overall pseudo T1 T2 spectrum. Lastly, a relatively minor contribution from high energy spins previously pointing in the (−ZROT) direction are expected to generate a classic T1 signal, i.e., relaxation back into the positive direction of the longitudinal axis (+ZTOR).

This return to equilibrium is not as quickly reflected in secondary and boundary coils due to remanence. However, to ensure that gradients return to nearly their equilibrium levels within 0.1 sec, selected pulse coil materials and engineering, cryogenic cooling (if necessary), control algorithms, coil localization and non-transparent magnetic shutters can be employed to maximize field intensities, abruptness of both field pulses, RF signal initiation and termination.

Of note, adiabatic conditions are maintained since the Larmor frequencies are much higher than the anticipated maximal induced rotational rate of the transient pulse (3000 rpm). Also, because the PSLP brings transverse magnetizations parallel to adiabatic equilibrium, a second RF pulse (−$\pi$/2) to restore locked magnetizations (MSL) back into the longitudinal direction (ZTOR) may not be necessary. In the absence of stimulatory RF signal, adiabatic conditions direct re-equilibrium of proton magnetizations back to levels determined only by the static field ($\omega$1 G). The resulting slow but high gradient relaxation is anticipated to improve signaling contrast at low field levels (~1-100 G) as a plurality of target protons relax in diverse ways in the pseudo T1 T2 profile.

Spatial encoding is provided by the specificity of the SLP transmitter's frequency, oscillation, modulation and position for transverse magnetization spins that are resonating at a specific frequency and aligned parallel to the applied signal. In an exemplary of the continuing aspect, a polarized SLP locks onto parallel MTV at points on the 1 T toroidal surfaces directly above the bow ventral (+V, 1 T) and stern dorsal (−D, 1 T) sides of a robot for subsequent rotation and pseudo T1 T2 signal collection. In contrast, SLP pulse initiation will have a detrimental effect on 1 T points directly to the left and right of the robot, i.e., the bow starboard (+S, 1 T) and stern port (−P, 1 T), because their magnetizations are 90 degrees off-set. The initial SLP directed to V and D are parallel to the ZROT of points P and S and, because of SLP frequency and modulation, will briefly de-resonate the protons therein until the SLP is rotated away from ZROT(−P, 1 T) and ZROT(+S, 1 T). However, the RSLP will eventually align parallel to the now recovered protons at points P and S and pseudo T1 T2 therein can be carried out. Similarly, for all other points pulse resonated at 1 T, the RSLP will enable pseudo T1 T2 imaging as the SLP transmitter matches polarization with transverse magnetizations at those points.

A similar strategy can be carried out for all other points along the 1 T toroidal surface and for all other points of higher and lower field intensity by variation of RSLP frequency, polarization, positioning (if modulation is mechanical versus electronic) and other parameters.

It is understood that magnetically susceptible components of robots, particularly rotor bars in drive coils, will distort the toroidal magnetic geometry in and around the FFZ. Distortion can be both positive, in aspects where drive coils generate their own magnetic fields as with permanent dipole magnetic bars, or negative, in aspects where net negative fields are produced when super paramagnetic components attract field elements. Drive coil options can also include current carrying wires that generate fields at selective times, geometries and intensities. In one aspect, AC propagates towards both device termini to generate counter rotating magnetic fields describing bulbous or knob geometries. Whichever drive coil option is used, the resulting field distortion and change in net magnetization angle can be taken into account during imaging.

In an embodiment, the robot can carry RF transmitters to accomplish a wide variety of functions that can include (1) direct location indicator, or pinging, by the device, (2) RF transmission at Larmor frequencies of resonant targets in the therapeutic space, (3) proximal RF signal modulation to enhance apparatus RF imaging of targets, by constructive or destructive interference, (4) direct RF imaging of targets resonated by magnetic field generating components of robots.

In another embodiment, a form of magic angle spinning (MAS) can be applied to image spatial locations where rotating field elements intersect the robot at the MA of 54.7 degrees. Because of toroidal geometry, few elements interact with the robot at or near this angle. In addition, both rotating fields and device drive coils are anticipated to revolve at rates (~60-300 rpm) much lower than ideal MAS speeds. Thus, application of magic angle turning (MAT) pulse sequences modulated for resonant frequencies intersecting the robot about 54.7 degrees (MA+/−5 degrees) can more comprehensively apply MAS to the invention. To supplement this effort and contribute to other device functions, a micro-gyroscope can be carried as payload, placed in the device at the intended location of field elements intersecting at ~54.7 degrees, and spun more rapidly than either motile portions of drive coils or rotating apparatus magnetic fields. An even number of counter rotating micro-gyroscopes will provide device stabilization even in the absence of a FFZ.

In another embodiment, the robotic payload can include a laser optical gyroscope (LOG) to measure discreet (uT) brain magnetic fields. The unit is completely insulated in axial directions, i.e., from the magnetic field of device drive coils and on-board devices. In one embodiment, the LOG is a rotating quartz sphere with an equatorial disk composed of (1) polarized crystal or bonded micron scale crystal sheets, (2) coaxial disks with polar-to-equatorial directed magnetic dipole moments in the uT range, and (3) circumpolar disks that that resist an induced electric current. The described detection sphere acts as a levitated gyroscope and is disposed between two enclosing drive coils which free-float the sphere and induce rotation as well understood in the art. Disposed at 180 opposed equatorial locations, respectively, are a polarized laser and photomultiplier chip. The rotating, levitated sphere and laser components function as a LOG as understood in the art.

The internal dipole elements can extend equatorially outward to create two latitudinal disks of opposite polarity. Upon rotation, the polarized equatorial extensions generate a small, rotating magnetic field (BD). Any uT range potential (BO) impacting orthogonally (x,y) to the extensions will cause the sphere to tilt its rotational axis and mis-align the polarized equatorial crystal from perfect alignment with the polarized laser beam, creating a detectable precession. The detector sphere is mated to a control unit functioning simultaneously and identical in all aspects except that it lacks an internal dipole moment and corrects for purely mechanical fluctuations.

Symmetric Field Generator

Referring now to FIG. 1, in a preferred embodiment, an apparatus comprises two exactly similar field generators, coaxial, co-facing and all coils energized to generate equivalent magnetic fields directed toward a symmetrically central convergence plane heretofore defined as the x,y-axis that evenly divides the therapeutic space (7) provided for a patient. Within each field generator is set of main coils (4) being cryogenically-cooled superconducting electromagnetic field-generating apparatuses that produce up to 9.0 T of field intensity in the therapeutic space. Main coils include all coolant (3), electrical, insulating and structural systems clearly understood and commonly applied in the art of cryogenic/superconducting-type MRI scanners and are included herein in their entirety by reference. Cryogenic coils (2) have varying radii, reducing in the central direction to focus field energies toward fields produced by the other generator.

Also provided for convergent focusing of fields is a central curvilinear surface of magnetic field non-transparent and deflective shielding (6) having geometry resembling the null space between two toroids with circular apex being the convergence plane. An RF transmitter array (20) for MRI-related scanning is preferably disposed around the convergence plane. Disposed at extremities of the field generators are concentric magnetic shields (17) resembling the axial null space of a toroid. Heretofore, terminology of toroid and toroidal are used generously to describe both apparatuses and magnetic fields sharing this geometric template. A magnetic shield (1) continuous with both the central (6) and terminal (12) shields encloses both field generators and contains all generated fields within the apparatus.

Disposed intra-bore of each main coil are a second set of revolving electromagnetic coils (9) which produce the rotating elements of an ensemble magnetic field within a generator. Concentric with secondary coils are magnetic shielding (10) and revolving magnetized rods (11) that further focus rotating field elements within intra-bore spaces (28) toroidally peripheral to the spaces (30) occupied by non-rotating static fields. Focusing rods are attached to axial drive shafts (16) through rotating non-transparent toroidal and conical fittings (12). An additional set of non-revolving concentric tertiary coils (5) are disposed peripheral to all other coils and partitioned from the main coils by a layer of magnetic shielding (19). The central convergent shielding (6) can be moved axially (+/−z) to distort or translocate the magnetic pocket produced in the center of the convergence plane.

Between the sliding surfaces thereto (8) is a groove opening to allow a bed or chair post for the patient. The entire apparatus can axially articulate approximately four feet and approximately two feet up, down, left and right (+/−x,y), enabling the patient to remain immobile while the magnetic pocket is translocated. The entire apparatus is mounted through rollers (15) and a frame (14) to a circular articulation rail (13) providing 360 degrees of roll (z-axis) and yaw (y-axis) articulation of the apparatus about the geographical center of the therapeutic space (7). Coordinate convention used herein are the z-axis being common bore axis, up/down is the y-axis, and left/right for the patient and in/out of the illustration plane the x-axis. Approximately 30 degrees of pitch (+/−15 degrees, x-axis) articulation is provided, i.e., the limit of articulation defined by the grooved opening or the bed/chair post relative to the main or tertiary coil surfaces closest to the therapeutic space. The apparatus articulation frame mounts drive shafts (16) extending out from encasement (1), and drive motors (28) for revolution of secondary electromagnetic components, enabling generation of rotating magnetic fields in any apparatus orientation.

Generous apparatus articulation and freedom of movement provides the ability to move robotic devices in the generated magnetic pocket at the center of the produced convergence plane with linear distance (2-4 feet) and azimuth (30 degrees). Greatly stable generation of static fields (B0) by main coils, and greatly synonymous generation of rotating (BROT) and boundary fields by secondary and tertiary coils provides for a highly stable magnetic pocket with proviso for energizing robotic devices. Therefore, preferred effector methods carried out in the Symmetric Field Generator include magnetic tumor and tissue ablation and robotic delivery of therapeutics including pharmaceuticals, antibodies and vaccines.

Asymmetric Field Generator

Figure 2:
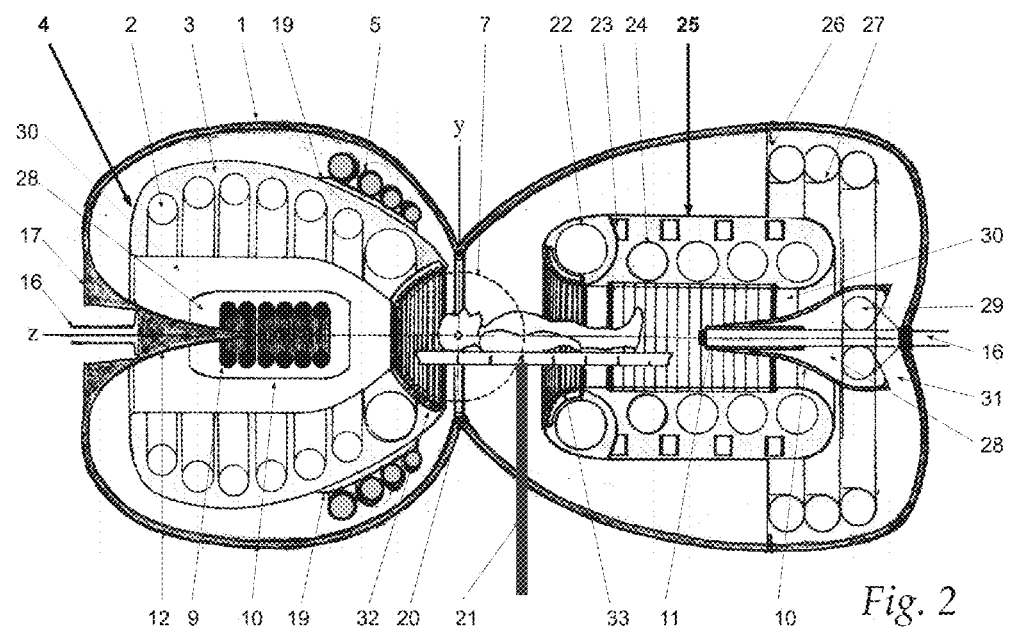
FIG. 2 is a diagram illustrating a neurological diagnostic-therapeutic apparatus comprising two coaxial, co-facing field generators disposed about a central therapeutic space in accordance with one embodiment.

Referring now to FIG. 2, in another preferred embodiment, an apparatus comprises two dis-similar field generators, however similar to the apparatus in FIG. 1 in that Asymmetric Field Generators are coaxial, co-facing and energized with equivalent magnetic fields directed toward a central convergence plane (x,y-axis) dividing the therapeutic space (7). One field generator can be a more powerful version of a generators from FIG. 1, including larger main (4), additional revolving secondary (9) and additional immobile tertiary (5) coils. An RF antenna array (32) is provided for wide-band acquisition of MRI-based relaxation signals. It is understood but not illustrated that a similar RF antenna array exists on one or both field generators in FIG. 1.

The other field generator in the Asymmetric aspect can be a common in the art MRI scanner, modified for inclusion in the invention in a novel fashion. Referring now to the Right field generator in FIG. 2, is an MRI scanner (25) with coil sub-set on the therapeutic end having enhanced field generating capacity (22), standard in practice field coils (24), and gradient coils (23) modified and disposed for both intra-bore and extra-bore field modulation. Disposed intra-bore and concentric with all coils in the Left generator are a revolving secondary field generating and field focusing coil set composed of a coil (29), concentric magnetized rod (11) and toroidal geometry shielding (10) collectively mounted to an axial drive shaft (16). This secondary coil set revolves synonymously with a tertiary set of rotating coils of greater radii (27) disposed substantially to the rear/terminus of the modified MRI scanner field generator. Larger tertiary field coils can physically revolve to produce rotating elements of the ensemble field within the Right generator, or be immobile and generate rotating field elements via conduction of AC current through pathways directed a helical manner as understood in the magnetics art. In a preferred enablement, the tertiary coils are affixed to, and revolve concurrently with, the secondary coil set.

Magnetic field elements produced by secondary and tertiary coils (BROT) pass through the volume inside the secondary shielding (28) and process through the wider rear opening peripheral to elements generated by main coils (B0) which process away from the central plane in the space between the secondary shielding and the inner bore (30). In a preferred enablement, net field intensities and rotating field rotational rates equal those produced in the Left generator.

Disposed substantially within the bore of the Right field generator is a patient bed supported by a post (21) positioned between the left (32) and right (33) RF antenna arrays. The bed can slide a distance limited by the spacing of the RF arrays, approximately three feet, or along internal bed rails on a fixed post. Approximately 10 degrees of pitch (+/−5 degrees) and somewhat less yaw is provided by freedom of relative movement of the bed within the Right field generator's main coil bore. 360 degrees of roll are provided, however, in a preferred enablement, the Asymmetric Field Generator apparatus lacks an articulation frame and corresponding rails. Translocation of a robotic device within a magnetic pocket is provided by relative energization of secondary and tertiary coils in each field generator, and discreet (<1 foot) x,y,z-axial and azimuthal movement of the patient through the bed, particularly in neurological applications.

A standard in the art MRI scan can be performed with the Asymmetric Field Generator and is a preferred method in preparation for theranostic procedures utilizing this aspect. The apparatus magnetic shielding encasement can open a the separation (26) substantially at the rear of the Right generator, and also at the convergence intersection between field generators shown in FIG. 2 as the location of the RF transmitter array (20). After the secondary and tertiary field coils are removed, the modified MRI scanner (25) remains. Re-assembly of the Asymmetric Field Generator can be carried out by reversing the process.

In comparison to the Symmetric Field Generator, provided in this aspect are (1) increased field intensities, (2) enhanced RF signal acquisition and (3) greater rotating field strength in both generators (substantially much greater in the Right generator). Thus, in a preferred enablement, the Asymmetric Field Generator is used to carry out methods requiring smaller robots that translocate limited distances (<1 foot), with delicate navigation (azimuths of 0.1 mm) and prioritize regeneration of smaller on-board power systems over mechanical effect of exposed gyroscopic tools. Protocols thereto include robotic clearance of vascular blockages and the placement and energization of cybernetic and neuromuscular pathways components in electro-active tissues, including the use of robotic devices as electric and magnetic field modulating implants.

Field Coil Geometry and RF Antenna Arrays

Referring now to FIGS. 3-6, conductive wire, cable, disk or other current pathway component (37) is preferably wound in the manner illustrated wherein pathways are linear when viewed from the orthogonal reference (36) but are wound curvilinearly producing a decreasing coil radii in direction of the therapeutic space (to the Right). Individual pathway components can have variable radii, e.g., wire of differing thicknesses, to produce curvilinear geometries. Wire bases (38) and frames (39) that, respectively, support distinctive layers and sections of wound wire can likewise describe curvilinear geometries for ease of construction, and to create fin-shaped (40) coil units (FIG. 4) that interconnect to form a continuous or gap-free (FIG. 5) curvilinear main coil set.

Figure 3:
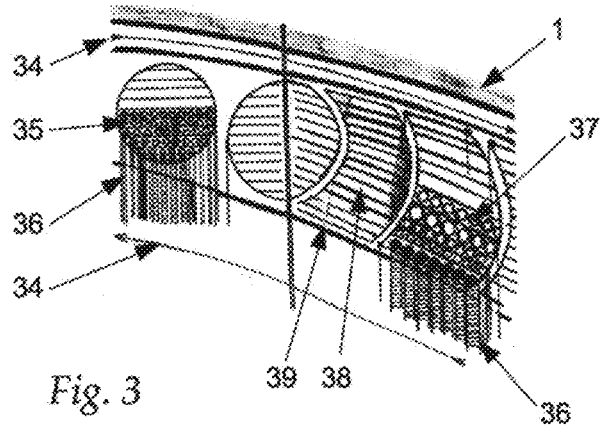
FIG. 3 is a diagram illustrating main coil electromagnetic components of the apparatus of FIGS. 1 and 2 in greater detail.
Figure 5:
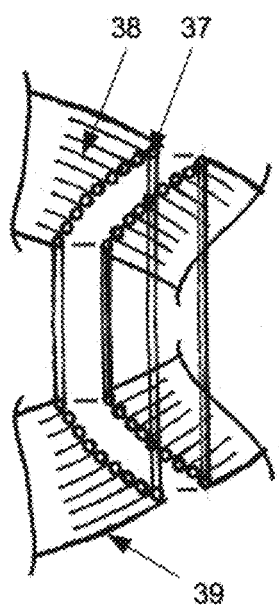
FIG. 5 is a diagram illustrating the fitting between the two adjacent coil segments of FIG. 4.
Figure 4:
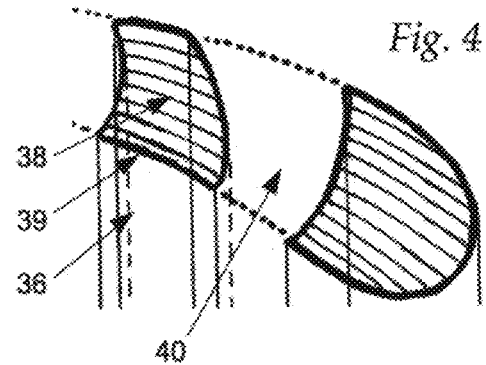
FIG. 4 is a diagram illustrating a cross section of two coil segments separated by another coil segment (not shown; implied by the intervening space) that can be used in the apparatus of FIGS. 1 and 2.
Figure 6:
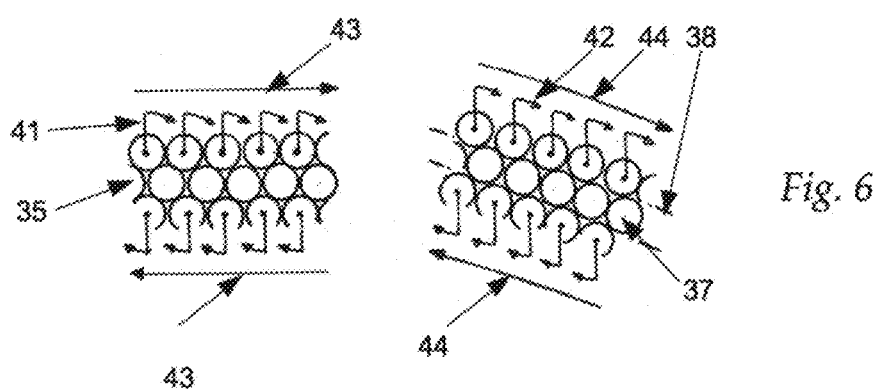
FIG. 6 is a diagram illustrating discreet winding pattern of wires in the curvilinear (Right) versus standard winding (Left), base layers, generated magnetic fields in each outermost wire and the ensemble field produced as a result of each winding pattern of the coils of FIG. 4.

Electromagnetic coils of the most commonly used type having winding patterns, base and frame geometries generally illustrated on the left half of FIG. 3. These common in the art coils have conductive pathways (35) energized (41) to generate fields both peripheral and intra-bore that process in a generally linear manner substantially close to the coil (43), producing the overall toroidal field geometry common to these coils. A plurality of common geometry field coils with varying radii can be assembled in a curvilinear manner as illustrated on the left half of FIG. 3. However, this is not a preferred enablement because of the linear nature of the generated field in each coil unit. Fin-shaped coils are a preferred enablement with conductive pathways (37) wound in a curvilinear geometry (38). Although individual conductive path field directions (42) are orthogonal per convention, ensemble fields both peripheral and intra-bore process in a generally curvilinear manner substantially close to the coil (44), producing the overall focused and constricted toroidal field geometry when combined with magnetically shielding encasements (1).

Integrated on the therapeutic terminus of at least one main coil in an apparatus is a RF antenna array. Antenna array geometry can be (1) generally concave and hemispherical (32) if disposed in a flush-fit manner on, and sharing geometry with, an indented main coil end and very closely peripheral to a spherical therapeutic space, or (2) generally convex and toroidal (33) if disposed in a flush-fit manner on, and sharing geometry with, an toroidal main coil end and more distant therapeutic space. Referring now to FIGS. 7-9, The antenna array (45) disposes a plurality of single frequency biased ring-shaped antenna frames comprising one ring (47) having a voltage-induced bias to the desired frequency of RF signal specific to 500 KHz (herein designated 43.5 MHz, the Larmor frequency of water protons at 1 T), plus many other rings disposing greater and less voltage bias (48). Upon relaxation of a resonant target in a FFZ (50), RF signal (49) is acquired by all antenna rings to varying degrees of efficiency as understood in RF receiver art. Spatial discrimination in RF source is provided by the antenna ring most efficiently excited, and the time when singular antenna cells and arrays within the ring are excited which depends on their distance from the RF source (as illustrated by the distance and azimuth of the RF source in the patient's head in FIG. 7).

Referring now to FIG. 8, each perfectly (47) or imperfectly (48) biased antenna ring comprises a plurality of antenna sets (51) lead-soldered to a 3-way junction gap (54). Upon excitation of any antenna cell, thereto being a fractal antenna as understood in the art (52), within a plurality of cells in the antenna set, a circuit is closed in the gap resulting in current being sent to the antenna base. The antenna set signal contributes to spatial encoding of RF source by its distinct frequency bias corresponding to a specific voltage (e.g., a antenna set in the 43.5 MHz RF signal biased ring expressing a 9 V current).

The antenna array preferably comprises 100 uniquely voltage biased ring frames, each ring comprising 100 antenna sets, and each set comprising 100 distinct fractal antenna cells. A unique fractal cell is thus provided for 1,000,000 voxels or approximately 1000 cm3 of analysis volume at 1 mm3/voxel. This is sufficient to monitor the immediate proximity (approximately 10 cm in any direction) around a 1 cm robot. Referring now to FIG. 9, the daunting engineering requirement of correctly corresponding 1,000, 000 antenna cells (63) to distinct leads for subsequent Fourier analysis in a k-space data storage unit (not shown) is avoided by random attachment of leads (62) from each cell in the back of the antenna array to mounts (64) on helically wound wire (60) on the antenna base (55). The winding pattern geographically separates signals from antenna rings disposed in a concentric manner (63) into corresponding leads on the antenna base disposed in a helical manner (60). The probability of closely-spaced antenna sets exciting the same base wire are thus avoided. 1,000,000 leads and base mounts can be fabricated on 1 m3 of both antenna array and antenna base, with leads and mounts, respectively on each device, being 1 mm apart.

Voxel assignment of each antenna cell is provided after random attachment and testing of the unit at multiple voltages with an axially disposed RF pinging source as commonly practiced in the art. Referring back to FIG. 7, a multi-frequency RF source (50, without the patient) is allowed to transmit the frequency range of each antenna array. Anticipated ideal frequency, e.g., again 43.5 MHz for water proton MRI, is biased-assigned to the innermost ring (47), higher and lower frequencies preferentially bias-assigned to smaller and larger (48) diameter rings, respectively. Bias and spatial correspondence of each antenna cell is provided by (1) modulating the RF output, 100 KHz at a time, until the entire RF spectrum of the antenna is electronically covered, and (2) articulating the RF source slowly about a 1000 cm3 volume corresponding to a human brain, 1 mm3 at a time, until the entire analysis volume is physically covered. Each voxel is therein assigned an antenna cell via computer correspondence of each cell to a unique set of distance and frequency settings. RF signal acquisition is then carried out as commonly practiced in the art.

Referring now to FIG. 10, the distinction between antenna array (45) latitudinal and antenna base (55) helical patterns is illustrated. Energized by a current regulated (58) power source, each antenna ring is energized to a different voltage (57) depending on the aforementioned bias. Excitement of closely biased rings (43.3-43.8 MHz) from an RF source at an azimuth (r, see FIG. 7) generating a water proton relaxation output at the 1 T Larmor Frequency results in all said rings being excited, the 43.5 MHz ring most efficiently, and at cell set locations also at an azimuth firstly before all other cells and sets due to closest proximity of the RF source to those sets. The helical pattern of reception leads is coordinated in an 16:00 clock pattern, heretofore the six immediately excited antenna sets causing current to process into helical wire at the 15:00, 16:00, 1:00, 2:00, 3:00 and 4:00 positions on the base (1:00 corresponding to 43.5 MHz on the antenna). The helical leads are translated at the base core into a linear pattern (60) that preserves the clock pattern, with each unique lead (56) from the antenna eventually attaching to a smaller set of lines to the k-space unit. The process is repeated upon reception of voltage from subsequent cell sets, at or near the correct frequency, events contributing in order of distance from the RF source. Spatial distinction in all acquired voxels is thus provided by timing of cell excitation, current modulation and geographical localization processed in the terminal core base.

The antenna base can be composed of low ferrite metal, high [Cu] content alloy, ferrite impregnated polymer or other field inductive material and can function as a take-up coil to harvest excess magnetic energy from cryogenic coils. The overall unit (antenna rings, leads and base) can dispense with traditional high voltage lines to and from a power source, avoiding potentially deleterious RF noise. In a preferred enablement, the winding density of the base coil is many times greater than the aforementioned 18 conduits per revolution, providing many more and more densely packed (preferably 1 mount/mm) mounting points. A hemispherical geometry for both the antenna array and the base (FIGS. 2-32) is preferred for optimal function as an take-up coil powered autonomous RF receiver unit.

Compression, Boundary and Counter-Rotating Torsion Fields

Figure 11:
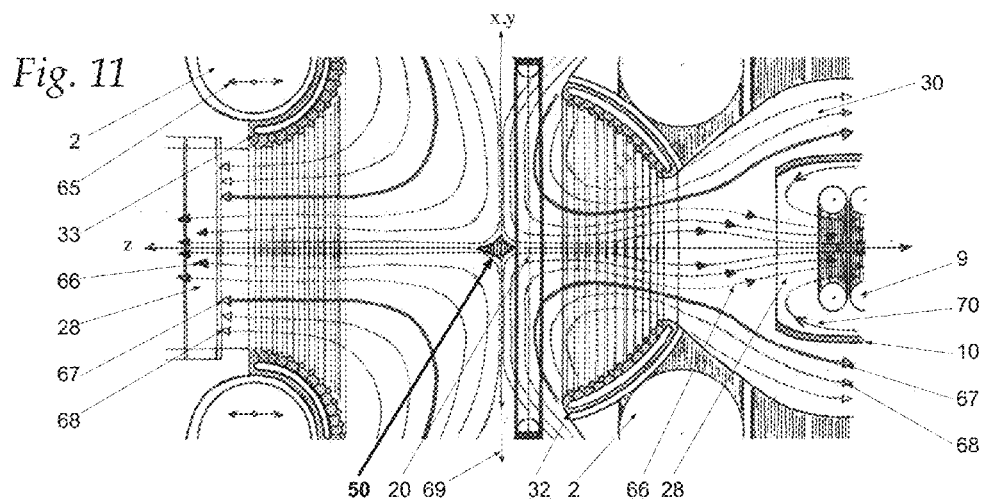
FIG. 11 is more detail diagram of magnetic fields produced by each field generator in FIG. 2.

Referring now to FIG. 11, elements of the ensemble magnetic field produced within an Asymmetric Field Generator type apparatus are illustrated. As described in FIG. 2, all components in both co-facing field generators are coaxial and concentric to a common bore axis (z). Field elements of the ensemble produced in each field generator are herein summarized and simplified according to electromagnetic component origin, heretofore referred-to as the non-rotating static field (68) produced by cryogenic main coils, the rotating field (66) produced by secondary and tertiary coils, and the flux and rotational gradient between static and rotating fields (67). Being the core or innermost elements of the ensemble, static fields process in volumes (30) inside rotating fields more closely to main coil elements (2). Rotating fields being the outermost elements of the ensemble process peripherally to static fields. In the bore space, rotating fields process specifically in spaces (28) closely disposed to the bore axis. Implied in the Left generator and described in the Right generator are revolving electromagnetic components which facilitate focusing of both static and rotating field elements. In the Right generator, secondary coils (9) disposed within intra-bore shielding (10) are energized with current direction to produce fields (70) which focus rotating field elements (66) very closely to the bore axis. Static field elements (68) and gradients thereto (67) are focused in spaces (30) around the intra-bore shielding.

Also described are toroidal (33) and hemispherical (32) geometry RF antenna arrays.

Fields from each generator converge on a central plane (69), in this aspect being also the transverse plane (x,y), the geographical middle of which along the z-axis is disposed a toroidal geometry magnetic pocket (50). In the illustrated aspect, net ensemble field strength produced in the Left generator is less than that produced in the Right generator, resulting in an axial shift leftward of the magnetic pocket from the presupposed midpoint (20) which is also the equatorial edge of the RF transmitter array when it is in its equilibrium position (z=0) due to asymmetry of converging fields. The magnetic pocket is also distorted to a geometry with unequal toroidal cones. Also described is the ability of the Left generator to articulate axially (65), enabling either recovery of magnetic pocket symmetry or exaggeration of asymmetry.

Figure 12:
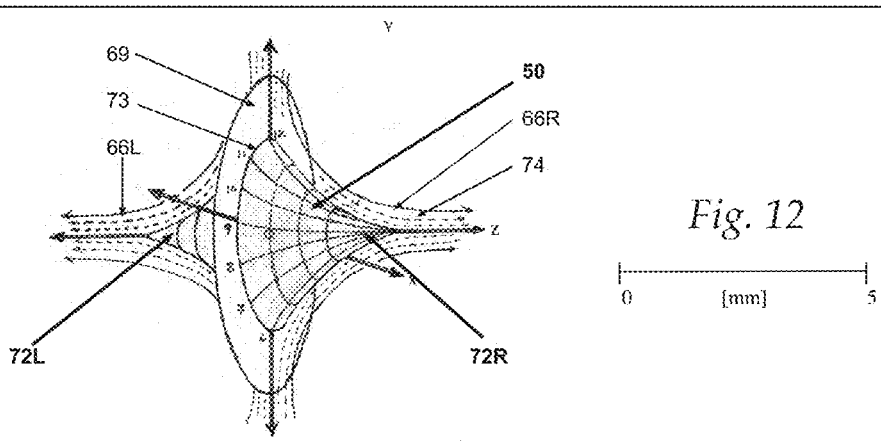
FIG. 12 describes the volume about which fields diverge from the convergence plane and back into the direction of generator bores.

The aforementioned magnetic pocket is produced upon convergence of mirror-image equal, coaxial toroidal geometry fields and defined by a dual toroidal null space geometry surface of non-specific field intensity below which flux densities, although non-zero, are insufficient for the operation and imaging of a robotic device. Referring now to FIG. 12, in a preferred enablement, the magnetic pocket (50) is defined by the 3D surface described by divergence of 1 G/0.0001 T field lines from the convergence plane (69) until resumption of nearly linear character at increasing distances from the central point (0,0,0). In a preferred enablement with high apparatus field energies, a 1 G pocket is compressed to present an equatorial divergence ring (73) 5 mm in radius, with each magnetic pocket constriction zone (72L, 72R) being 6 mm distant from the central point. In a preferred and enabled practice with counter rotating field elements on both sides of the convergence plane (66L, 66R), constriction points are also torsion fields which provide rotational torque to magnetically susceptible gyroscopic components disposed at those locations. Lower torques are provided by weaker field elements (74) peripheral to the rotating elements, more closely disposed to both the convergence plane and bore axis.

Figure 13:
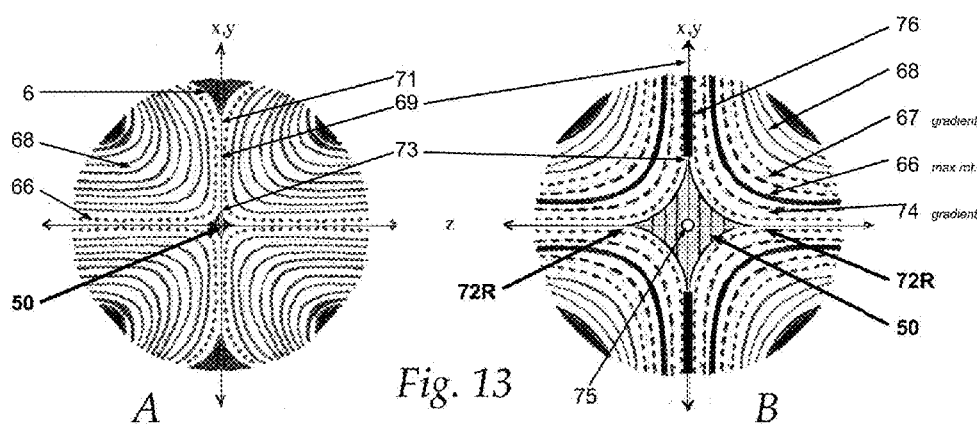
FIG. 13 generally describes magnetic field intensities on a scale illustrating the central shielding of two equivalent field generators as in FIG. 1.

Referring now to FIG. 13, described are summarized and simplified magnetic field elements of an ensemble field produced by a Symmetric Field Generator-type apparatus disposed closely to the convergence plane, at both apparatus (A) and robot (B) scales. Of note, the boundary field is included herein and described at a device scale illustration.

At the apparatus scale with illustration diameter (FIG. 13, A) approximately 150 cm, a centrally disposed curvilinear focusing shield (6) compresses static (68) and rotating (66) elements from both field generators toward the x,y-axis. Outermost rotating elements combine into a non-rotating unitary field at the convergence ring (71), process with radial linearity inward along the central plane (69), and disintegrate back into distinct field elements at the divergence ring (73) around and outside the magnetic pocket (50), then process back into main coil bores with resumed linear geometry. The magnetic pocket is enlarged for description and not illustrated to scale.

At the robotic device/magnetic pocket scale with illustration diameter (FIG. 13, B) approximately 15 mm, static (68) and rotating (66) elements from both field generators diverge away from the convergence plane (69). Distinctly, outermost elements of rotating fields from each generator are not allowed to interact directly. Instead, tertiary electromagnetic coils produce a boundary field (76), peripheral to all other fields and either non-rotating or rotating synonymously with fields produced by secondary coils. Outermost elements of the boundary field similarly combine into a non-rotating, unitary field at convergence (71) and diverge (73) outside the magnetic pocket (50), herein a toroidally symmetric structure with base point disposed at the central target (75). More details of static (68), static-to-rotational gradient (67), and rotating fields either at (66) or below (74) a preferred field strength of 1 G are illustrated. Con-facing magnetic pocket constriction zones (72L, 72R) are still provided, however the addition of a boundary layer contributes axial thickness to the generally linear fields processing back into apparatus bores.

Invention apparatuses can be operated with only main coils energized, main and secondary coils energized, or main, secondary and tertiary coils energized. Methods can be carried out in all operational modes, including (i) classic MRI-based diagnostic scanning if only cryogenic coils are energized, (ii) DGP with high energy pulses producing highly torqued, non-rotating convergence fields which rapidly collapse back into rotating fields in each generator, and (iii) robotic device translocation, medical effector protocols and novel imaging when rotating boundary fields are included with secondary and static fields.

In FIGS. 14-16, a generic Symmetric Field Generator type apparatus is described equivalently in the aforementioned operational modes. Summarized fields are illustrated at both the apparatus (Left) and robotic device (Right) scales. All apparatus and field components are replicated exactly similar on both sides of the central plane (x,y) describing mirror-image systems.

Referring now to the FIG. 14 Left illustration, static fields (68) produced by co-facing, equivalent, coaxial and concentric main coils (4) in each generator process within the apparatus (30) confined by the encasement (1) toward the central plane (x,y), and diverge back with wide azimuth (77) into the bore axis (|z|>0) avoiding intra-bore secondary coil components. Convergence at the central plane produces a relatively large magnetic pocket (50) defined by a large volume of low flux density disposed about the central point produced by divergence of outermost elements of two static fields (transverse arrows) processing back intra-bore (axial arrows). As more clearly illustrated and again as understood in the scientific convention, weak but non-zero fluxes exist al all points |x,y,z|>0. The magnetic pocket described herein (50) in the FIG. 14 Right illustration is disposed centrally in an approximately 50 mm sphere and is understood to have field densities much lower than the preferred enablement of 1 G. Field lines corresponding to 1 G are herein illustrated as the thinnest continuous lines (68). Of note, the wide divergence of bulk static fields in apparatuses operating in static field-only mode produces a partially compressed magnetic pocket, however field elements diverging from the central point immediately diverge at a wide azimuth (77). This generally describes the MINRB aspect.

Referring now to the FIG. 15 Left illustration, both static (68) and rotating (66) fields are produced in each generator. Distinctly due to production by these components, rotating fields process peripherally to static fields confined by the encasement (1), specifically within intra-bore spaces (28) wherein secondary coil components are disposed. Directions of secondary components revolution, and thus rotating field direction, are indicated by arrowed ellipses on axial locations in the left (81L) and right (81R) field generators, describing counter-rotating systems. Also distinctly, after divergence from the central plane, rotating field elements diverge back with narrow azimuth (78) into the bore axis (|z|>0) and directly into intra-bore secondary coil components. Referring now to the FIG. 15 Right illustration, field elements of the overall ensemble from both generators converge at the central plane to produce a relatively small magnetic pocket (50) defined by a small volume of low flux density disposed about the central point produced by divergence of outermost elements of two static and two rotating fields (transverse arrows) processing back intra-bore with increasing distance |z|>0 (axial arrows). The geographical limits of weak though non-zero magnetic fluxes, again arbitrarily designated as <1 G, about the central point are decreased due to the addition of a powerful rotating envelope (66), herein designated the new 1 T field line. A non-rotating static 1 G field line (68) persists, as well as gradients from the latter to the 1 T rotating line (67), and from each 1 T rotating field line to its mirror-image counterpart (74). In a preferred enablement, static fields are energized sufficiently to compress both the rotating fields with toroidal gradients (83) at 45 degree azimuths to both axes to dispose 1 T field lines within 1 cm of the central point, i.e., sufficiently small and strong enough to energize and control a robotic device. This generally describes the MICRB aspect.

Gradients between counter-rotating fields (74) are expected to have decreased rotational quality, approaching zero at the central plane by convention. Rotational magnetic energy that could potentially be applied to robotic devices is thus decreased due to rotational neutralization of outermost elements, resulting in increased distance between torsion fields. In a preferred enablement, tertiary coils produce rotating boundary fields which rotate synonymously with fields from secondary coils. Field intensity of boundary elements need not be great, i.e., approximately 100 G is preferred. Benefit provided is that rotational neutralization of secondary fields is avoided.

Referring now to the FIG. 16 Left illustration, static (68), rotating (66) and boundary (76) fields are produced in each generator. All generated fields are again confined by the outer encasement (1), and both non-rotating and rotating fields process within designated intra-bore spaces (30, 28 respectively). Rotating field direction are indicated by arrowed ellipses on axial locations in the left and right (81R) field generators, describing counter-rotating systems. Because of compression by main coils, secondary and boundary fields diverge back with narrow azimuth (78) into the bore axis ($|z|>0$) and directly into intra-bore secondary coil components—rotating fields proportionally into secondary electromagnetic coils (FIG. 1, 9) and boundary fields proportionally into rotating, permanent dipole axial rods (FIG. 1, 11). Referring now to the FIG. 16 Right illustration, ensemble field elements from both generators converge at the central plane to produce a relatively small magnetic pocket (50) produced by divergence of outermost elements of two static, two rotating and two boundary fields (transverse arrows) processing back intra-bore (axial arrows). Described are the 1 T rotating envelope (66), non-rotating static 1 G field line (68) gradients between the latter (67), and gradients from each 1 T rotating field line to the boundary field (74L, 74R). This generally describes the MICRS aspect.

The addition of a 1 T rotating field eliminates the need for static fields to generate sufficient magnetic flux at the therapeutic space to produce a magnetic pocket 1 cm in size, and eliminates the need for the static fields to themselves rotate, which would add complexity to apparatus design and operation. The addition of a peripheral rotating field additionally reserves contribution of static fields to a proportionally compressive role.

Continuous and autonomous generation of rotating magnetic fields at a 1 T intensity is acknowledged to be impractical for non-cryogenic and highly motile electromagnetic components. It is also not necessary for the trapping, energization and translocation of a robotic device at magnetic pocket scale. Therefore, secondary coils are preferably energized with rapid (~250 ms) high voltage DC current pulses whilst the components revolve. Alternatively, secondary coils can be wound in a helical manner and energized with rapid (240 Hz) high voltage AC currents to generate similar rotating fields. Coils in the latter configuration can revolve or remain fixed. These methods and apparatuses for generating rotating magnetic fields are well understood in the art.

Non-rotation at the central plane between two mirror-image counter rotating, coaxial equivalent fields as in the MICRB aspect produces increasing torque imposed on secondary coils (mechanical, if secondary coils revolve; electromagnetic, if secondary coils are AC powered and stationary) as coil and/or field rotation proceeds. The condition wherein a central blended field remains non-rotating while rotating fields and components continue to mechanically or electromagnetically revolve is untenable. As understood by convention, the blended field will collapse with dynamic quality that increases with intensity and rotation rate of fields. The invention minimizes this phenomena with the use of pulsed, rotating boundary fields.

Figure 17:
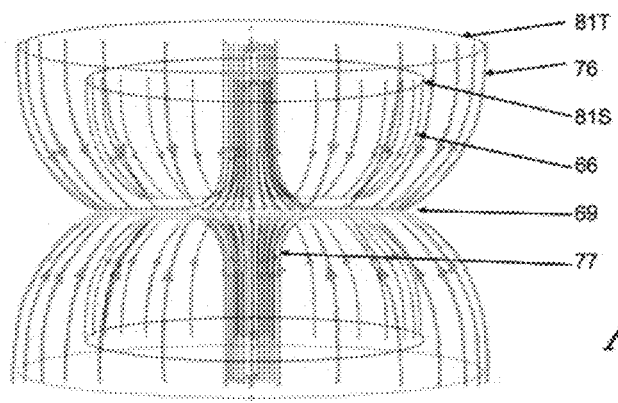
FIG. 17 describes qualities of MINRB structures (A) and MICRB structures in the presence of non-rotating (B) and rotating (C) boundary fields as well as MICRB structures (D) and DGP induced hybrid structures (E) resembling geometric passerelles.
Figure 17:
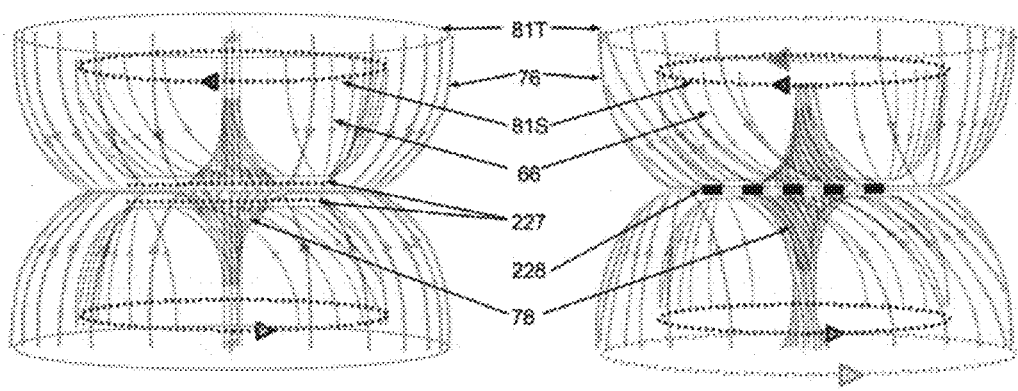
Figure 17:
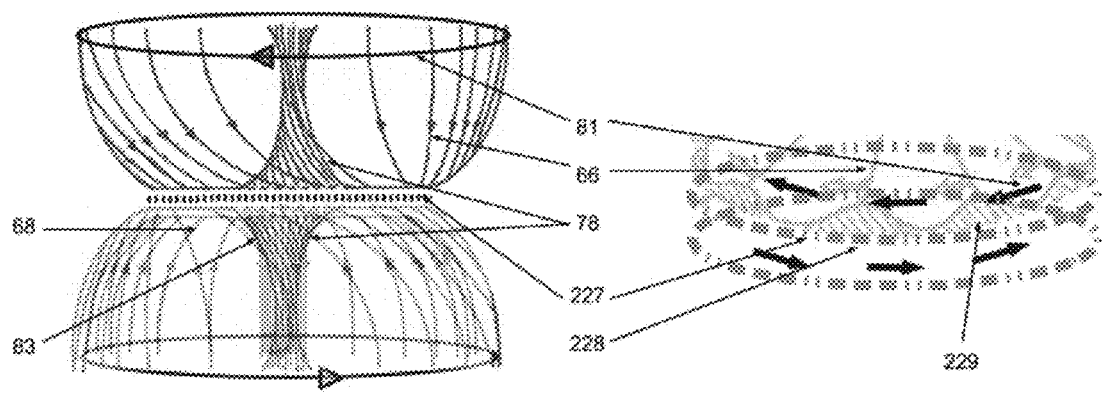

In FIG. 17, a preferred temporal sequence of energization pulses and rotational quality is described enabled by tertiary coil-generated boundary fields. In all aspects illustrated, it is understood that an invariant, compressive static field is disposed within each aspect, with increased compressive intensity in the preferred aspects illustrated in FIG. 17, D.

Further understood per convention that distinct fields in an ensemble is conceptual however distinction is made to illustrate field elements, portions or geometries resulting from differential activity of separate electromagnetic components, in particular regarding rotating vs. non-rotating and fields. Also, regardless of labeling or description, fields on both sides of the central planes in each illustration portion are identical, i.e., mirror image, differing only in the relative counter-rotational directions of motile field elements.

Referring now to FIG. 17, A, described is the non-preferred comparative MINRB aspect, describing significant magnetic field structures that include non-rotating secondary (66) and tertiary (76) fields, and their respective rotational vectors (81S, 81T)—herein net=0. In the aspect of low static field intensities, as previously described, diverging fields process back into apparatus bores with relatively wide azimuth (77) to bore axis.

Referring now to FIG. 17, B, described is the MICRS aspect where the boundary field (76) separating counter-rotating (81S) fields (66) in each generator does not rotate (81T). Gradient between non-rotation close to the central plane and rotation (227) exists on both sides of the central plane between each rotating field and both sides of the boundary field. In a further enablement, the boundary field is as thin as possible (~1 mm=+/−0.5 mm about the x,y-axis) and in the order of 100 G (as described in FIG. 16). Energizing the boundary field to intensity within 1% of the maximal rotational field intensity of 1 T, combined with adequate compression from static fields (78), enables a thin gradient (0.01-1 T) from the central plane being also the geographical center of a robot trapped in the magnetic pocket, to the robot drive coils disposed ~5 mm axially distant from the central point. To prevent excessive build-up of torque (227), the boundary field (76) is preferably terminated and resumed within 50 ms every 250 ms with secondary coils revolving, or fixed and producing, a rotating magnetic field at 60 Hz [revolutions/min]. Undesired blending of outermost elements of the rotating field (66) are thus limited to brief 50 ms transients occurring four times per rotational cycle of 1 sec, limiting maximal axial distance of torque in each event to $\pi/12$ or 15 degrees. Very transient, although extant and unavoidable, blending of rotating fields produces counter-rotating neutralization-induced torque as described in FIG. 17, D.

Referring now to FIG. 17, C, described is the preferred enablement of the MICRS aspect where the boundary field (76) from each generator rotates (81T), preferably synonymously, most preferably at the same rotational rate (81S) as fields produced in secondary coils (66). Thereto, no rotational gradient exists between secondary and tertiary fields. However, outermost elements of counter-rotating boundary fields blend with no rotation at the convergence plane resulting in torque between these fields (228). To prevent excessive build-up of this torque, similar to the aspect described in FIG. 17, B, the rotating boundary field herein (76) is preferably terminated and resumed within 50 ms every 250 ms with secondary coils revolving/producing a rotating magnetic field of 60 Hz. Undesired torquing of outermost elements of the rotating boundary field are thus limited to 250 ms transients occurring four times per rotational cycle of 1 sec, limiting maximum axial torquing to $(\pi/4-\pi/12)$ or 75 degrees. Also similar to the aspect described in FIG. 17B, transient, blending of rotating boundary fields produces counter-rotating neutralization-induced torque as also described in FIG. 17, D.

Buildup of rotational torque due to convergence-induced neutralization of motility in blended fields is undesired.

Torque of the kind provided to robotic device drive coils requires only compressed and constrictive rotating fields disposed about drive coils. Divergence of counter-rotating fields provides diametrically directed torsion fields but also convergence-induced torquing whether the boundary field rotates (as in FIG. 17, C) or not (as in FIG. 17, B). Both aspects have advantages and drawbacks. In MICRS fields with non-rotating tertiary fields pulsing four times every 1 second rotation as described in FIG. 17, B, axial torquing of 75 degrees every 250 ms is generated between the secondary and tertiary fields. Mechanical and electromagnetic stresses on both coil sets is produced, however, there is no torque stress between tertiary coils of each field generator because the boundary fields are axially linear. In contrast, in MICRS fields having boundary fields that rotate synonymously with secondary fields and tertiary coils pulsing at 240 Hz as described in FIG. 17, C axial torquing of 75 degrees every 250 ms is also generated between the two counter-rotating tertiary fields. Mechanical and electromagnetic stresses on the secondary coils are avoided except for the brief 50 ms tertiary transients and stresses on tertiary coils are more pronounced. Because tertiary coils are fixed and not motile, however, they can be mounted more securely and withstand stresses of rotational torque more easily than high voltage, heavy and rapidly rotating secondary coils, magnetized bars, drive shafts and other components which depend on absolute concentricity and lack of azimuthal inclination for optimal operation.

In addition, pulsing of current is more readily performed in fixed versus motile coils due to conduction pathway requirements. Likely high voltage power lines to tertiary coils will extend from main coils or apparatus encasement (not shown but understood by persons skilled in the art). High voltage lines to secondary coils will likely be wired through the drive shafts, requiring current transfer through a physical gap between motile and fixed components. This can be a junction, brushing or induction type gap as commonly practiced and well understood in the art. In any enablement thereto, conduction of a pulsed current is non-ideal and risks sparking, RF noise and undesired short circuiting. As a pulsed field is necessary to avoid buildup of rotational torque in magnetic fields, pulsed currents are more preferably carried through fixed conduction pathways. Therefore, the aspect described in FIG. 17, C is the most preferred enablement.

Referring now to FIG. 17, D, described is the MICRB aspect which occurs during brief 50 ms transients when the rotating boundary field is terminated to prevent excessive buildup of rotational torque on tertiary coil components and large rotational gradients between field elements. Counter-rotating (81) secondary fields (66) from each generator are allowed to briefly blend, producing a non-rotating radial field at the convergence plane (227). As described above, angular torque imposed on secondary coils is 15 degrees every 250 ms. Compression (83) by static fields (68), again not illustrated but implied in all other aspects, including the upper portion of FIG. 17, D, results in focusing of divergent fields in a more axial direction (78). The 50 ms of $\pi/12$ torque imposed on secondary coils every revolution is considered to be manageable.

Mechanical and electromagnetic torque-imposed drawbacks aside, if MICR fields were allowed to blend continuously, field lines would not "twist" and build an infinite amount of torque at the convergence plane. Un-blending would occur in a highly dynamic manner producing magnetic field structures with high radial angularity and also un-blended MICR fields that "detached" from the convergence plane. The structure would not be static and immediately resume the characteristics of a semi-stable MICRB field until field coil revolutions/field rotations again imposed torque beyond the ability of converged fields to remain blended. Most likely, the transient structure would have properties of both MICRB and MICR fields wherein a radial arrangement of blended field elements alternates with un-blended elements. Referring now to FIG. 17, E, illustrated is the dynamic structure having counter-rotational quality (81) on both sides of the central plane, axially distal disposed rotating fields (66), and both non-rotating blended (227) and blended rotating (228) components. The latter may not be flat (as illustrated by the alternating dashed lines) and instead be disposed in an radial undulating or passerelle structure (229).

The lifetime of this structure is expected to be equal to the time between complete un-blending and resumption of semi-stable blending which is the DGP frequency, estimated to be 5 ms. In a preferred enablement for robotic device management, the DGP pulse frequency is zero from avoidance of these dynamic structures, brief tertiary coil down times (50 ms), synonymous rotation of secondary and tertiary coils, and minimal mechanical revolution/field rotation rates. However, if more intense field energies are required, the probability of DGP events will increase. In such aspect, at the preferred revolution/rotation rate of 60 Hz, 5 ms events would populate 2% of the ensemble convergence structures, increasing to 12% at 360 Hz of coil revolution/field rotation. Lastly, if field lines were cut and excess field angularity were resolved with rapid coil de-energizations, generation of wide-band RF noise may occur. Though not a focus of the invention, dynamic structures hereto produced and disposed closely to the convergence plane may provide benefit for modulation of electro-active tissues.

Figure 18:
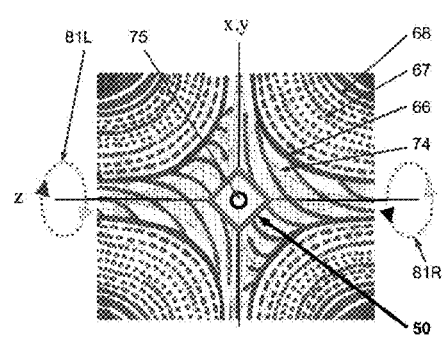
FIG. 18 describes in more detail the static and rotating fields, and field gradients in the proximity of a null space (A), and the effect of compressing the field structure with greater main coil energies onto a robotic device (B).
Figure 18:
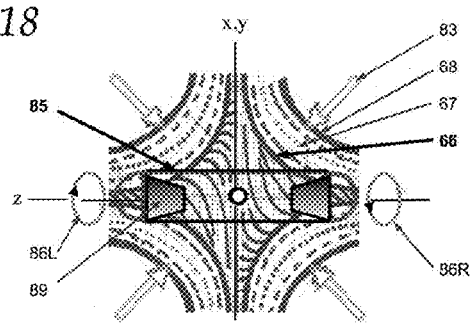

Referring now to FIG. 18, A, in an aspect of the most preferred enablement, a magnetic pocket (50) is created at the exact center (75) of the convergence plane wherein axially counter-rotating (81L, 81R) 1 G field intensities are generated in diverging toroidal structures (66) with progressively decreasing field intensities and rotational quality (74) until no appreciable flux or torque exists in the actual pocket (50). Outside the magnetic pocket at increasing distance would be the gradient (67) between the rotating and non-rotating static field, and the static field (68). For purposes of illustration, the tertiary fields are heretofore neglected. At the illustration scale, the magnetic pocket is not expected to generate sufficient rotational torque to a robotic device disposed centrally within due to excessive size and inadequate rotational rates of the 1 G surface.

Referring now to FIG. 18, B, in the continuing aspect of the most preferred enablement, the magnetic pocket is compressed in toroidal directions (83) by more energized static fields (68), also resulting in compression of static-to-rotating gradient field elements (67), the 1 G rotating magnetic pocket surface (66), and gradients less than 1 G until negation (75) by definition inside the pocket. Additionally, secondary field rotational rates in both counter directions are increased (86L, 86R). Resultant thereto are axially disposed, con-facing constriction field structures that provide both enough field strength (>=1 G) and field rotational rates (86) to the axially disposed drive coils (89) of a centrally disposed robotic device (85). Constriction fields are heretofore referred-to as torsion fields because of the rotational torque they provide to rotating components of robot drive coils disposed concentrically about said torsion fields. Also, the entire magnetic structure comprising the radial volume disposed inside the divergence ring of the 1 G field line (or AT of drive coils of a robot disposed within) and extending axially |z|>0 until torsion fields resume general axial linearity/longitudinal geometry is heretofore referred-to as the Free Field Zone or FFZ.

Figure 19:
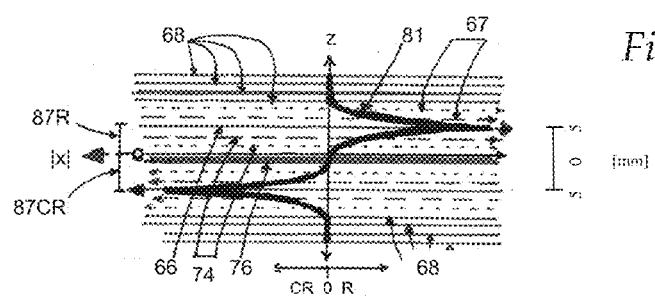
FIG. 19 describes converging static, counter-rotating and a boundary field on both sides of a convergence plane emphasizing rotational vector magnitudes and directions from a planar representation of a 3D radial effect.

Referring now to FIG. 19, rotational gradients and directions of convergent and separated counter-rotating fields are described by a 2D vectorial approximation of 3D rotation along a line (z) normal to the convergence plane (x) at the scale indicated. The line can intersect the convergence plane at any point between the convergence and divergence rings. Described on both side of the central plane are the static field lines, decreasing in intensity in the direction of convergence (68), the 1 G rotating field line (66), the gradients between the static and rotating fields which decrease in field intensity and increase in rotation (67), the gradients between the rotating and boundary fields which decrease in field intensity and decrease in rotation (74), and a single boundary field (76) disposed 1 mm towards the counter-rotating direction (87CR>87R). Directions and magnitudes of field rotation (81) are indicated, specifically describing the counter-rotational quality of fields. A 10 cm long robotic device disposed along the normal line (z) would experience maximal rotational torque at distances+/−5 mm from the central point. The FFZ for this trans-central point would approximately extend to the upper and lower limits of the illustration or about +/−15 mm [z].

Figure 20:
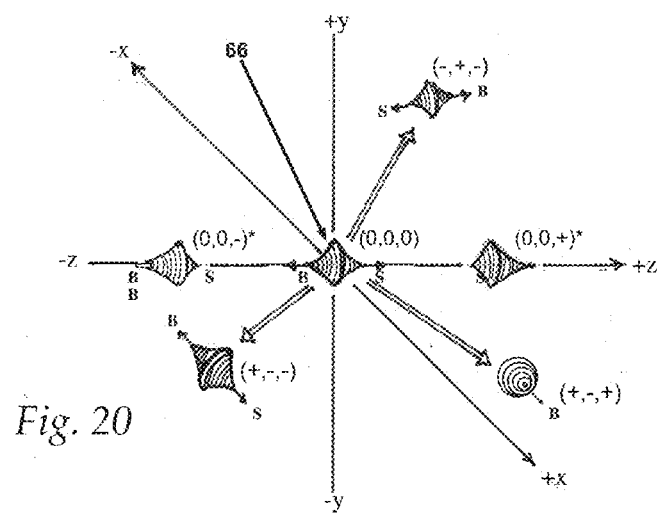
FIG. 20 describes the translocation of a FFZ along a bore axis (+/−z) with resulting asymmetry (*) as compared to the starting point (0,0,0).

Referring now to FIG. 20, described is a FFZ having diametrically opposed torsion fields disposed at coordinates (0,0,0) with a robotic device not shown but disposed within having its bow (B) and stern (S) ends at the indicated axial locations. Described is a method for translocating the robot by translocation of the FFZ at distances from the origin (0,0,0) and re-orientation at azimuths to any coordinate axis. Coordinates thereto are as illustrated with the x-axis being into and out of the page. Inclusive are translocation of the robot to the left (−z direction, 0,0,−)* and right (+z direction, 0,0,+)* along the apparatus bore axis. Asterisks indicate that the bilateral symmetry of the original magnetic pocket has been distorted as the result of selective field generator energization, as previously described in FIG. 11. Continuing exemplary descriptions include translocation and re-orientation of the FFZ in a backward, upward and rightward direction (−,+,−), translocation and re-orientation in a forward, downward and leftward direction (+,−,−), and translocation and re-orientation in a forward, downward and rightward direction (+,−,+) which results in the robot bow being directed normal to the reader. The method is a preferred enablement for translocation and re-orientation of a robotic device through movement and articulation of field generators.

Figure 21:
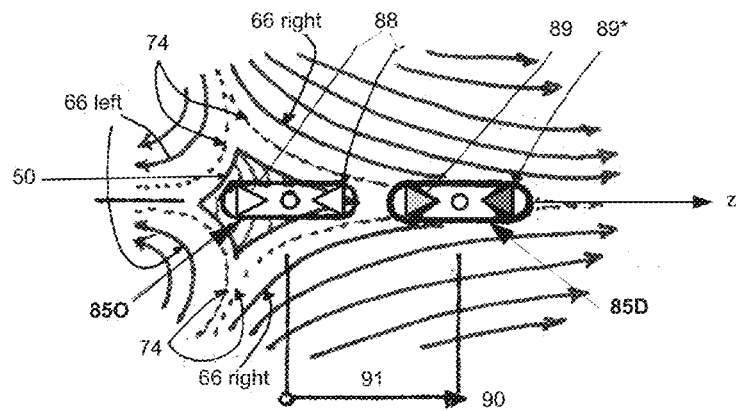
FIG. 21 describes the translocation and changes in drive coil energy states of a simplified robotic device as in FIG. 20 when it is subjected to an imbalance in relative field generator gradients.

In another preferred enablement of robotic device translocation and other management, continuing from descriptions given in FIGS. 11, 18 and 20, a robotic device can be translocated by an asymmetric FFZ wherein unequal torsion fields and gradients move a device. Referring now to FIG. 21, illustrated is a bilaterally asymmetric magnetic pocket, proximal field structures and their effect on a robotic device disposed therein. The magnetic pocket (50) has been distorted rightward by net energization of the rightward field generator over that of the left generator. Also distorted are rotating field gradients at (66) and beyond the robotic device's drive coil activation thresholds, and lesser rotating and field strength gradients, including diverged elements (74). Resultant is that the original disposition of a robotic device (850) has been translocated in an axial direction (90) for a distance (91) to its new destination (85D). In the field structure described herein, field strengths and torsion field rotational rates and insufficient to activate device drive coils (88) in a robot significantly unmoved from its original position (850). However, torsion field properties achieve (89) and surpass (89*) drive coils activation thresholds at the new robot position (85D).

Figure 22:
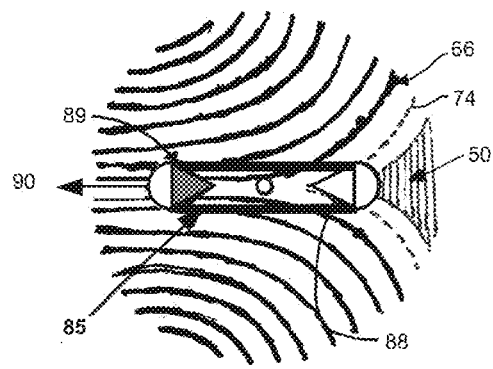
FIG. 22 describes a robotic device and simplified field illustrations as in FIG. 21, where a free field zone similar to that in FIG. 18 is generated off-center from the robot, resulting in activation of one drive coil and translocation of the robot in the direction of greater axial field gradients.

In another preferred enablement of robotic device translocation and other management, a FFZ can be created on one side of a robot, forcing the robot to translocate in an axial direction away from the pocket in the direction of bias. Referring now to FIG. 22, described is a bilaterally symmetric magnetic pocket (50), proximal gradients (74) and rotating fields at (66) and beyond device AT, and their effect on a robotic device disposed axially but significantly off-center. The robot (85) is pulled axially in the field bias direction (90) by magnetic forces greater on the left side of the robot than the right. Also resultant are torsion field energization beyond AT of the leftward drive coil (89) but not of the right drive coil (88) due to field structure. The robot will continue to process leftward in a homogenous permissive medium so long as the field structure is maintained.

Figure 23:
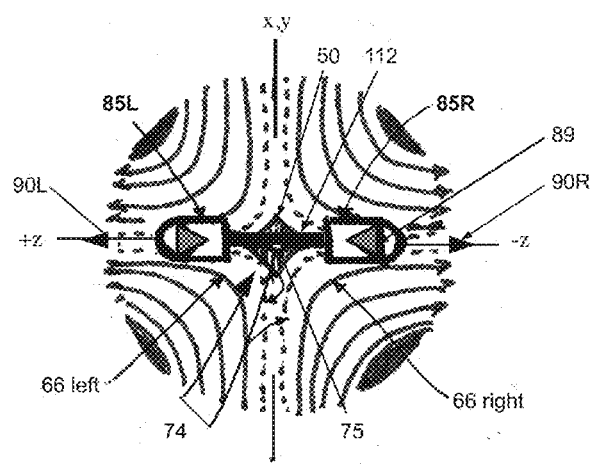
FIG. 23 describes the change in geometry and drive coil energy states of a twin hull robotic device when overall field intensities are intensified. Co-facing fields are equal.

In another preferred enablement of robotic device management, a FFZ can be created centrally to an adaptive geometry robot, forcing the robot to separate into equally balanced hull sections in diametrically opposed axial directions away from the pocket. Referring now to FIG. 23, described is a bilaterally symmetric magnetic pocket (50), proximal gradients (74) and rotating fields at (66) and beyond device AT, and their effect on a robotic device formerly disposed centrally to the central point (75). The robot hull sections (85L, 85R) have been pulled apart in axially opposed directions (90L, 90R) due to field bias overcoming hull sections connective integrity and by allowance of on-board algorithm or operator RF signal. After unreeling of the entire connective wire (112), the robot will remain immobilized and axially oriented, so long as the described field structure is maintained and mechanical connections are not overcome by magnetic forces. Of note, torsion field energizations are beyond AT of both drive coils (89) at the new locations of hull sections and will continue to re-energize on-board power supplies as desired.

Regenerative, Gyro-Stabilized Drive Coils

In addition to robotic device navigation via disposition within a motile magnetic pocket, other magnetic pocket-related navigation methods, and energization through torsion fields, robot positional stabilization is provided by magnetic and gyroscopic characteristics of drive coils. Integral to drive coils, concentric, radially balanced, rotating inertial masses are disposed substantially to the terminus (bow or stern) of a robot for positioning optimal stabilization. Revolving magnetically-susceptible rotor bars, to which aforementioned gyro-masses are attached, are disposed substantially to radial extremities for optimal induction of rotational magnetic torque from torsion fields and for additional gyroscopic effect Referring now to FIG. 24, described is a cross-sectional view of a homopolar motor type magnetic gyroscopic drive coil enclosed within a magnetic field transparent casing (97) composed of aluminum, hard polymer, titanium or [Ti] alloy in a preferred enablement. A set (preferably between four and thirty six) of rotor bars (92) is disposed directly inside the field transparent casing. Rotor bars are magnetically susceptible, approximately 0.15 mm diameter×4 mm length and can be composed of magnetized metal wire or permanent dipole magnetic bars with positive poles disposed towards termini (+z). Also disposed with rotor bars is a conductive bar (95) of copper, silver or gold alloy that serves as the revolving homopolar contact-less bushing. An inertial balance is disposed 180 degrees opposite thereto. Integral to extremities of rotor bars is a wheel or disc-shaped gyro-mass (104) which can be a non-functional inertial weight or have function such as a battery, electric or optical sensor. Rotor bars are aligned from NEG poles (disposed proximal to device axis) approximately 45 degrees at an outward azimuth then bent inward toward the device axis wherein the POS pole is disposed close to the drive coil core. Disposed in the mantle volume between rotor bars & bushing and core are a stack of weakly conductive, magnetically permissive discs (93) of varying diameter, composed of soft iron, Fe2O3-impregnated hard polymer or silver particle-impregnated ceramic, that serves as the homopolar inductive pile. Rotor bars and gyro-mass free-float revolve between the outer casing and inductive stack suspended in a thin (~0.2 mm) layer of low melting temperature, high conductivity fluid (101) composed of liquid mercury, a 50:50 molar ratio mix of [K] and [Na] ions in low density and low viscosity ionic liquid, or a eutectic mixture of −75:25 [K:Na].

Upon exposure to a terminally (+z) directed magnetic field, the drive coil tends to align parallel to the field due to individual dipole moments of bent rotor bars and group dipole moment of rotor bar set. Minimized collective dipole moment is only achieved with co-linear alignment of magnetically-susceptible concentric and co-axial drive coil components with the external field. Upon exposure to a terminally (+z) directed rotating magnetic field sufficient to overcome drive coil inertia, i.e., drive coil activation threshold, rotor bars, gyro-mass and bushing bar revolve with increasing revolution rate until synonymy with the external field is achieved. Gyroscopic stability is provided with increasing benefit with external field rotational rate.

Referring now to FIGS. 24, 25 and 26, rotor bar set (92) dipole moment and bent geometry creates an approximately linear internal magnetic field (100) in the inductive pile, processing from transversely bent North poles disposed at drive coil termini to azimuthally angled South poles disposed further inward to the drive coil. Consistent with homopolar physics convention, the longitudinally linear, axially rotating internal magnetic field (100) induces an orthogonal electric current (99) in the inductive stack (93) that, in one direction as illustrated, processes radially outward from the inductive stack through the conductive liquid layer to the rotating bushing that is attached to a rotating, lubricated [Cu], [Au] or silvered disc (96) that is in electrical contact with the radial NEG terminal (102) of a hollow core battery (94). Current then flows into the battery, recharging it as understood in the art, and outward through the radial POS terminal at the other end. Herein, current is conducted through [Cu], [Au] or conductive polymer wire, sealed within an electrical insulator cap (103), that leads from radial POS electrodes back into the battery core that is itself electrically insulated (98). Current processes in a terminal (+z) direction closing the circuit in the non-electrically insulated core section of the inductive stack.

This is a preferred enablement of battery recharging using a homopolar motor type drive coil, torsion fields and current direction. In the absence or lack of sufficient torsion field gradient or rotational rate, current in the reverse direction can induce rotor bars revolution for gyroscopic effect. Per convention, this current induced rotation less efficient in generating mechanical rotation than in rotor-stator type drive coils (see: below). In a preferred enablement not illustrated herein but obvious to persons skilled in the art is that the circuit can extend further terminally to electrodes, junction gaps or circuit components disposed at, or terminal to, gyro-masses before extending back to bushing terminals, providing short high voltage transients potentially useful for effector methods such as tissue ablation, cauterization and device energization.

Figure 27:
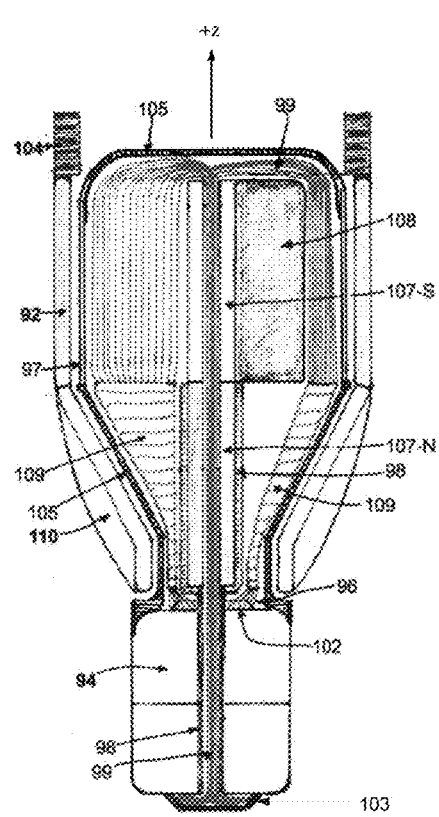
FIG. 27 describes a rotor stator drive coil for robotic devices viewed cutaway from the side. Integral thereto are gyroscopic masses and a rechargeable battery.

Referring now to FIG. 27, described is a cross-sectional view of a rotor-stator motor type magnetic gyroscopic drive coil wherein a set of rotor bars (92) free-float in the therapeutic milieu outside a magnetic field transparent casing (97) and secured to the apparatus via concentric rings or shell. Integral to extremities of rotor bars is a gyro-mass (104) which, being also exposed to the milieu and disposed to drive coil termini, is preferably a surgical tool or propulsion aid such as a propeller or screw. Disposed on outer edges of rotor bars can be propulsive fins (110). Rotor bars are aligned from South poles (disposed proximal to device axis) approximately 30 degrees at an outward azimuth then bent inward toward the device terminus (+z) and parallel to the device casing wherein the North pole is integrated with the gyro-mass. Disposed within the magnetically transparent portion of the drive coil casing (97) on the North terminus is a weakly conductive, preferably soft iron mantle (108) that focuses internal magnetic fields. All components inside the magnetically transparent and non-transparent (105) sections of casing are fixed, eliminating the need for conductive liquid or lubricant inside. The non-transparent casing sections can be ceramic-coated pure iron, [Fe]-impregnated polymer or Mu metal. The rotor bars (92) can be coated with PTFE, Nylon or, in a preferred enablement, super hydrophobic/oleophobic micron scale coating to enhance passage through tissue by reducing drag coefficient (CD).

Similar to homopolar motor type drive coils, rotor-stator drive coils upon exposure to a terminally (+z) directed rotating magnetic field, the drive coil tends to align parallel to the net field direction. Rotor bars plus gyro-mass revolve with increasing rate until synonymy with the external field, providing both gyroscopic stability and positioning within the magnetic pocket.

Figure 28:
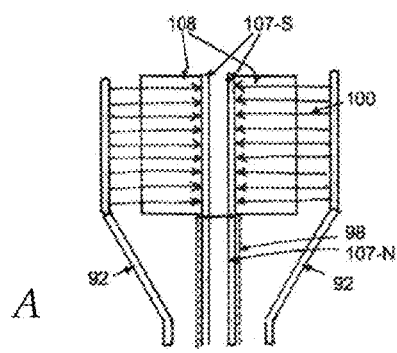
FIG. 28 describes the direction of magnetic fields generated by rotor-stator motor rotor bars within the inner mantle (Top), and electric currents along conductive pathways in one direction (Bottom).
Figure 28:
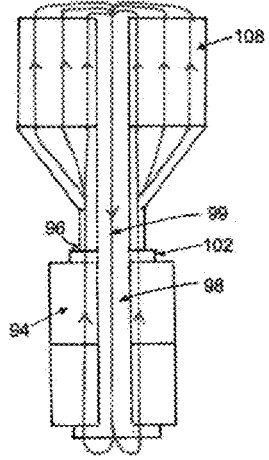

Referring now to FIGS. 27 and 28, rotor bar set (92) dipole moment and bent geometry creates a transverse internal magnetic field (100) in the focusing mantle (108), processing from longitudinally aligned rotor bar North poles disposed circumferentially about drive coil termini to the South portion of a tubular magnet (107-S) disposed in the core.

Per convention, the radially directed inward, axially rotating internal magnetic field (100) induces an orthogonal electric current (99) in conductive wire dispersed longitudinally outside the mantle (108) and non-insulated South pole (107-S) of the hollow magnet that, in one direction as illustrated, processes longitudinally rearward (−z) into the insulated (FIG. 27—98) North pole (107-N) of the core magnet, then through the insulated core of a hollow battery (94) to the other terminal. Herein, current is conducted through wire, capped with electrical insulator (103), that leads to radial electrodes in the POS terminal and back into the battery, recharging it as understood in the art, and processing in a terminal (+z) direction through to the NEG terminal (102). The NEG terminal leads (96) to an wire trunk that fills most of the conical volume between the battery and the mantle. Trunking insulation (109) terminates at the section of drive coil where rotor bar North Poles, i.e., the forward half of rotor bars, begin and also where the casing is transparent. Exposed electrically conductive wire wound around the mantle herein carries current in a terminal direction (+z) then back radially inward until the conductive pathway (99) returns to the non-insulated South pole of the hollow magnet, closing the circuit.

This is a preferred enablement of battery recharging using a rotor-stator drive coil, torsion fields and current direction. In the absence or lack of sufficient torsion field gradient or rotational rate, current in the reverse direction can induce rotor bars revolution for gyroscopic effect. In a preferred enablement not illustrated specifically herein but obvious to persons skilled in the art is that the circuit can extend further terminally to circuit components disposed at, or terminal to, gyro-masses before processing back to the South pole of the core magnet, providing efficient voltage potentially useful for charge carrying devices having therapeutic or analytical function.

Rotor-stator drive coil function is dependent on efficient (i) focusing of internal magnetic fields, (ii) exposure of conductive pathways to magnetic fields, (iii) insulation of internal electrical current, and (iv) shielding from external magnetic fields. These are provided by, respectively, (i) field transparent hull sections (97) that facilitate rotating internal fields (100), (ii) lack of magnetic or electrical insulation that facilitates generation of electric current in this volume (FIG. 28, B—108), (iii) magnetic (105) and electrical (FIG. 27—98) shielding that prevents field generation between South poles of rotor bars (92, 110) and the North pole of the core magnet (107-N)—which would disrupt current generation by creation of longitudinal rather than radial internal magnetic fields, and (iv) terminal shielding (FIG. 27—105, Top) that prevents torsion fields from processing through the drive coil and focuses external constrictive and rotational gradients into the rotor bars.

Figure 29:
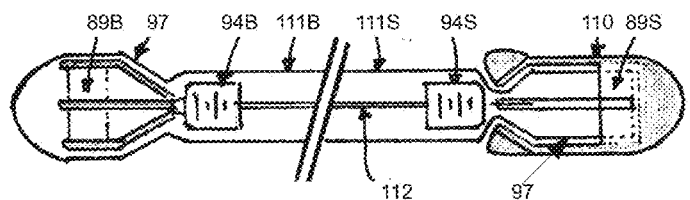
FIG. 29 describes a generalized robotic device having a homopolar drive coil (left side) and rotor stator drive coil (right side). Exposed rotor stator motor rotor bar sets integrate hydrodynamic fins.

Referring now to FIG. 29, a generic robotic device is described. Encased in a magnetic field transparent bow end hull section (97), the robot disposes a homopolar motor type drive coil (89B) attached on an on-board battery at that end (94B). Both the bow and stern of the main hull section (111B, 111S) are understood to be composed of non-transparent/shielding material (FIG. 27—105) and enclose an electrical or electromechanical connection (112) to an on-board battery at the stern end (94S). Connected thereto is a rotor-stator type drive coil (89S) disposing propeller-type extensions (110) on the rotor bars concentric to the field transparent hull section (97).

The device described in FIG. 29 is a functional medical drone, capable of translocation through a permissive medium within a motile free field zone that is generated in a patient and which disposes con-facing, coaxial, counter-rotating torsion fields providing stable robot positioning through actuation of gyro-magnetic drive coils and their disposition within torsion fields. Algorithmic and analytic functions are provided by enabling micron-scale devices, including microprocessor, RF transmission and reception, optical and electrical—well understood and ubiquitous in the art. If disposing batteries and other charge-carrying devices, the robot can function indefinitely for the life of drive coil and other components, recharged via counter-rotating torsion fields. The device described can serve as the basic template for a wide variety of robots.

Medical Robots, Untethered Tools and Implants

Figure 30:
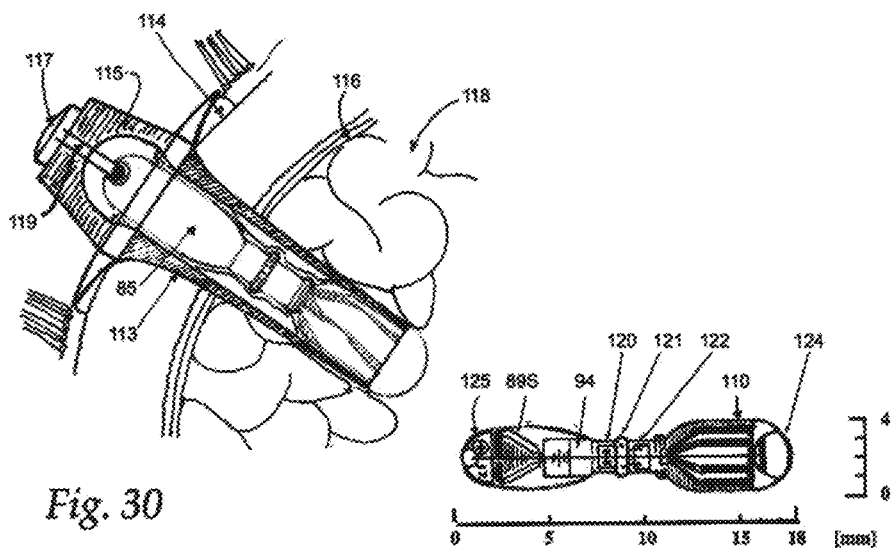
FIG. 30 describes the generalized robot from FIG. 31 encased within a cranial implant dock with its bow end to the brain (Left), and the robot in more detail including on-board devices and scale (Right).

In a preferred enablement, the robot is placed in a patient through a multi-purpose probe. Referring now to FIG. 30, a neurological robotic device (85) is illustrated encased in a trans-cranial port disposed through a patient's skull and pericranium (116) about an inch into the brain (118). The port is secured to the shaved and partially un-dermalized perimeter via bio-adhesive (114). The robot is disposed in the dock portion (113) of the port, which can be a blunted 7 Gauge hypodermic needle, with the terminus of the Bow end exposed in the brain. On the access side is an aseptic screw cap (115) and conduction rod (119) enabling intra-port recharging of the robot battery (94) through electrodes (117) leading to robot socket (125). The robot additionally disposes a Bow end rotor-stator drive coil encapsulated with hydrophobic/oleophobic-coated soft (25-50 Shore) medical device grade silicone (110), an optical camera (124) for real-time navigation reporting, RF antenna (121), RF signal processor (122) and microprocessor computer controls (120). The Stern end of the robot disposes an unexposed homopolar type drive coil (89S). The entire robot is non-stick coated similarly to the Bow drive coil. If intra-dock robot recharging through torsion fields is desired, the dock, skull gasket and access cap can be composed of MRI transparent materials such as [Al], [Ti] or ceramic coated hard polymer.

The robot is translocated from the port to the therapeutic site by creation of a FFZ in the dock. The robot is then pulled-out as the Bow drive coil rotates clockwise and the Stern drive coil counter-clockwise (or vis versa). The Bow presents a slippery, pliable and low friction implant insult for minimal damage to tissue as it navigates, monitored in real-time by both invention-provided pulsed-field MRI in toroidal geometries (see: below) and optical images. The Stern provides diametrically-opposed magnetic attraction, gyro-stabilization and potential therapeutic via charge delivery to electro-active tissue.

The illustrated scale can be used for all robot configurations described in FIGS. 30-40. Obvious to persons skilled in the art practicing the invention, robots can be developed and manufactured that are an order of magnitude smaller than those described in the invention. All components, devices, tools and medical effector functions described can be carried out with robots approximately 2 mm long and 0.5 mm wide if FFZ and torsion fields are created at those scales. It is acknowledged that field generator apparatus energies are likely to be much greater than those described to enable this scale of theranostics. Though fabrication of robot drive coils is likely not a limitation through the use of MEMS gyroscope technology, inertial gyro-stabilization will be greatly diminished from lack of angular momentum even with drive coils rotating at speeds exceeding those in preferred enablements (60-360 rpm). In such case, robot positioning can be provided more proportionally by diametrically-opposed magnetic fields, and which actuate transiently to avoid robots being uncontrollably propelled toward or away from field generators.

Figure 31:
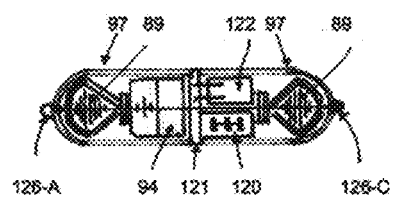
FIG. 31 describes an exemplary neurological and other electro-active tissue robot implant having bow and stern enclosed homopolar drive coils and exposed electrodes.

Referring now to FIG. 31, described is a neurological robotic device equipped with many similar charge carrying and RF devices (120, 121, 122) as the robot described in FIG. 30, however disposing two homopolar motor type drive coils (89) and a much larger battery (94). Specifically designed for effector function in electro-active tissues, this robot configuration disposes anodic (126-A) and cathodic (126-C) electrodes at the terminal extremes of the hull. The robot exhibits low CD and surface tension, translocating through brain tissue via motile FFZ without exposed propulsive components and is significantly shorter [z] and narrower [x,y] than other configuration. In a preferred enablement, the robot functions as a neurological implant for selective energization and de-energization of discreet brain tissue.

Figure 32:
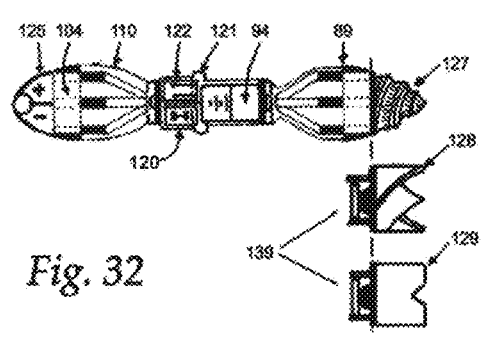
FIG. 32 describes an exemplary surgical robot with two rotor stator drives coils.

Referring now to FIG. 32, described is a surgical robotic device equipped with many similar charge carrying and RF devices (120, 121, 122) as the aforementioned robots, however disposing two rotor-stator motor type drive coils (89) with exposed rotating components. On one drive coil are disposed propulsive fins (110) and a recharging socket (125)

which also functions as part of a gyroscopic inertial mass (104). Specifically designed for effector function in tumors, diseased or necrotic tissue, the robot disposes on the other drive coil (89), a screw-type tool (127) for surgical applications. The inertial mass on that drive coil includes a receptacle through which fittings (139) can attach other surgical tools, including those for boring (128) and abrasion (129). All surgical tools can also function as gyroscopic inertial masses. In a preferred enablement, the robot carries out surgical effector functions through real-time operator guidance.

Figure 33:
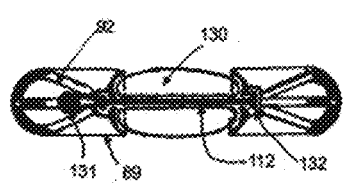
FIG. 33 describes an exemplary therapeutics delivery robot with a capsule payload shell disposed centrally about an inflexible axis tethering the drive coils. Robot lacks autonomous capability.

Referring now to FIG. 33, described is an adaptive geometry bio-therapeutics delivery robotic device having no charge carrying or RF devices. This configuration functions by mechanical actuation to convert FFZ and torsion field magnetic energies into site-specific delivery. The robot disposes two equivalent passive drive coils (89) composed of counter-rotating inertial masses having rotor bars (92) dipole moment-angled as in homopolar motor type drive coils for optimal coaxial alignment with torsion fields. Rotor bars are secured to the rest of the device via an axial knob (131) and contained within a non-rotating hull. Disposed centrally and symmetrically is a cargo volume (130) with a central, hollow axial core through which a inter-hull partially elastic connection (112) is disposed, retaining the two drive coils (132). In a preferred enablement, the robot is translocated to its target wherein more energized torsion fields compel the robot to partially expand, shattering the cargo capsule and releasing its contents.

Figure 34:
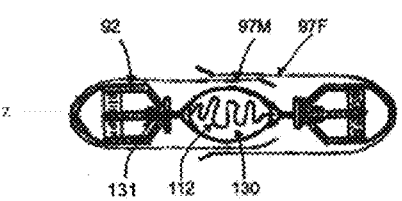
FIG. 34 describes an exemplary non-autonomous therapeutics delivery robot with a capsule payload shell disposed centrally about a flexible axis. Drive coils are encased within mating hull sections.

Referring now to FIG. 34, described is another mechanically actuating, adaptive geometry bio-therapeutics delivery robotic device that is free of charge-carrying devices. This robot disposes two similar equivalent drive coils composed of counter-rotating inertial masses having rotor bars (92) dipole moment-angled as in rotor-stator motor type drive coils. Rotor bars are secured to the rest of the device with via an axial knob (131), however are integral to mated, magnetic field transparent hull sections one of which (97M) fits into the other (97F) to minimize volume during translocation to target. Similar to the configuration described in FIG. 33, the robot disposes a central cargo volume (130) through which is threaded an inelastic elastic connection (112) retaining the two drive coils. In a preferred enablement, the robot is translocated to its target wherein more energized torsion fields compel the robot hull sections to move diametrically apart along the [z] axis, shattering the cargo capsule and releasing its contents.

In both bio-therapeutics delivery robot configurations, the lack of charge-production components in drive coil mantles and cores provides additional cargo volume for delivery of payload, acquisition of sample, or disposition of charge-carrying devices.

Figure 35:
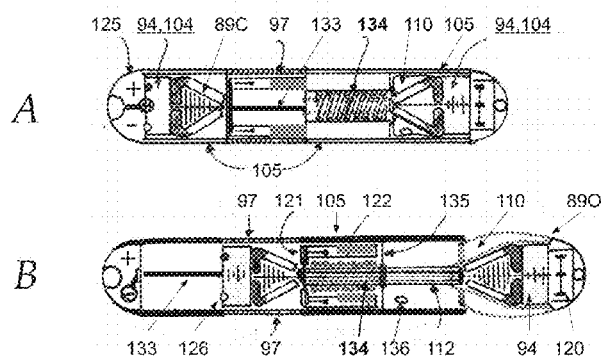
FIG. 35 describes a dynamic geometry robot for adaptive susceptibility to magnetic fields, in both "stealth"/MRI compatible mode (A) and "activated" mode (B).

Referring now to FIG. 35, described is an adaptive geometry metabolic, endocrine and other viable function monitoring robotic device having the ability to become compatible to standard in the art MRI scans. A portion of the robot comprises an open cylindrical hull disposing a recharging socket (125) on one sealed terminus (closed end), and both electromagnetic field transparent (97) and magnetic field deflecting (105) sections, the field transparent section being more centrally located than shielded sections at termini. Fixed within the hull section is a central axis (133) about which the rest of the robot portion articulates in a piston-like fashion.

Referring now to FIG. 35, A, in the MRI-compatible or "stealth" mode, most robot portions are entirely enclosed within the hull section. Describing now devices in the closed section, a battery that also serves as an inertial gyro-mass (94, 104) is in electrical contact with the recharging socket (125) via pole electrodes (FIG. 35, B—126). Proceeding now towards the other terminus, the closed end homopolar motor type drive coil (89C) is enclosed in a magnetically shielding portion of the hull (105). Attached to the drive coil are a disc geometry RF antenna (121) and a cylindrical geometry RF signal processor (122). The mantle volume disposed inside the antenna components is empty except for the piston rod (133). The antenna and signal processor devices are disposed in an unshielded portion of the hull (97). Proceeding further is axially disposed a shielded solenoid pump (134) slightly smaller in diameter than the RF devices' void volume. In the core of the solenoid pump is disposed the connecting rod (112) to the open end rotor-stator motor type drive coil (FIG. 35, B—89O). Between the solenoid pump and rotor-stator motor is a water-tight wall (135) and gasket for the connecting rod. The rotor stator motor disposes propulsion fins (110) which are partially compressed within a shielded portion of the hull (105). Lastly, the open end drive coil disposes another battery/gyro-mass (94, 104) and larger, more complex microprocessor controls with sensing device (FIG. 35, B—120). The connecting rod and central axis provide electrical connection throughout the device. All robot components, with the exception of the closed end socket (125) and open end drive coil (89O), are concentric with the central axis.

In the "active" mode, upon receipt of a RF command, on-board algorithm or analytical determination by sensor, the inner portion of the robot slides outward from the hull toward the open terminus in a piston-like fashion, enabled by the magnetic actuation of the solenoid pump. Referring now to FIG. 35, B, the closed end homopolar motor (89C) processes rightward approximately 4 mm into the unshielded portion of the hull (97), exposing drive coil rotor bars to exterior rotating magnetic fields. Concurrently, the RF components (121, 122) encompass the solenoid pump (134) by populating the pump's concentric void space. Also concurrently, the solenoid pump drives the rotor-stator motor (89O) rightward and out into the milieu, exposing it to exterior rotating magnetic fields and allowing the propulsion fins (110) to extend. Of note, the cylindrical RF signal processor (122) is now contained in a shielded portion of the robot hull (105), while the RF disc antenna (121) can receive signals through the unshielded portion (97).

The aforementioned process is reversed in returning to "stealth" mode. In unison, the homopolar motor slides back into the closed end shielded portion of the hull, the RF components all slide into an unshielded portion, and the rotor-stator motor retracts back into the closed end shielded portion, all actuated by the solenoid pump. Of note, a hole through the open end shielded hull section (136) provides hydraulic equilibrium when the rotor stator motor retracts back into that volume. It is understood that all RF components are MRI-compatible as understood in the art.

In a preferred enablement, the robot is translocated to its target in "active" mode via a FFZ and torsion fields as previously described, or be carried as payload by another robot, and placed in a therapeutic space. The robot can sense and report on biochemical processes through on-board sensors, advanced microprocessors and RF devices, and go into "stealth" mode if the patient needs to undergo a standard MRI scan. If required, the robot can translocate autonomously to another destination using its Bow propulsion fins and biochemical sensor to locate an ideal target, reporting its location in real-time via RF.

Figure 36:
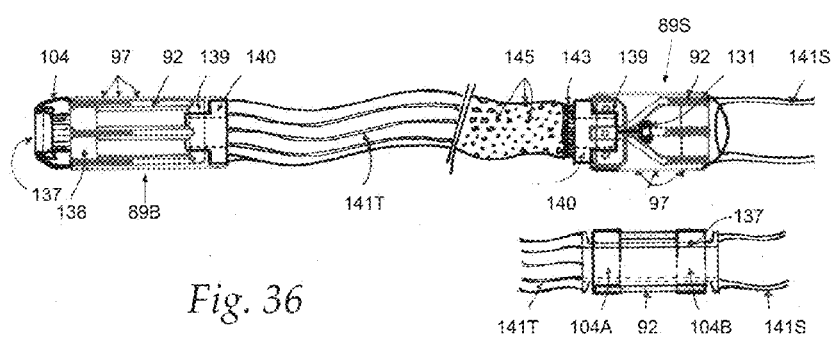
FIG. 36 describes an flexible geometry robot for biopsy collection or vascular clearance.

Referring now to FIG. 36, described is a flexible geometry robotic device having no charge carrying or RF devices. This configuration functions by mechanical actuation to process through liquid, solid and semi-solid tissues to process biological matter for collection or evisceration. The robot disposes a Bow end drive coil (89B) comprising a cylindrical geometry set of magnetized rotor bars (92) secured by front (138) and rear (139) disc-shaped retains which also serve as rotating gyro-masses. Integral to the latter is a Bow gyro-mass (104) with cutting blades in its wide (~2 mm) open bore (137). The rotor bars, retains and gyro-mass chipper freely rotate within a magnetically transparent shell (97) that is secured to a rear-ward fitting (140) about which the rotor bar retain (139) freely revolves. All components herein are preferentially PTFE coated. The gyroscopic retain (139) can attach to the fitting (140) in a female-to-male manner. Proceeding now Stern-wise, a longitudinally ribbed tubular tether of medical grade silicone (141T) attaches to a Stern drive coil (89S) through another mating of tether fitting (140) to rotor bars retain (139). The Stern drive coil disposes a set of rotor bars (92) in a homopolar motor type drive coil geometry, however dispensing with charge-generation components and rotor bars secured with an axial knob (131). The Stern drive coil is secured within a transparent hull (97) with which it rotates in unison. In another enablement, the Stern drive coil can be composed of longitudinal rotor bars (92) secured by front and rear rotating gyro-masses (104A, 104B), all disposed circumferentially around a cylinder (137) connecting the tether tube (141T) and a Stern collection bag (141S).

Figure 37:
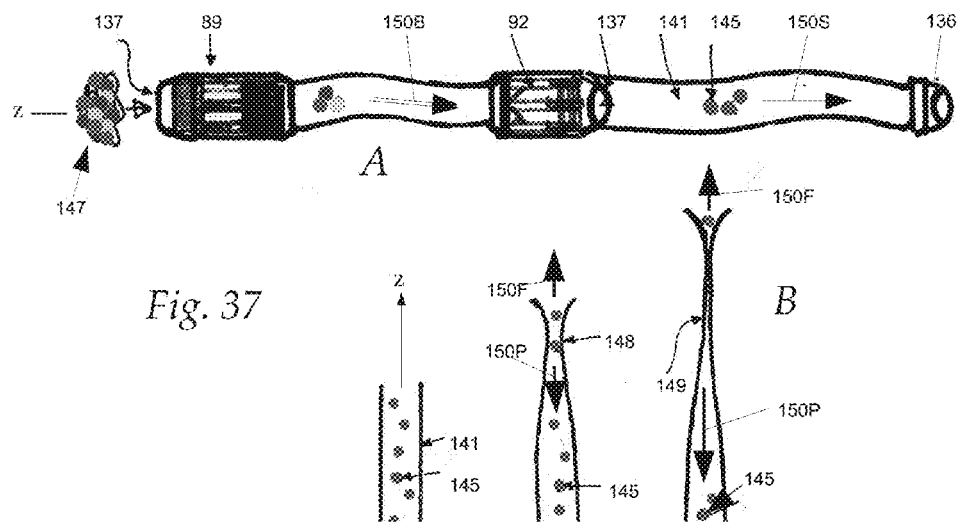
FIG. 37 describes a method for performing vascular clearance by a flexible geometry robot with the bow drive coil (left side) dis-integrating a tissue sample and transferring the cellular matter through the stern drive coil (middle) with material collection in a towed bag (right side), and a method of peristaltic transfer of material within a robot, including flexible tubing tethering drive coils.

Referring now to FIGS. 36 and 37, in a preferred enablement, after translocation to a therapeutic target and upon exposure to a FFZ and torsion fields, the Bow drive coil (89) will rotate in one direction, driving fluids and solutes (147) through the robot in the Stern-wise direction (150B). The Bow end bore will capture and accumulate particles significantly smaller than 2 mm (145) in the central tubular section (141T) which has sufficient flexibility to provide both navigation through non-linear and constricted passages, and sufficient rigidity to maintain both drive coils in a generally coaxial arrangement. Particles will continue to be accumulated until a Stern-wise filter (143), preferentially composed of medical grade polycarbonate, polystyrene or ceramic, is clogged. In the interim thereto, particles substantially smaller than filter pores will pass and process through the Stern drive coil, around the axial knob (131), and into the rear collection bag (FIG. 36—141S, FIG. 37—141) which itself disposes a Stern terminal filter (136).

In a preferred enablement, the Stern drive coil can dispose perimeter propeller-type fins (not shown) to promote pumping action rearward. In a preferred enablement, the central tether tubing (FIG. 36—141T, FIG. 37—141) can be a medical grade silicone peristaltic tube well understood in the art and providing dynamic geometry capability to the robot. The equilibrium length of the tube can be short (~5 mm) and cylindrical (FIG. 37—B, Left). Upon increased torsion field energization, the tube can stretch in a peristaltic manner preferentially initiating from the Bow end (148) resulting in hydrodynamic transfer of collected biological matter (145) in both the Bow-wise (150F) and, more proportionally, the Stern-wise (150P) direction (FIG. 37—B, Middle). Further increasing diametrically-opposed magnetic forces on drive coils results in stretching of the peristaltic tether (149) to its maximal length with further net Stern-wise (150P) transfer of particles (145) and fluid (FIG. 37—B, Right). In a preferred enablement, the Bow drive coil disposes a cylindrical blade which can be an un-beveled, edge-sharpened 12 Gauge needle for collection of "plugs" of biopsy tissue. The needle is preferably coated with a micron-scale super hydrophobic/oleophobic coating to promote efficient mechanical boring. In such aspect, a stern collection bag (FIG. 37—141) may not be required as the sample may be retained in the central tether (141T).

In another preferred enablement, the counter-rotational character of the drive coils may be used to elicit tissue transverse evisceration. In contrast to the longitudinal mechanism of tissue evisceration and collection for biopsy as described immediately prior, transverse tissue processing is provided by tools that can extend for effector function and retract for safe robot translocation. In a preferred enablement, the robot would carry out therapy of pre-thrombotic plaques characteristic of coronary artery disease Referring now to FIG. 38, described is an adaptive geometry robot for transverse tissue processing. The robot follows the standard template described in multiple preferred enablements above, herein with two rotor-stator motor geometry drive coils (89) however with current generation components and other devices in a novel configuration more suited to the application. Proceeding from a pivotable optical sensor at the Bow end (124) supported by RF reception (121), modulation (122) and microprocessor components (120), angled rotor bars (92) using the aforementioned devices as gyro-masses are connected through South poles to an axial hub (132) which is retained by an axial knob (131) at the termini of the robot central axis (112). Within a magnetic field transparent, axially articulating hull section (97), is disposed a retracted set of rotating chipper blades (227R), preferably composed of PTFE-coated hard (~75 Shore) silicone or nylon, that are axially connected to pivoting hinges on a hollow axial tube through which the central axial robot connection is disposed.

Within the rotor bars is a mantle-covered solenoid pump (134) powered by current from the robot central battery (94) to which it is hard-wired, and regulated by either central (122) or terminal microprocessors. Counter-rotation of drive coil (89) rotor bars in the refracted configuration results in rotation of POS (FIG. 38, Top—228) and NEG (FIG. 38, Top—229) poles, which are in electrical contact with mantles of drive coils, through, respectively, the NEG (FIG. 38, Bottom Right—229) and POS (FIG. 38, Bottom Right—228) axial poles of the central magnet. Disposed peripheral to the ring geometry central axis NEG pole is a shielded plate (105) protecting central axis RF (120) and computer (122) components. Current is generated in the central battery (FIG. 38, Bottom Right—94) through rotation of an axial electric field from the drive coils through a micro-induction generator composed of alternating poles (228) commonly used in the MEMS art. This arrangement is preferably replicated on both mirror-image symmetric sides of the shielded (105) central components compartment. The battery can be continuously recharged via counter-rotating torsion fields or contribute to semi-autonomous device navigation by powering drive coils, however the latter is not a preferred enablement for long term coronary artery effector protocols.

Figure 38:
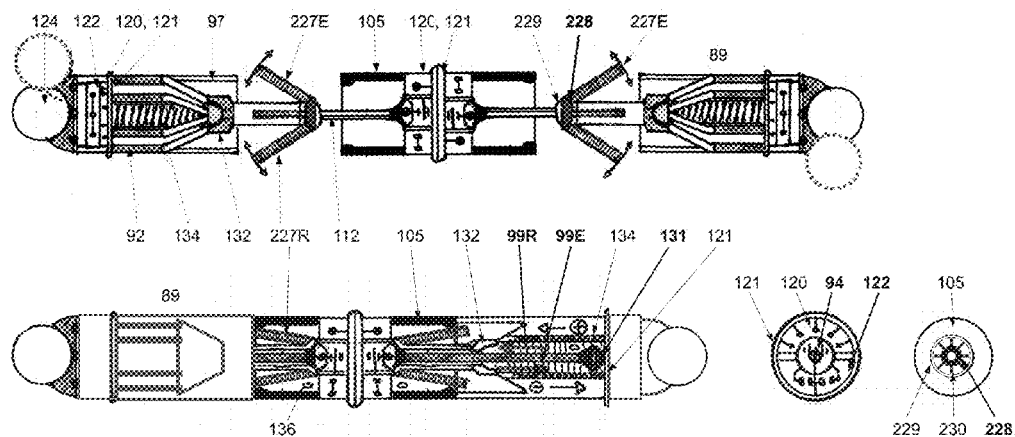
FIG. 38 describes a dynamic geometry robot for vascular clearance using retractable ablation tools, disposing an alternative on-board power supply regenerative capacity.
Figure 39:
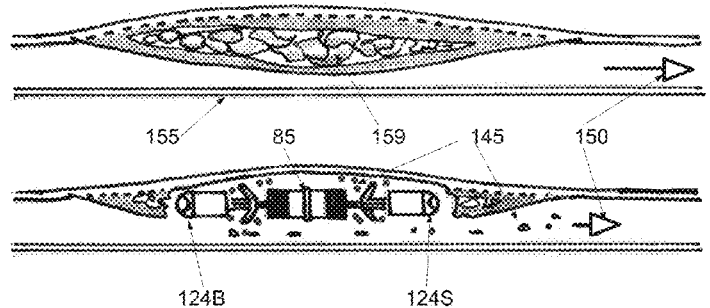
FIG. 39 describes a method for performing vascular clearance of blocked vasculature using the dynamic geometry robot with retractable ablation tools.

Referring now to FIGS. 38 and 39, upon arrival at a therapeutic target (159) being a blood vessel (155) with flow in one direction (150), and receipt of operator RF signal or internal algorithm, the electrical connections between the central battery (FIG. 38, Bottom Right—94) and two rotating axial cylinders (FIG. 38, Top—228 and 229) terminate, opening an electromagnetic safety lock. A current is then processed through the solenoid (99E) in a direction that generates a net South magnetic field in the solenoid coil, repelling the focused South ends of the rotor bars, focused axially on their set hub (132), outward. No longer retained by the non-rotating central hull section (105), the chipper blades extend to their equilibrium positions (227E) wherein ends are slightly (1-2 mm) peripheral to robot circumferential hull limits. The robot (85) can initiate the effector function of dis-integrating the coronary plaque into smaller pieces, preferably of size (145) that can safety traverse the circulatory system for disposal, through a counter-rotating chipping action. Not shown is optional disposition of a collection bag for waste biological matter as described previously (FIG. 37—141).

During the effector protocol, one or both optical cameras can be pivoted at an azimuth to the central axis (FIG. 38, Top Left—124) for real-time monitoring. This is predicted to cause significant counter-rotational precession, alternating between constructive and destructive phase rotational torquing. Although this phenomenon may contribute mechanical benefit to the effector protocol, it is preferred that optical monitoring of both bow (124B) and stern (124S) vessel conditions are carried out with all robot components either disposed concentrically or inertial mass-balanced to avoid any precession-type movement. Readily understandable by those skilled in the art, robot geometries can be varied to dispose longer chipper blades or the torsion fields can be rotated more quickly to facilitate more efficient clearance of blocked arteries.

After completion of the protocol, while held in place in the cleared therapeutic space (159), the robot can retract chipper blades by actuation of both drive coil solenoids (134) to process a current in a direction (99R) that generates a net North magnetic field in the solenoid coil, attracting the focused South ends of the rotor bars inward. Upon contact with the central hull (105), the chipper blades pivot back to their retracted positions (227R) within the unshielded hull sections (97) of both drive coils. The drive coils are pulled inward until rotating axial electrical connections contact those of the central battery, and the magnetic locks are re-engaged, securing the robot in the "safe" geometry (FIG. 38—Bottom Left) for translocation away from the therapeutic space.

Figure 40:
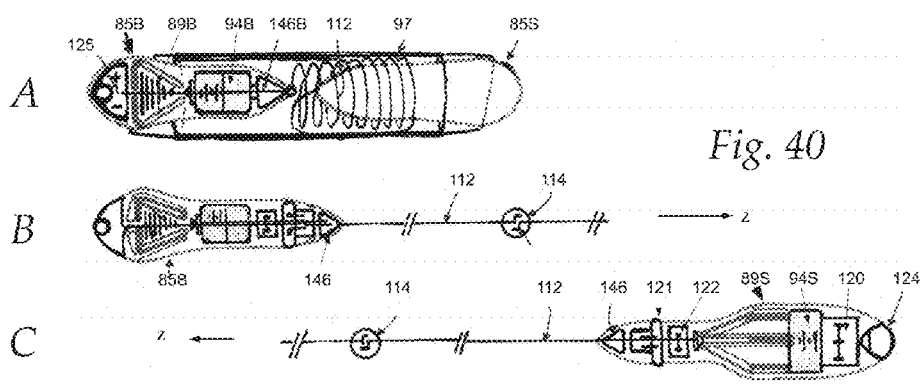
FIG. 40 describes a dynamic geometry robot for placement of conductive wire that is tether for robot hulls and is temporarily contained within a device shell (A).

FIG. 40 describes a multi-hull, adaptive geometry robot disposing a flexible tether substantially longer than the length of the assembled device, and a discardable hull in which all of the tether is initially contained and additionally substantial portions of both Bow and Stern hulls in a dock-like manner. The robot disposes substantial charge storage and current discharge capability for applications that include vascular cauterization and thermal ablation of tumor, infected or necrotic tissue. Referring now to FIG. 40, A, the Bow (85B), tether (112) and Stern (85S) robot sections are enclosed within the temporary magnetic field transparent hull. A longitudinal groove (not shown) can extend along the length of the temporary hull to facilitate passage of an extended tether. The Bow hull section disposes a recharging socket (125) at the outer terminus, a homopolar motor type drive coil (89B), substantial battery (94B) and current discharge capacitor (146B) which can be a regulated semiconductor, non-linear resistor or switch all known in the art. The tether—initially insulated then bare wire—extends from the capacitor at the Bow section inner terminus to an insulated segment at the inner terminus of the Stern hull section. The Stern hull section in this description replicates the Bow hull section in every way.

Upon formation of a FFZ and torsion fields, receipt of RF command, on-board algorithm or analytical determination by sensor—the latter with the robot acting in semi-autonomous mode—the hull sections can translocate out the hull dock in opposite directions unraveling and straightening the tether along the [z] axis. Referring now to FIG. 40, B, in an alternative device configuration, the Bow hull section (85B) disposes a smaller battery and additional RF and microprocessor components for autonomous function, as well as a discharge capacitor (146). The extended tether wire includes capsules disposed at intervals, which can contain bio-adhesive (114), bio-therapeutic, MRICA or bio-luminescent, and which can be shattered to release contents through application of current at specific modulation. Referring now to FIG. 40, C, disposed at the other extended extreme the Stern hull section (85S) carries its own capacitor pole (146), additional RF components (121, 122), substantial battery (94S), substantial microprocessor capacity (120) and optical sensor (124). The battery can also function as a rotating gyro-mass.

During drive coil actuation in torsion fields, all components except for rotor bars (and other smaller components in homopolar motor type coils as previously described) and gyro-masses remain immobile and are non-rotating. Most components dispose a small axial hole for intra-robot electrical and analytical connection, the majority of the connection being the tether. The tether is preferably composed of strong, flexible and conductive wire having appropriate electrical resistance such as low [C] steel, conductive nylon variant or [Cu—Al] co-wound thread. In a preferred enablement understood by persons skills in the art, current is discharged through the tether from one hull section to the other, and then in the reverse direction. Electrosurgery is then performed in a bipolar/bi-directional manner where current from one hull section is converted to (i) component conversion losses, (ii) Joule heating of the wire, (iii) diathermy of the exposed tissue, and (iv) collection in the other hull section. The pulses are increased in frequency, current and persistence until on-board sensors or real-time imaging determine that the therapeutic target has been neutralized. The extended robot may also be navigated across the target to facilitate neutralization as explained below, or be fixed using bio-adhesive for long term therapy.

Effector Protocols

Following are described preferred enabling methods for delivery, articulation and functional application of robotic devices. Robot navigation is understood to be carried out as previously described utilizing compression, boundary and counter-rotating torsion fields to construct a FFZ about robots, translocate robots from delivery site through healthy and unrelated tissue to their therapeutic targets, in particular utilizing motile FFZ which articulate along all coordinates as described in FIG. 20, symmetric and asymmetric FFZ as described in FIGS. 18, 19, 21 and 22, and field structure-enabled adaptive robot geometry as described in FIGS. 23, 35, 38, 39 and 40.

Figure 41:
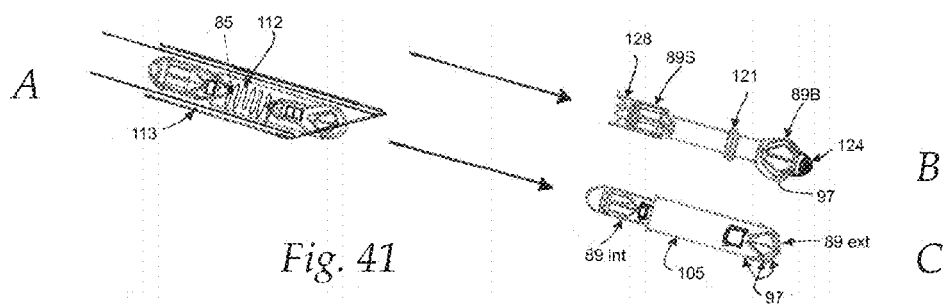
FIG. 41 describes a method of delivering a robot into a patient via injection using a standard clinical needle, the robot being one of a number of types including, as illustrated, the type described in FIG. 40 (within the needle), one of the types described for microsurgery as described in FIG. 32 (top right) and the adaptive geometry type as illustrated in FIG. 35.

In a preferred enablement, robotic devices are inserted trans-dermal or trans-cranial as described in FIG. 30. Referring now to FIG. 41, described is a simpler method for robot (85) delivery similar to that described in FIG. 40. The robot in FIG. 41, A disposes a tether (112), within a disposable or integral hull, that flexibly connects two hull sections. The robot is disposed in a dock (113) of the port, which can be a beveled 7 Gauge hypodermic needle. Also described are surgical (FIG. 41, B) and viable function monitoring (FIG. 41, C) robots, similar to those described in FIGS. 32 and 35, respectively. The surgical robot is preferably delivered to the patient with, for example, a low CD optical device (124) disposed on the Bow drive coil (89B) and the surgical tool (128) disposed on the Stern drive coil (89S). The surgical robot can use RF telemetry to report its position in greater detail using on-board devices (121). The functional monitoring robot can be of adaptive geometry design disposing both exposed, external (89 ext) and hidden, internal and axially articulating (89 int) drive coils. Partial stealth mode can be provided by both magnetic field transparent (97) and non-transparent (105) hull sections. Robot removal may require a trans-dermal/cranial dock as in FIG. 30 or minor surgery at another location to create an egress.

Figure 42:
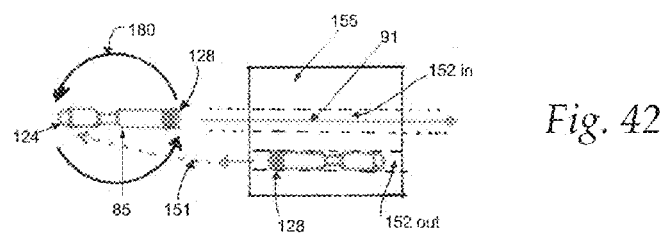
FIG. 42 describes a method for translocating a surgical robot through a therapeutic volume that utilizes 180 degree turns.

In an enablement for carrying-out evisceration-type surgical procedures such as those for neutralization of cancerous, necrotic or infected tissue, the surgical robot is translocated with the surgical tool initially disposed Stern-wise to reduce damage to, and promote greater slippage through, healthy tissue. Referring now to FIG. 42, described is a method for carrying out evisceration surgery on a therapeutic target. The robot (85), having reached a destination just outside the therapeutic target (155), execute a 180 degree turn (180) facilitated by a 180 degree articulation of field generators, similar to those described in FIG. 1, about a therapeutic space (FIGS. 1-7), resulting in rotational articulation of the FFZ within which the robot is contained. Herein now disposing the Bow device (124) away from, and its surgical tool (128) towards, the target, the robot proceeds to carry out an effector function by processing a pre-determined path (91), eviscerating a cylindrical volume as it processes inside (152 in). After departing the therapeutic target (155) on the Right side, the robot (not shown) can execute another 180 degree turn and repeat the evisceration protocol through another cylindrical volume (152 out) as it processes surgical tool end-first through the target in the other direction. After multiple 180 degree turns on both sides of the therapeutic target, with navigation in 3D to carve-out a designated volume, the robot can make its final evisceration pass and leave the therapeutic space in a path (151) that takes it to its final 180 degree turn before departure to the site of removal.

Figure 43:
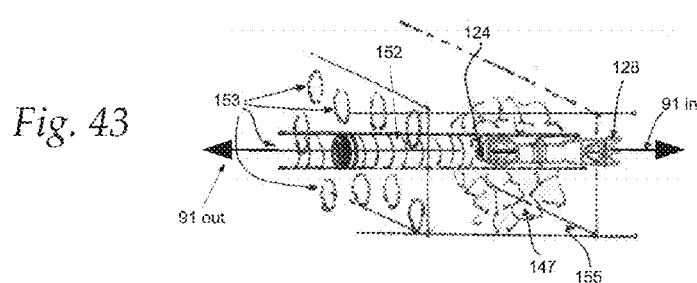
FIG. 43 describes a method for translocating a surgical robot through a therapeutic volume that does not utilize successive 180 degree turns. Illustrated surgery performed is in a back-and-forth manner from one end of the therapeutic volume.
Figure 44:
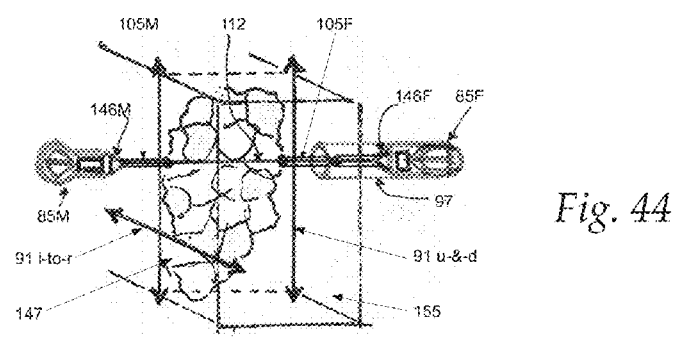
FIG. 44 describes a method for performing surgery using an adaptive geometry robot of the type described in FIG. 40.

The aforementioned method reduces collateral damage to tissue outside the therapeutic target via disposition of smooth terminus as the Bow during translocation and via untethered delivery of the surgical device. However, the multiple 180 degree turns peripheral to the target may result in unacceptable levels of collateral damage. In a more preferred enablement for for carrying-out evisceration-type surgical procedures, the robot executes a series of eviscerations with only one 180 degree turn. Referring now to FIG. 43, in a preferred enablement the robot translocates to, and executes a 180 degree turn just outside, its therapeutic target, then performs one cylindrical effector step (152) along a determined path (91 in), tool-end (128) Bow-wise, and sensor end (124) Stern-wise as described in FIG. 42. However, upon reaching the other end of the therapeutic target (155), the robot retraces its path along the now completely effected volume (152) in the reverse direction (91 out). The robot, with its surgical tool still directed towards the target volume (155), then executes a transverse maneuver and performs another evisceration step in a different entry location. Repeating the process into and out of multiple entry locations (153), with robot maneuvers limited to longitudinal effectors and transverse adjustments, significantly reduces collateral damage and can limit effect generally to the desired portions (147) of the therapeutic target which are desired for evisceration.

Mechanical evisceration may result in tissue hemmorage, spread of metastatic cancer cells and other undesired effects. Thereto, a preferred enablement for electrosurgery is provided based on the preferred enablements described above in the description for and after FIG. 40. Referring now to FIG. 43, in a preferred enablement of an electrosurgery method, an adaptive geometry robot such as that described in FIG. 41, A is translocated to a therapeutic target by the aforementioned methods. Upon reaching its destination just outside the target volume, the robot separates into male (85M) and female (85F) hull sections, the latter disposing a non-discarded, field transparent hull sheath (97). A length of tether (112) is released which is just sufficient to transect a vector across a specific portion (147) of the target volume (155), the aforementioned tether being the un-insulated portion of the central wire between insulated electrical bridges on the inner termini of the male (105M) and female (105F) hull sections. Current is then released through hull sections capacitors (146M, 146F) heating and destroying tissue in a 3D volume about the vector transected by the un-insulated portion of the wire. To electro-cauterize other, heterogeneously sized portions of the desired tissue (147), un-insulated tether length can be varied and the robot can maneuver in longitudinal directions as well as left-to-right (91 l-to-r) and up-and-down (91 u-&-d). After completion of the effector protocol, cauterizing the desired tissue, the robot can reassemble and return to its entry point or another dermal location for removal.

Figure 45:
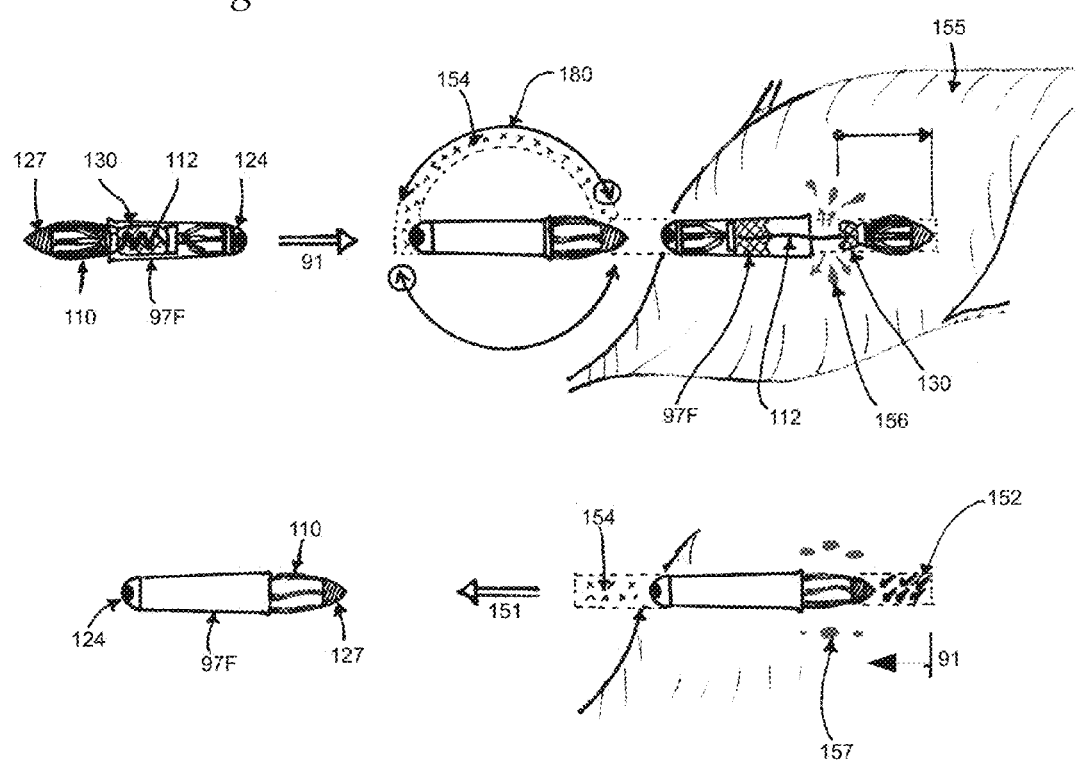
FIG. 45 describes a method of bio-therapeutics delivery to a target site (curved parallelogram).

Site-specific delivery of bio-therapeutics is provided by, for example, adaptive geometry robots disposing surgical tools. In a preferred enablement, payload such as chemotherapeutic compound, antibody, vaccine, regenerative cells, magneto-opaque tracking substance, or any combination thereto and others commonly applied in the art is delivered to the center of defined therapeutic volumes. Referring now to FIG. 45, an adaptive geometry robot with characteristics similar to those described in FIGS. 32, 34 and 35 disposes, during translocation to its destination (91, open arrow), a drilling tool (127) and propulsion fins (110) on the Stern drive coil. Disposed within a magnetic field transparent female-type hull section (97F) are disposed an elastic tether (112), inelastic material lined payload space (130) and optical sensor (124) terminal to a Bow drive coil. Similar to as described in FIG. 42, the robot executes a 180 degree maneuver (180) directly outside the therapeutic volume, creating a defined amount of collateral damage (154) mainly due to exposed drive coil and surgical tool rotation. The robot then processes through the therapeutic volume (155) along a predetermined cylindrical path (152) to a desired location. Torsion fields, possibly with participation of on-board algorithms and analytical devices, force the hull sections to separate axially, an action which stretches the tether (112) past its equilibrium length, shattering the payload lining (130) and releasing bio-therapeutic (156) in the proximal milieu.

After on-board analytical determination of payload release and disposition (157), the robot can re-assemble facilitated largely by the tether returning to its equilibrium length that re-mates the two hull sections. The assembled robot is now in the correct geometry for reverse course (91, closed arrow) translocation out of the therapeutic space (151), with its smooth terminus (124) Bow-wise, payload and tether secured in the central hull (97F) and surgical tool participating as a Stern-wise gyro-mass, having successfully delivered bio-therapeutic in a highly site-specific manner, and limiting collateral damage (excepting during translocation from the entry site) in the 180 degree turn (154) and just prior to entry into the target (155). In a preferred enablement, after payload delivery, the robot can take a tissue sample for biopsy by, for example, collection of a tissue plug by a boring action of the female section of the robot and sealing by the male section. The tether may also function mechanically to slice tissue sections if its properties are so applicable.

Figure 46:
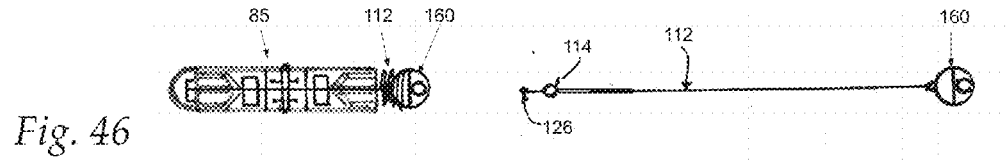
FIG. 46 describes an electro-active tissue application robot (Left), and its payload (Right) being a spherical synaptic monitoring device, conductive wire and bio-adhesive capsule.

Electro-mechanical properties of tethers can be utilized as components of semi-permanent implants for the modulation of electro-active tissue. In concert with robot devices contributing modulation of electrical, optical or magnetic energies, networks of robots, tethers and other devices can improve neurological function, create new motor networks, ameliorate pain and modulate autonomic functions amongst other applications by serving as cybernetic pathways to enhance function of those electro-active tissue systems. Referring now to FIG. 46, a carrier robot (85) with characteristics similar to those described in FIGS. 31 and 35 has translocated to a target site. The robot disposes a retracted tether (112) and electro-active sensor device which attaches to, for example, a ganglionic bundle. The robot's payload serves as the first segment of a cybernetic network comprising the ganglionic sensor (160), insulated tether (112), terminal bio-adhesive capsule (114) and terminal electrode (126). Of note, the payload of tether and sensor are carried loosely and, in a preferred enablement, do not affect drive coil functions.

Figure 47:
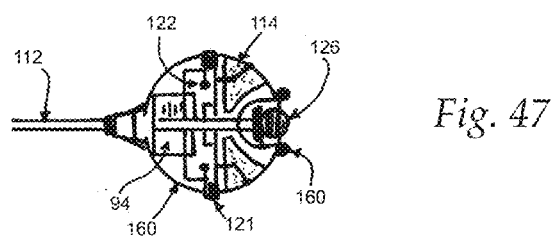
FIG. 47 describes the exemplary synaptic monitoring device components in more detail including bio adhesive containing compartments, sensor probe and equatorial RF antenna.

Referring now to FIG. 47, in a preferred enablement the ganglionic sensor has an approximate spherical shape of dimension with the robotic delivery device (FIG. 46—85). Disposing familiar components, including the insulated tether (112) on one pole, equatorial RF antenna (121), RF modulation pack (122) and battery (94), the sensor also disposes, on the opposite pole, spaces for release of electrically-conductive bio-adhesive polymer (114), magnetic particles (160) to focus discreet ganglionic magnetic fields, and a terminal electrode sensor (126). All components described herein are considered to be MRI-compatible to standard in the art scans.

Figure 48:
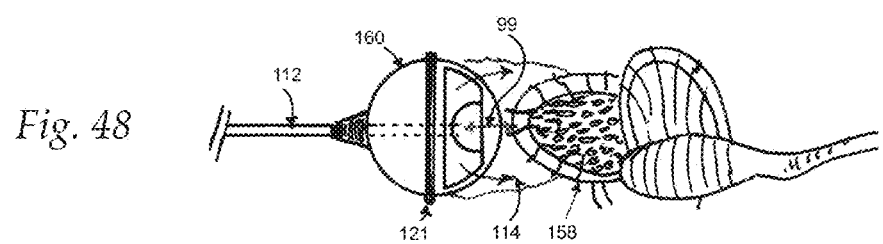
FIG. 48 describes a method for attachment of the synaptic monitoring device to ganglionic tissue using bio-adhesive to secure placement. The sensor probe has been extended into the bundle of electrically active cells.

Referring now to FIG. 48, upon placement at a specific location (158) on the target tissue, the carrier robot sends an electrical signal through the tether to release bio-adhesive (114) into the intervening space. The terminal electrode is disposed forward to close an electrical pathway (99) between the nerve bundle and the sensor unit (160). Obvious to persons skilled in the art, the battery can sensitize the terminal electrode to detect discreet electrical currents and magnetic fields, data thereto processed and reported through the RF components (121) or tether (112).

Figure 49:
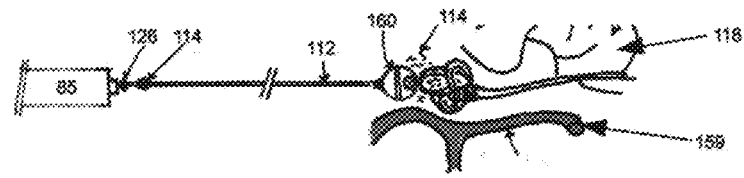
FIG. 49 describes a method of creating a conductive pathway. Briefly, the robot is translocated to the ganglionic target, the synaptic monitoring device is secured and the connecting wire unraveled as the robot pulls away (Top).
Figure 49:
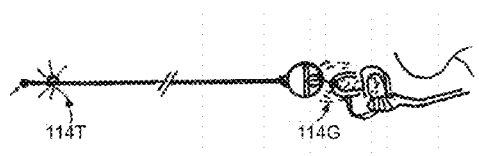

Referring now to FIG. 49, the carrier robot has placed the sensor unit (160) on the ganglion, released the bio-adhesive (114) and retracted the tether (112) along a predetermined path describing the first segment of a cybernetic network. In the Top illustration, the robot is about to release the stretched tether by detaching the terminal electrode (126) which it has held using on-board electromagnets (not shown but in a preferred enablement are similar to the battery core magnetic locks described in FIG. 38). Of note, the carrier robot has placed the ganglionic sensor and bio-adhesive mount avoiding other nervous (118) and vascular (159) tissue. Upon release of the terminal electrode, the terminal bio-adhesive capsule shatters (114T), securely mounting that end of the cybernetic network, as was previously secured the ganglionic end (114G).

Not illustrated but obvious to persons skilled in the art practicing the invention is that additional segments can be fabricated using this method. Carrier robots can place additional intelligent or RF component and microprocessor-free intersection spheres at the terminal electrode (126), repeating the process as many times as needed to complete an entire network. Also obvious, robotic devices, preferably with adaptive geometry such as those described in FIG. 35, can serve as functioning sensor implants at specific locations. Benefit provided therein is the ability to recharge the network remotely using torsion fields and the ability of the patient to undergo standard MRI scans as the robotic implants go into "stealth" mode hiding their drive coils.

Spatial Encoding and Acquisition in FFZ

Provided in the invention are methods and apparatuses for carrying out spatial encoding of, and acquisition of relaxation RF signal from, magnetic field-resonated nuclei or substances in the encoding-free homogeneous toroidal geometry magnetic structures created proximal to the central magnetic pocket that is created for robotic device management.

Figure 50:
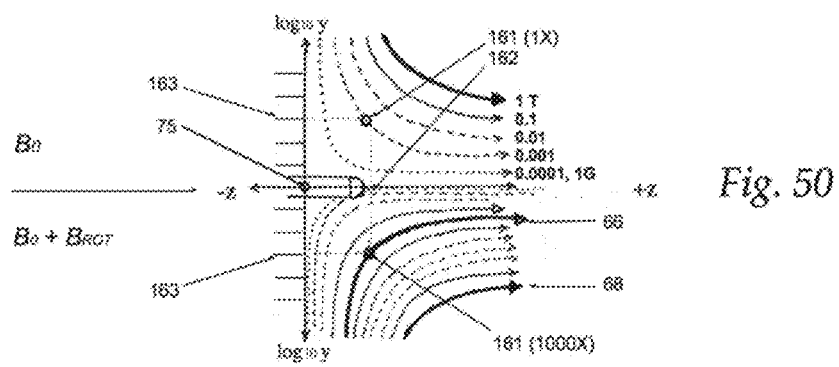
FIG. 50 describes magnetic field gradients and potentials produced close to a robot in the case of static fields (upper quadrant) and when a strong pulse field is generated (lower quadrant).

Referring now to FIG. 50, described are toroidal geometry field structures proximal to a centrally disposed (75) robotic device when static (B0, upper quadrant) or static plus rotating pulse (B0+BROT, lower quadrant) gradients are applied in the invention. Utilizing log 10 coordinates, static fields are described with decreasing field intensity from 1 T to 1 G, as labeled. Upon application of a transient magnetic pulse, field intensities at points on 2D circular coordinates on the longitudinal (162) and transverse (163) axes increase from 0.001 T (161, 1×) to 1 T (161, 1000×). The magnetic pulse is rotating (66) and peripheral to the static field (68), as previously described.

Figure 51:
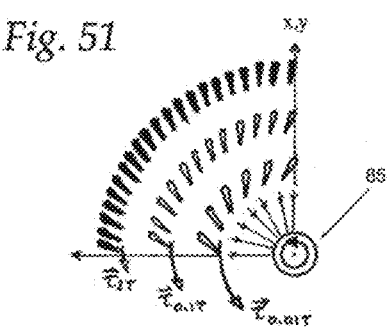
FIG. 51 describes generally magnetic intensities and net magnetization vectors of resonant targets along a radial plane at two orders of magnitude of net magnetic strength relative to a robot.

Referring now to FIG. 51, described are magnetic field intensities and net magnetization vectors during the transient rotating pulse from an axial perspective and on a plane at a given longitudinal coordinate (FIG. 50—162) on the toroidal structure looking toward the robotic device (85). If field blending at the convergence plane has occurred, field intensities are greater (T1T) where rotational rates are lower, and field intensities are lower (T0.01T) where rotational rates are greater. This further describes the field structures in FIG. 17, C, wherein constricted rotating, or "twisting," gradients are produced proximal to robot drive coils.

Figure 52:
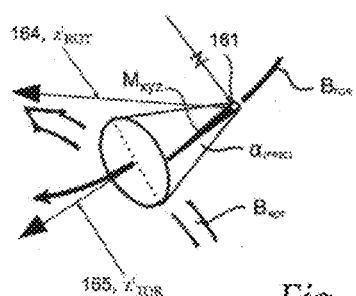
FIG. 52 describes a toroidal coordinate system for a point (x,y,z) on the toroidal surface, including static (BTOR) and rotating (BROT) gradients, with respective magnitudes and directions of net magnetization (Mx,y,z and MROT, respectively).

Referring now to FIG. 52, described is a toroidal coordinate system and MRI-related magnetic components for a single point (161) on the coordinate circle described in FIG. 50. Illustrated are direction for a diverging static field (BTOR) at intensity sufficient to weakly resonate water protons, resultant net magnetization (MXYZ) at the point, and conical precession (αPREC) directed in the positive direction of the toroidal longitudinal axis at that point (165, z'TOR), all per convention. Application of a rotating field (BROT), significantly stronger than the toroidal field, results in both an increase in magnitude and angular shift of the net magnetization (165, z'ROT) in the direction of field rotation (open arrow).

Figure 53:
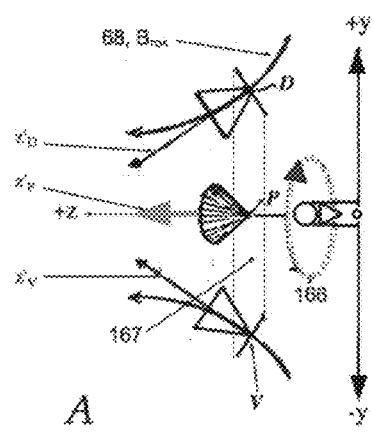
FIG. 53 describes net magnetization vector magnitudes and directions along four cardinal points at a given field strength and axial distance (z) from a robot, when static (wide cones) and static plus rotating pulse fields (narrow cones) are applied, as viewed from along the x-axis (Left) and z-axis (Right).
Figure 53:
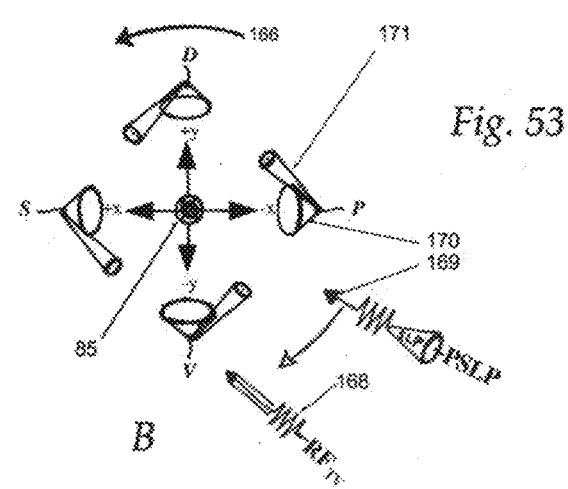

Referring now to FIG. 53, A, described are toroidal field lines at one intensity (68, BTOR), field rotational direction (166), net magnetizations (z'), precessional cones and transverse vectors normal to toroidal axes for points on the aforementioned 2D circular coordinates that are directly above (D, dorsal), below (V, ventral), to the left (S, starboard) and to the right (P, port) of the robotic device (85) disposed centrally on the reference coordinate system (FIG. 53, B). When viewed from the right three of the four points in consideration are visible, point S being covered by point P. All indicated points have unique longitudinal toroidal axes (z'D, z'P, z'V) collectively describing a 45 degree cone with base at the circular coordinates and point along the Z-axis in the intra-bore direction (+z). The net magnetization of point P (z'P) directs into the plane as indicated. Transverse planes collectively describe a truncated cone, or "pie pan," (167) with bases at the extremities of net transverse magnetization vectors if all water protons along the circular coordinates were aligned by a (π/2) RF pulse at the Larmor frequency, again per convention.

Referring now to FIG. 53, B, described are precessional cones at two field intensities, i.e., the weakly static (170) and strongly rotating (171) gradients at the four cardinal points (D,V,S,P) about the robot (85). Application of a rotating gradient (166) increases net magnetization magnitudes and decreases precessional angles, as illustrated by the relative directions and geometries of the precessional cones. If a homogeneous or otherwise non-spatially encoded volume was interrogated, no distinction could be made between relaxation signals originating from any of the cardinal (or any other) points at a given (or other) field intensity once the transient pulse was terminated. Therefore, the invention provides application of a polarized spin lock pulse (PSLP) which creates spatial bias at points 180 degrees apart along a given circular coordinate. The PSLP is RF modulated and directed, as illustrated, to the dorsal and ventral cardinal points which, upon application of a transverse RF field (168) have their transverse magnetization planes parallel to the polarity of the PLSP RF signal. All other resonant targets at points with transverse magnetization planes not aligned to the initial PSLP signal will not be biased as such. Thus, only protons or other resonant targets at or close to those 180 separated points (D and V) will be perfectly biased. As the PSLP rotates (open arrow), all points along the circular coordinate can be biased. As the PSLP signal modulation (specific for each Larmor frequency) and direction (169) are known, and the patient is maintained on the coordinate system, spatial encoding is provided to relaxation signals.

Figure 54:
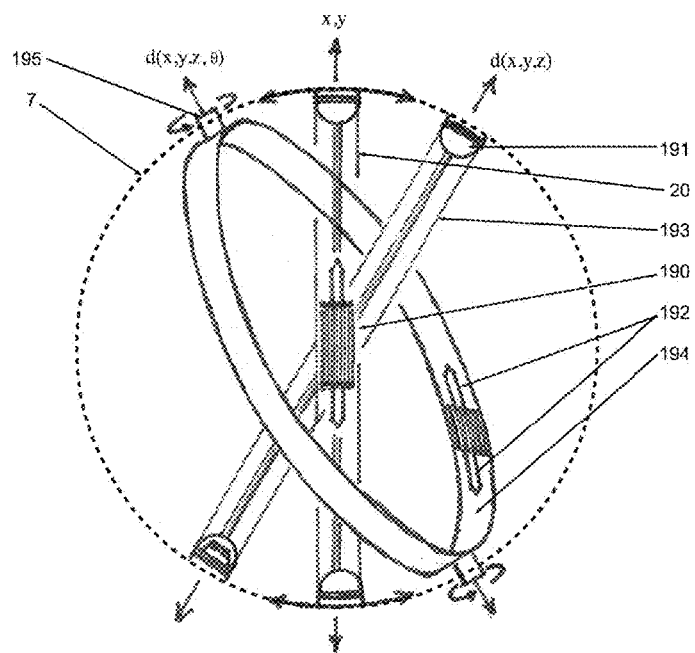
FIG. 54 describes a RF array disposed around the therapeutic space where the PSLP transmitter is contained and can be rotated 360 degrees and articulated along several axes.

In a preferred enablement, the PSLP RF transmitter is either physically or electronically rotated along a circular RF transmitter array such as that surrounding an apparatus therapeutic space (7). Referring now to FIG. 54, described is the RF array (20) having a semi-toroidal volume (191) in which is disposed a PSLP transmitter (190) which can be physically or electronically revolved (192) along the RF array. To provide bias for a range of field intensities and geometries, the transmitter array is, in addition to being electronically modulated as well understood in the art. physically articulated in a pitch-wise (193) and pitch plus yaw-wise (194) manner. The array may also be rotated at an axis (195) to the limits of the therapeutic space. The transmitter for the transverse RF signal is not shown and may be integrated into the array or be disposed in another location. If electronic rotation of the PSLP transmitter is enabled, there would be no moving parts. If physical revolution is enabled, a revolving ring such as that used for computer aided tomography (CAT), commonly practiced in the radiology art, could be integrated with the RF array.

Figure 55:
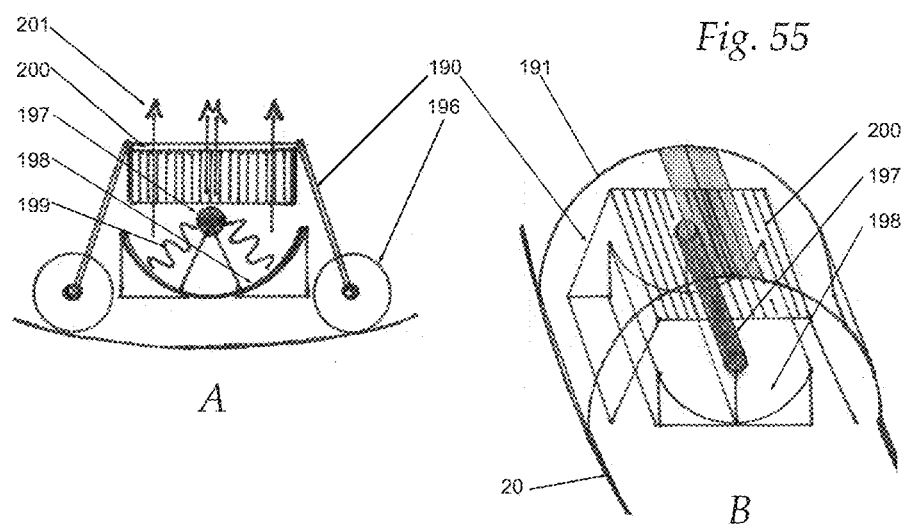
FIG. 55 describes the PSLP transmitter unit main parts (A) and disposition within the ring shaped RF transmitter array (B).

Referring now to FIG. 55, A, in one of many enablements applicable by persons skilled in the art practicing the invention, the polarized spin lock pulse transmitter comprises a spatial location system (196) and RF shielding encasement (190) enclosing a frequency-regulated transmitter (197) which is raised above a parabolic reflector (199). RF signals directed toward the reflector (199) are reflected back aligned in the same direction. Upon encounter with a polarizing filter (200), which can have both physical and electronic qualities as commonly practiced, transmitted RF signals (201) are polarized. Referring now to FIG. 55, B, the PSLP transmitter housing (190) with enclosed RF transmitter (197), reflector (198) and polarizing filter (200) are disposed within the semi-toroidal volume (191) of the RF array (20).

Figure 56:
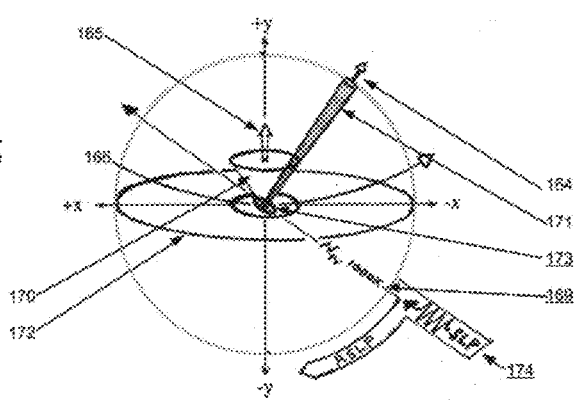
FIG. 56 describes a modified Bloch Sphere with tri-bit (three quantum state) of magnitudes, directions and precessions of net magnetization in both the low energy toroidal (small wide cone) and high energy rotated (large narrow cone) states, with disposition of the PSLP transmitter.

Referring now to FIG. 56, a Bloch Sphere is revised to describe three quantum states of net magnetization magnitudes, directions and precessional angles of the ventral point from, and utilizing the coordinate system described in, FIG. 53. The ventral point is used to center the revised Bloch Sphere with its transverse plane (172) bisecting it. As previously described, at a weak field intensities, the net magnetization vector at the point is directed in the longitudinal toroidal direction with a relatively low net magnetization (165) and large precession (170). Upon application of a strong rotating pulse (166), the net magnetization shifts and increases (164) with decreased precession (171). If a standard MRI transverse pulse were applied at the Larmor frequency of the rotating field, spin vectors would rotate about the new transverse plane (173). Invention-provided spatial encoding and novel signal acquisition of relaxing protons is provided by application of a PLSP with modulation, location (169) and polarity (174) matching the new transverse plane.

Figure 57:
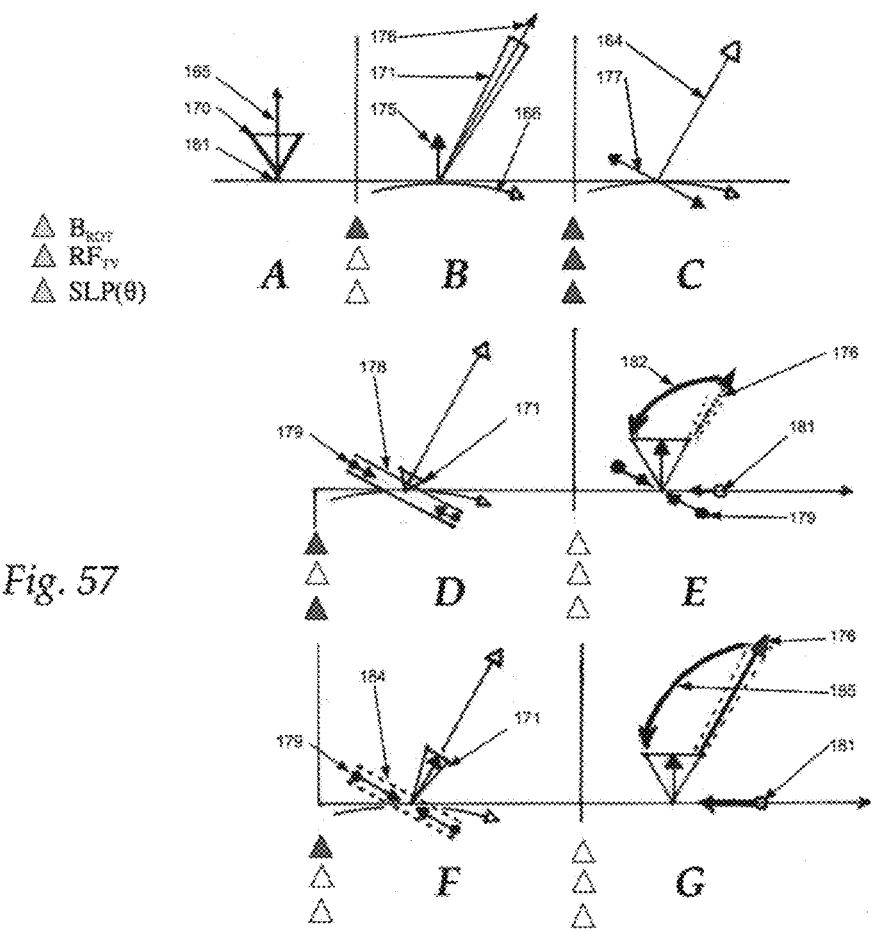
FIG. 57 describes the sequence of energization, rotation, transverse alignment, spin locking and relaxation for both perfectly spin-locked (A-E) and partially spin-locked (A-C, F-G) locations.

Referring now to FIG. 57, coordinated functions of static and rotating fields (BROT), generally directed transverse (RFTV), and PSLP RF signals directed at specific angles (SLP(θ)) provide magnetic resonance, energization, spatial encoding, relaxation and RF signal acquisition.

Statuses of rotating, standard transverse and PSLP fields are indicated by triangles (shaded being on). Illustrations are in 2D coordinates in the laboratory frame along an axis within the transverse planes of both the static, weak gradient and weak plus strong rotating gradient conditions. The coordinate abscissa is time and the ordinate is magnitude of net magnetization with generalized magnetization directions indicated.

Described in FIG. 57, A is the initial state previously described wherein weak ~10 G, static fields at a point (161), produce a widely precessing (170) toroidal magnetization vector (165). Referring now to FIG. 57, B, upon energization by a strong ~1 T, rotating magnetic gradient (166), the static magnetization remains (175), however is overwhelmed and net magnetization at the point can be accurately described by the rapidly precessing (171), angled and increased in magnitude vector (176). Referring now to FIG. 57, C, upon application of a transverse RF field and, in a preferred enablement, immediately thereafter application of a PSLP, the former net magnetization angled in the direction of rotation (164) is directed in the transverse direction (177). Referring now to FIG. 57, D, if the transverse plane of the point is aligned with PSLP signal polarity, the high energy magnetization spins (179) will be stabilized (178) in the transverse plane, even after termination of the transverse RF signal, as well understood in the art. A small net magnetization may be generated in the direction of rotation (171) in the brief interval between full termination of the transverse RF signal and full application of the PSLP.

Of note, afterward, both the strong rotating field gradient and the PSLP signal are preferably simultaneously terminated. Field gradients at the point will decline from 1 T directed in the rotational direction to a 10 G intensity directed normal to the azimuth. Return to initial state of field gradient and direction is dictated by electro-mechanical properties of field coils with expected remanence contributing to noticeable lag time. In contrast, cessation of PSLP RF signal is expected to cause magnetization spins to immediately return to longitudinal directions as understood in the art, particularly in the phenomenon of rapid T2 relaxation, specifically if a strong longitudinal (rotated or toroidal) magnetic field exists to drive relaxation in that direction.

Referring now to FIG. 57, E, upon cessation of BROT and SLP(θ), transversely magnetized spins (179) immediately return to the longitudinal direction. During the aforementioned lag time, magnetization in the rotational direction (176) partially resumes (dashed line) however immediately collapses (182) back into the toroidal direction, generating longitudinal relaxation in the reverse direction. Additionally, some transverse relaxation is contributed by longitudinal spins (181) re-aligning back to the toroidal direction.

Referring now to FIG. 57, F, upon cessation of the transverse RF signal, if the transverse plane at the point is not correctly aligned with PSLP signal polarity, high energy transverse magnetization spins (179) will be either not stabilized or only partially stabilized (184) in the transverse plane by the PSLP signal. Thus, more spins relax in a T2 manner back into the longitudinal direction of the rotated pulse resulting in greater net magnetization in the direction of rotation (171). Referring now to FIG. 57, G, upon cessation of BROT (with SLP($\theta$) being either absent or irrelevant) transversely magnetized spins will have already returned to the longitudinal direction. During the aforementioned lag time, magnetization in the rotational direction (176) is more pronounced (solid line) however also immediately collapses, herein with greater magnitude (185) back into the toroidal direction. A large longitudinal relaxation in the reverse direction is greater than if the PSLP was aligned correctly. Similarly, greater transverse relaxation is contributed by previously angled longitudinal spins (181) re-aligning back to the toroidal direction during the lag time.

Figure 58:
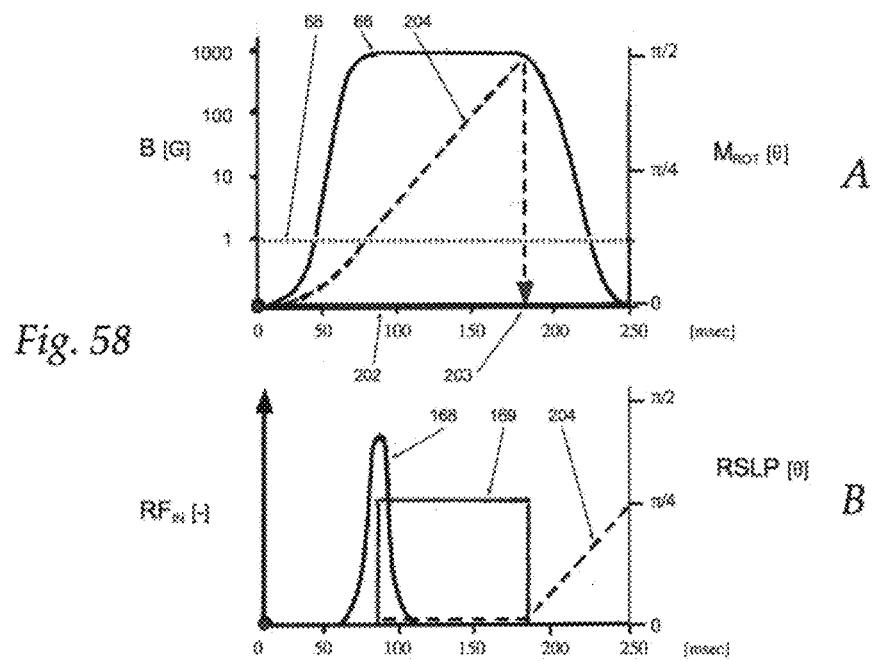
FIG. 58 describes net magnetizations of both static, baseline fields and rotating, angularly rotating fields during the 250 ms rotating pulse sequence (A), and the sequence in RF inputs from both the transverse orthogonal (B1) and PSLP pulses, the latter rotating after application (B).
Figure 59:
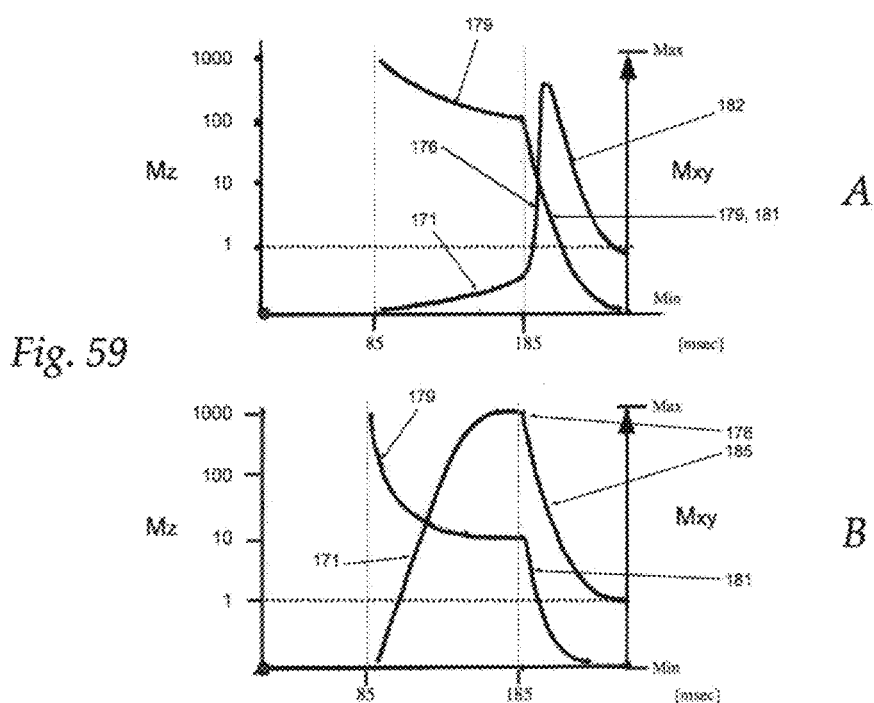
FIG. 59 describes output RF sequences of pseudoT1 T2 (T1, reverse T1, rotationally angled T2 and toroidal T2) in voxels optimally spin lock pulse locked (A) and sub-optimally locked (B).

In a preferred enablement, four 250 ms rotational pulses provided by secondary coils are applied per revolution of the field rotating at 60 Hz as described in FIG. 16. The static field provided by main coils is held invariant. Within a 250 ms window are provided the approximately 1000-fold intensity pulse, its spatial rotation, the transverse RF signal, PSLP at given 180 degree disposed points and acquisition of complex relaxation-related RF signals. All descriptions in FIGS. 58 and 59 are preferred enablements optimized for creation of torsion fields for robotic device navigation and energization. However, readily applicable by persons skilled in the art practicing the invention, a wide range of rotational frequencies, pulse frequencies and field gradient levels can be applied while maintaining the spirit and novelty of the invention.

Referring now to FIGS. 58 and 59, time (abscissa) plots describe relative magnitudes of magnetic fields, and applied angles if applicable (FIG. 58, A), input RF signals, and relative angles if applicable (FIG. 58, B), longitudinal and transverse relaxation profiles in cases of optimal (FIG. 59, A) or sub-optimal (FIG. 59, B) PSLP locking of high energy transverse spin states. As mentioned, baseline magnetic field strength is arbitrarily set at 1 G (dashed lines) for a given set of circular coordinate points on the toroidal surface. Field strengths both net (B[G]) and longitudinal (MZ) are relative to the static baseline; 1000-fold being 1 T. Strengths for transverse (MXY) fields are relative to their maximal values (Max) in transversely-aligned, perfectly spin-locked, high energy states, to minimal values (Min) in longitudinal, toroidal low energy states. The ordinate for RF strength is dimensionless (RFIN [–]). Signal acquisition from longitudinal and transverse relaxation profiles is preferably performed in two heterogeneous time blocks, one immediately after termination of the transverse RF signal at 85 ms until termination of the PSLP at 185 ms, and the other thereafter. As in FIG. 57, all signal acquisition curves are taken in the laboratory frame.

Referring now to FIG. 58, A, described are relative magnitudes (B[G]) of applied static and rotating magnetic fields, and the angular distance traversed by the rotating field. Within a 250 ms, quarter-turn secondary coil rotational cycle, the static field (68) is held constant while the rotating field (66) is increased slowly from nearly zero to 1000-times the static field strength in approximately 85 ms (202). The rotating field is then maintained for 100 ms (203), then de-energized and allowed to dissipate until extinguishing completely after approximately another 65 ms. During energization, the secondary field is rotated (204) at a nearly constant rate from its initial alignment (0, right ordinate) to one quarter turn ($\pi/2$) in approximately 185 seconds, at which point it is terminated.

Referring now to FIG. 58, B, described is the very brief transverse RF pulse (168), optimally applied at the point of maximal rotating field strength, i.e., 85+/−25 ms. No directional preference is specified, however the RFTV is applied orthogonally as commonly practiced in the art. Also described is the PSLP (169)—aligned correctly (RSLP($\theta$)=0) with desired 180 degree separated toroidal surface targets—which is energized immediately upon achievement of maximal rotational gradient at 85 ms. The PSLP oscillates in phase and on resonance with target points. After a 100 ms SLP, the signal is terminated concurrently with termination of the rotational gradient at 185 ms, and the PSLP transmitter is electronically or physically rotated (204) ⅛ of a turn ($\pi/4$) to spatially encode another two 180 degree disparate target points. All 1 mm3 voxels along a 10 cm diameter toroidal analysis circle (including the D, V, S, P and all intervening points) can be interrogated with thirty two PSLP cycles rotating at ($\pi/16$) every 250 ms secondary field pulse, or with discreet angular shifts to cover the entire analysis zone, in 8 seconds at 60 Hz of secondary field rotation.

Referring now to FIG. 59, A, described are longitudinal and transverse relaxation profiles in the case of optimal spin locking of high energy transverse spin states. In the first time block, the T1 curve describes the small, partial T1 relaxation (171) that occurs immediately after RFTV intensity apex but limited by the correctly modulated PSLP. In the second time block, the longitudinal relaxation is described by a bi-phasic curve that includes (i) rapid T1 relaxation driven by the declining but still substantial rotating field pulse, resulting in longitudinal energization increasing from <1 G to approximately 100 G in ~15 ms (176), and (ii) classic T1 relaxation (182) as the rotating field continues to decline and net longitudinal magnetization degrades further until baseline. In the first time block, the T2 curve describes the partial T2 relaxation (179) of transverse spins after cessation of the transverse signal, but maintenance of the SLP. In the second time block, the T2 curve describes the rapid collapse of all remaining transverse magnetizations into longitudinal ones as the correctly modulated PSLP is terminated and transversely oriented spin states relax (179), and as high energy, angled longitudinal magnetization vectors tilt back to the toroidal normal (181), losing any remaining transverse quality excepting precession.

Referring now to FIG. 59, B, described are longitudinal and transverse relaxation profiles in the case of sub-optimal spin locking of high energy transverse spin states. In the first time block, the T1 curve describes (i) the substantial T1 energization (179) that occurs immediately after RFTV intensity apex, only partially limited by the incorrectly modulated PSLP, and driven by the strong rotating gradient until plateau (176), and (ii) classic T1 relaxation (185) as the rotating field continues to decline and net longitudinal magnetization degrades further until baseline. In the first time block, the T2 curve describes the rapid T2 relaxation (179) of transverse spins after cessation of the transverse signal, due to inadequate SLP. In the second time block, the T2 curve describes the very rapid collapse of all remaining transverse magnetizations into longitudinal ones as angled longitudinal magnetization vectors tilt back to the toroidal normal (181). The latter is estimated to extinguish before the end of the 250 ms cycle.

Magic Angles and Laser Optical Gyroscopes

Referring now to FIG. 60, described are standard magic angle spinning (FIG. 60, A), and invention provided magic angle turning (FIG. 60, B). In the MAS illustration of FIG. 60, A, a cylindrical sample (202) rotates (204) along an axis exposed to linear magnetic fields directed at the magic angle. Fields intersect with the robot at the MA along a 2D curved rectangular surface (205). In a preferred enablement described in FIG. 60, B, the toroidal magnetic field (66) rotates (166) allowing field lines at a given intensity to intersect with the robot (85) at the MA along a 2D narrow cylindrical surface (205). Robot drive coils disposed at the MA location can likewise rotate or an on-board, rapidly rotating gyroscope can be carried and exposed to MA rotating fields for enhanced MAT type image resolution, particularly at very low field intensities with improved resolution due to increased relative rotation of fields vs. rotating sample. The gyroscope can carry out other functions specific to analysis of very low magnetic field intensities, such as those produced in neural synapses, through analytical performance approaching superconducting quantum interference detectors (SQUID), herein not obligated to cryogenic cooling of detector or signal processor components.

Referring now to FIG. 61, a spherical assembly (208) is stably disposed, untethered between two concentric inductor ring sections utilizing magnetic levitation technology well understood in the art. The sphere disposes two permanent magnetic dipole sub-polar (+/−z) to trans-equatorial components, one disposing a sub-polar North magnetic pole (213) leading to a trans-equatorial South disc (214), the other disposing a sub-polar South magnetic pole (215) leading to a trans-equatorial North disc (216). Between the two equatorial discs, which are separated a distance, is disposed a stack (206) of approximately twenty 10 um thick optical glass, quartz or SiO2 discs bonded together, or a disc shaped block of optical crystal polarized (207) in the equatorial direction. The optical sphere disposes charge-carrying inductor plates (212) from which micro-fabricated field coils (211) in the suspension rings (209) both levitate and rotate the sphere along the z-axis and magnetized poles. Magnetized counter-poles on the ring can provide additional levitation stability by North-to-North (186) and South-to-South (187) repulsion. Laser energy that is polarized parallel to the equatorial polarization processes into (201) and out of (210) the optical section of the sphere at an efficiency determined by the sphere orientation.

Referring now to FIG. 62, the magnetic field generated between the equatorial disc poles is described. Gradients (215) process from North to South discs beyond a field non-transparent, insulated coating (214). The equatorial discs extend beyond the polarized equatorial disc (207). Extremities of the levitation ring dispose electro-magnetically insulating sections (218) to block interference from field coils, and conductive termini (217) to promote encounters with exterior magnetic fields. Upon exposure to an exterior magnetic gradient directed an azimuth (219), the sphere is tilted at an angle (220). The sensitivity of the LOG to exterior magnetic fields is decreased by more rapid sphere rotation resulting in greater gyroscopic stability. Sensitivity is increased by slower rotation and/or decreased energization of field coils, wherein the optical sphere is levitated largely by counter poles and induced current to sphere inductor plates of a non-rotational quality, i.e., unidirectional and not revolving. In a preferred enablement, the dipole moment of the equatorial disc-and-submerged pole components can be electronically modulated to contribute additional sensitivity to exterior magnetic fields.

Referring now to FIG. 63, the support components are described. A laser source (221) and polarizing filter (200) are disposed opposite a photomultiplier optical chip (223) with the equatorial optical disc stacks of two LOG units in the beam path (222). Disposed adjacent to the detector LOG unit sphere (208) and suspension ring (209) is a control LOG sphere (224) that replicates the detector sphere in every way except that the equatorial disc-and-submerged pole components of the control sphere (225) lack a magnetic moment. The entire assembly can be fabricated on a ~4 mm wide (x,y-axis, from laser to photomultiplier chip) base board. Test electrodes (226) are energized to generate different magnitudes and directions of magnetic fields to calibrate the LOG.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

What is claimed is:

1. A magnetic field generating apparatus comprising: two or more co-facing, coaxial magnetic field generators, each generator comprising a first set of cryogenically-cooled superconducting field coils, a second set of concentric, coaxial, mechanically revolving field coils, and a tertiary set of concentric, coaxial peripheral field coils, wherein the generators are configured to generate equivalent magnetic fields directed toward a symmetrically central convergence plane; a magnetically shielding encasement configured to contain all of the associated magnetic fields generated by the coaxial magnetic field generators; and articulation frames and supports for positioning of the apparatus field generators about a fixed point, enabling orientation of magnetic fields about the fixed point such that fields are co-facing, coaxial and dispose field elements that revolve in opposite directions relative to the fixed point, wherein oppositely revolving field elements are generated by concentric, co-facing, coaxial field coils disposed intra-bore of each field generator, and wherein intra-bore field coils mechanically revolve in opposite directions relative to the fixed point.

2. The magnetic field generator apparatus of claim 1, wherein the magnetically shielding encasement has geometries that focus magnetic fields into toroidal and compressive geometries.

3. The magnetic field generator apparatus of claim 1, wherein the apparatus supports and articulations are configured to cooperate with patient supports to enable millimeter scale precision in relative positioning of apparatus to patient.

4. The magnetic field generator apparatus of claim 1, wherein the counter-rotating fields converge toward a therapeutic, extra bore volume.

5. The magnetic field generator apparatus of claim 1, wherein the field coils are energized in a convergent or Anti-Helmholtz fashion.

6. The magnetic field generator apparatus of claim 1, wherein the second set of field coils is disposed extra-bore and revolved to generate rotating magnetic field elements.

7. The magnetic field generator apparatus of claim 1, wherein the second set of field coils disposes rotating axial magnetic dipole rods and focusing shields.

8. The magnetic field generator apparatus of claim 1, wherein a third set of field coils is disposed concentrically and peripherally to generate outermost field elements which can be axially longitudinal or rotate about the bore axis.

9. The magnetic field generator apparatus of claim 1, wherein at least some of the field coils have uniform radius.

10. The magnetic field generator apparatus of claim 1, wherein at least some of the field coils have varying radius.

11. The magnetic field generator apparatus of claim 1, wherein at least some of the field coils are configured to generate about 1-9 Tesla [T].

12. The magnetic field generator apparatus of claim 1, wherein at least some of the field coils are configured to generate invariant field gradients in apparatus bores.

13. The magnetic field generator apparatus of claim 12, wherein the invariant field gradients are configured to facilitate at least one of robotic control, spatial encoding, and signal acquisition in voxels outside bores.

14. The magnetic field generator apparatus of claim 1, wherein the field coils are energized to generate toroidal field structures characteristic of Helmholtz, Maxwell, Tesla, Rodin, or Solenoid electromagnetic coil types.

15. The magnetic field generator apparatus of claim 1, wherein the second set of concentric, coaxial revolving field coils are configured to generate and focus rotating field elements peripheral to and concentric with static fields.

16. The magnetic field generator apparatus of claim 1, wherein the tertiary set of concentric, coaxial peripheral field coils are configured to generate boundary fields for partitioning of rotating field elements produced by the second set of concentric, coaxial revolving field coils.

17. The magnetic field generator apparatus of claim 1, wherein the tertiary set of concentric, coaxial peripheral field coils are disposed peripheral to all other field coils, partitioned by shielding, and configured to produce the outermost field elements.

18. The magnetic field generator apparatus of claim 1, wherein the tertiary set of concentric, coaxial peripheral field coils are configured to generate rotating magnetic fields through application of alternating current (AC) through helically-wound conduction pathways.

19. The magnetic field generator apparatus of claim 1, wherein the magnetically shielding encasement comprises low magnetic field susceptibility and transparency.

20. The magnetic field generator apparatus of claim 1, wherein the magnetically shielding encasement present geometries that focus field energies onto desired targets, and disposed to partition autonomous field elements and physically support field coils.

* * * * *